(12) United States Patent
Bishop et al.

(10) Patent No.: US 10,174,081 B2
(45) Date of Patent: Jan. 8, 2019

(54) ANTIMICROBIAL PEPTIDES AND USES THEREFORE

(75) Inventors: Barney Bishop, Annandale, VA (US); Monique van Hoek, Centreville, VA (US)

(73) Assignee: George Mason Research Foundation, Inc., Fairfax, VA (US)

( * ) Notice: Subject to any disclaimer, the term of this patent is extended or adjusted under 35 U.S.C. 154(b) by 0 days.

(21) Appl. No.: 14/113,158

(22) PCT Filed: Apr. 20, 2012

(86) PCT No.: PCT/US2012/034529
§ 371 (c)(1),
(2), (4) Date: Jan. 8, 2014

(87) PCT Pub. No.: WO2012/145680
PCT Pub. Date: Oct. 26, 2012

(65) Prior Publication Data
US 2014/0128313 A1    May 8, 2014

Related U.S. Application Data

(60) Provisional application No. 61/477,874, filed on Apr. 21, 2011, provisional application No. 61/556,988, filed on Nov. 8, 2011, provisional application No. 61/556,983, filed on Nov. 8, 2011, provisional application No. 61/556,993, filed on Nov. 8, 2011, provisional application No. 61/635,589, filed on Apr. 19, 2012.

(51) Int. Cl.
| | |
|---|---|
| C07K 14/00 | (2006.01) |
| C07K 7/06 | (2006.01) |
| A01N 37/46 | (2006.01) |
| C07K 7/08 | (2006.01) |
| C07K 14/47 | (2006.01) |
| C12Q 1/18 | (2006.01) |
| A61K 38/00 | (2006.01) |
| A61K 38/08 | (2006.01) |
| A61K 38/10 | (2006.01) |
| A61K 38/17 | (2006.01) |

(52) U.S. Cl.
CPC ............ *C07K 14/001* (2013.01); *A01N 37/46* (2013.01); *C07K 7/06* (2013.01); *C07K 7/08* (2013.01); *C07K 14/4723* (2013.01); *C12Q 1/18* (2013.01); *A61K 38/00* (2013.01); *A61K 38/08* (2013.01); *A61K 38/10* (2013.01); *A61K 38/17* (2013.01)

(58) Field of Classification Search
CPC .... C07K 7/06; C07K 14/001; C07K 14/4723; C07K 7/08; A61K 38/08; A61K 38/10; A61K 38/17
See application file for complete search history.

(56) References Cited

U.S. PATENT DOCUMENTS

| 8,404,636 | B2 | 3/2013 | Bishop et al. | |
|---|---|---|---|---|
| 2007/0065908 | A1* | 3/2007 | Gallo | A61K 38/10 |
| | | | | 435/69.1 |
| 2010/0022750 | A1 | 1/2010 | Bishop et al. | |
| 2012/0149631 | A1 | 6/2012 | Delatour et al. | |
| 2016/0367692 | A1 | 12/2016 | Bishop et al. | |

FOREIGN PATENT DOCUMENTS

| CN | 101265296 A * | 9/2008 | ............. A61P 31/00 |
|---|---|---|---|
| CN | 101386640 A * | 3/2009 | |
| WO | WO 2007076162 A2 * | 7/2007 | ............. C07K 14/47 |
| WO | WO 2009001087 A2 * | 12/2008 | ............. A61L 15/32 |
| WO | WO 2010091294 A2 * | 8/2010 | ............. A61K 38/00 |
| WO | WO 2010/148079 | 12/2010 | |

OTHER PUBLICATIONS

Hui Zhao, Identification and characterization of novel reptile cathelicidins from elapid snakes Peptides, 29 (2008) pp. 1685-1691.*
UniProt Protein Database, Cathelicidin-NA antimicrobial peptide, protein Accession B6S2X0, accessed on Dec. 11, 2014.*
T. D. Day, The Permeability of Interstitial Connective Tissue and the Nature of the Interfibrillary Substance, J. Physiol. (1952), 117 pp. 1-8.*
EPO English Translation of the Description for CN101265296, accessed on Dec. 11, 2014, pp. 1-22.*
Frank A. de Latour, Antimicrobial activity of the Naja atra cathelicidin and related small peptides, Biochemical and Biophysical Research Communications 396 (2010) 825-830.*
Matthew J. Betts, Amino Acid Properties and Consequences of Substitutions, Bioinformatics for Geneticists. Edited by Michael R. Barnes and Ian C. Gray, 2003.*
Google Translation of CN101386640A, accessed on Jun. 10, 2016.*
Kinexus, Custom Services, Peptide array production, published online Jan. 27, 2010.*
Mimotopes, Overcoming Peptide Problems by Design, published online Feb. 1, 2009.*
International Preliminary Report on Patentability in International Application No. PCT/US2012/034529, dated Oct. 22, 2013, 9 pages.
International Search Report and Written Opinion in International Application No. PCT/US2012/034529, dated Nov. 7, 2012, 15 pages.
"Research on microbial biofilms (PA-03-047)," NIH, National Heart, Lung, and Blood Institute, 2002, 13 pages.
Abrunhosa et al., "Interaction and lipid-induced conformation of two cecropin-melittin hybrid peptides depend on peptide and membrane composition," J Phys Chem B, 2005, 109(36):17311-9.
Altman et al., "In vitro assessment of antimicrobial peptides as potential agents against several oral bacteria," Antimicrob Chemother, 2006, 58(1):198-201.

(Continued)

*Primary Examiner* — Rachael E Bredefeld
*Assistant Examiner* — Erinne R Dabkowski
(74) *Attorney, Agent, or Firm* — Coeus Intellectual Property

(57) ABSTRACT

Materials and methods for making and using cationic antimicrobial peptides (CAMPs), and compositions containing such peptides.

24 Claims, 41 Drawing Sheets
Specification includes a Sequence Listing.

(56) References Cited

OTHER PUBLICATIONS

Amer et al., "Antimicrobial and antibiofilm activity of cathelicidins and short, synthetic peptides against Francisella," Biochem Biophys Res Commun, 2010, 396(2):246-251.

Apicella et al., Gonococcal Biofilms,, in Neisseria: Molecular Mechanisms of Pathogenesis, Caister Academic Press, 2010, pp. 55-60.

Bagge et al., "Pseudomonas aeruginosa biofilms exposed to imipenem exhibit changes in global gene expression and beta-lactamase and alginate production," Antimicrob Agents Chemother, 2004, 48(4):1175-1187.

Bals et al., "The peptide antibiotic LL-37/hCAP-18 is expressed in epithelia of the human lung where it has broad antimicrobial activity at the airway surface," Proc Natl Acad Sci USA, 1998, 95(16):9541-9546.

Barrett and Barrett, "Antibacterials: are the new entries enough to deal with the emerging resistance problems?" Curr Opin Biotechnol, 2003, 14(6):621-626.

Beckloff et al., "Activity of an antimicrobial peptide mimetic against planktonic and biofilm cultures of oral pathogens," Antimicrob Agents Chemother, 2007, 51(11):4125-4132.

Bone, "Gram-negative sepsis: a dilemma of modern medicine," Clin Microbiol Rev, 1993, 6(1):57-68.

Braff et al., "Structure-function relationships among human cathelicidin peptides: dissociation of antimicrobial properties from host immunostimulatory activities," J Immunol, 2005, 174(7):4271-4278.

Braff et al., "Keratinocyte production of cathelicidin provides direct activity against bacterial skin pathogens," Infect Immun, 2005, 73(10):6771-6781.

Brogden, "Antimicrobial peptides: pore formers or metabolic inhibitors in bacteria?" Nat Rev Microbiol, 2005, 3:238-250.

Bucki et al., "Antibacterial activities of rhodamine B-conjugated gelsolin-derived peptides compared to those of the antimicrobial peptides cathelicidin LL37, magainin II, and melittin," Antimicrob Agents Chemother, 2004, 48(5):1526-1533.

Chennupati et al., "Effects of an LL-37-derived antimicrobial peptide in an animal model of biofilm Pseudomonas sinusitis," Am J Rhinol Allergy, 2009, 23(1):46-51.

Costerton et al., "Bacterial biofilms: a common cause of persistent infections," Science, 1999, 284(5418):318-1322.

Cox et al., "Susceptibility of Treponema pallidum to host-derived antimicrobial peptides," Peptides, 2003, 24:1741-1746.

D'Errico et al., "Interaction between Alzheimer's Abeta(25-35) peptide and phospholipid bilayers: the role of cholesterol," Biochim Biophys Acta, 2008, 1778(12):2710-6.

Davis et al., "Microscopic and physiologic evidence for biofilm-associated wound colonization in vivo," Wound Repair and Regeneration, 2008, 16(1):23-29.

de Latour et al., "Antimicrobial activity of the Naja atra cathelicidin and related small peptides," Biochem Biophys Res Commun, 2010, 396:825-830.

De Yang et al., "LL-37, the neutrophil granule- and epithelial cell-derived cathelicidin, utilizes formyl peptide receptor-like 1 (FPRL1) as a receptor to chemoattract human peripheral blood neutrophils, monocytes, and T cells," J Exp Med, 2000 192(7):1069-1074.

Dean et al., "Natural and synthetic cathelicidin peptides with anti-microbial and anti-biofilm activity against Staphylococcus aureus," BMC Microbiol, 2011, 11(114):1-12.

Dean et al., "Susceptibility of Pseudomonas aeruginosa biofilm to alpha-helical peptides: D-enantimoer of LL-37," Frontiers Microbiol, Jul. 2011, 2(128):1-11.

Dieter, "Coronary artery stent infection," Catheter Cardiovasc Interv, 2004, 62(2):281.

Donlan and Costerton, "Biofilms: survival mechanisms of clinically relevant microorganisms," Clin Microbiol Rev, 2002, 15(2):167-193.

Drenkard and Ausubel, "Pseudomonas biofilm formation and antibiotic resistance are linked to phenotypic variation," Nature, 2002, 416(6882):740-743.

Durham-Colleran et al., "Francisella novicida forms in vitro biofilms mediated by an orphan response regulator," Microb Ecol, 2010, 59:457-465.

Falla et al., "Mode of action of the antimicrobial peptide indolicidin," J Biol Chem, 1996, 271(32): 19298-303.

Gallo et al., "Biology and clinical relevance of naturally occurring antimicrobial peptides," J Allergy Clin Immunol, 2002,110(6):823-831.

Ganz and Weiss, "Antimicrobial peptides of phagocytes and epithelia," Semin Hematol, 1997, 34:343-354.

Gennaro et al., "Biological characterization of a novel mammalian antimicrobial peptide," Biochim Biophys Acta, 1998, 1425:361-368.

Gerke et al., "Characterization of the N-acetylglucosaminyltransferase activity involved in the biosynthesis of the Staphylococcus epidermidis polysaccharide intercellular adhesin," J Biol Chem, 1998, 273:18586-18593.

Goldman et al., "Human β-defensin-1 is a salt-sensitive antibiotic in lung that is inactivated in cystic fibrosis," Cell, 1997, 88(4):553-560.

Gordon et al., "Human cathelicidin (LL-37), a multifunctional peptide, is expressed by ocular surface epithelia and has potent antibacterial and antiviral activity," Curr Eye Res, 2005, 30:385-394.

Gross and Meienhofer, The Peptides: Analysis, Synthesis, Biology, Academic Press, Inc., New York, 1983, 12 pages, title pages and table of contents only.

Hall-Stoodley et al., "Bacterial biofilms: from the natural environment to infectious diseases," Nat Rev Microbiol, 2004, 2(2):95-108.

Han et al., "Antimicrobial activity of human betadefensins and induction by Francisella," Biochem Biophys Res Commun, 2008, 371:670-674.

Hancock and Speert, "Antibiotic resistance in Pseudomonas aeruginosa: mechanisms and impact on treatment," Drug Resist Update, 2000, 3(4):247-255.

Heilborn et al., "The cathelicidin anti-microbial peptide LL-37 is involved in re-epithelialization of human skin wounds and is lacking in chronic ulcer epithelium," J Invest Dermatol, 2003, 120:379-389.

Hell et al., "Human cathelicidin peptide LL37 inhibits both attachment capability and biofilm formation of Staphylococcus epidermidis," Lett Appl Microbiol, 2010, 50:211-215.

Heyland et al., "The attributable morbidity and mortality of ventilator-associated pneumonia in the critically ill patient. The Canadian Critical Trials Group," Am J Respir Crit Care Med, 1999, 159(4 Pt 1):1249-1256.

Hider, "Honeybee venom: a rich source of pharmacologically active peptides," Endeavour, 1988, 12(2):60-65.

Hoffman et al., "Aminoglycoside antibiotics induce bacterial biofilm formation," Nature, 2005, 436(7054):1171-1175.

Hoiby et al., "Pseudomonas aeruginosa and the in vitro and in vivo biofilm mode of growth," Microbes Infect, 2001 3(1):23-35.

Imamura et al., "Fusarium and Candida albicans biofilms on soft contact lenses: model development, influence of lens type, and susceptibility to lens care solutions," Antimicrob Agents Chemother, 2008, 52(1):171-182.

Izano et al., "Differential roles of poly-Nacetylglucosamine surface polysaccharide and extracellular DNA in Staphylococcus aureus and Staphylococcus epidermidis biofilms," Appl Environ Microbiol, 2008, 74:470-476.

James et al., "Biofilms in chronic wounds," Wound Repair Regen, 2008, 16:37-44.

Jander et al., "Positive correlation between virulence of Pseudomonas aeruginosa mutants in mice and insects," J Bacteriol, 2000, 182(13):3843-3845.

Johansson et al., "Conformation-dependent antibacterial activity of the naturally occurring human peptide LL-37," J Biol Chem, 1998, 273(6):3718-3724.

Kaneko et al., "The transition metal gallium disrupts Pseudomonas aeruginosa iron metabolism and has antimicrobial and antibiofilm activity," J Clin Invest, 2007, 117(4):877-888.

(56) References Cited

OTHER PUBLICATIONS

Karatan and Watnick, "Signals, regulatory networks, and materials that build and break bacterial biofilms," Microbiol Mol Biol Rev, 2009, 73:310347.

Klevens et al., "Invasive methicillin-resistant *Staphylococcus aureus* infections in the United States," Jama, 2007, 298:1763-1771.

Knobloch et al., "Evaluation of different detection methods of biofilm formation in *Staphylococcus aureus*," Med Microbiol Immunol, 2002, 191:101-106.

Lear and Lewis (eds.) Microbial Biofilms: Current Research and Applications, Caister Academic Press, 2012, 4 pages, title pages and table of contents only.

Lee and Lee, "Structure-antimicrobial activity relationship between pleurocidin and its enantiomer," Exp Mol Med, 2008, 40(4):370-376.

Lee et al., "Solution structure of termite-derived antimicrobial peptide, spinigerin, as determined in SDS micelle by NMR spectroscopy," Biochem Biophys Res Commun, 2003, 309:591-597.

Leid et al., "Human leukocytes adhere to, penetrate, and respond to *Staphylococcus aureus* biofilms," Infect Immun, 2002, 70:6339-6345.

Leszczynska et al., "Potential of ceragenin CSA-13 and its mixture with pluronic F-127 as treatment of topical bacterial infections," J Appl Microbiol, 2010, 1:229-38.

Levy and Marshall, "Antibacterial resistance worldwide: causes, challenges and responses," Nat Med, 2004, 10(12 Suppl.):S122-129.

Lewis, "Riddle of biofilm resistance," Antimicrob Agents Chemother, 2001, 45(4):999-1007.

Lopez-Leban et al., "Molecular mechanisms of RIP, an effective inhibitor of chronic infections," Int J Artif Organs, 2010, 33:582-589.

Lowy, "*Staphylococcus aureus* infections," N Engl J Med, 1998, 339:520-532.

Maher and McClean, "Investigation of the cytotoxicity of eukaryotic and prokaryotic antimicrobial peptides in intestinal epithelial cells in vitro," Biochem Pharmacol, 2006, 71(9):1289-1298.

May et al., "Induction of multidrug resistance mechanism in *Escherichia coli* biofilms by interplay between tetracycline and ampicillin resistance genes," Antimicrob Agents Chemother, 2009, 53(11):4628-39.

Menzies and Kenoyer, "*Staphylococcus aureus* infection of epidermal keratinocytes promotes expression of innate antimicrobial peptides," Infect Immun, 2005, 73:5241-5244.

Mookherjee et al, "Intracellular receptor for human host defense peptide LL-37 in monocytes," J Immunol, 2009, 183:2688-2696.

Moser et al., "beta-Defensin1 contributes to pulmonary innate immunity in mice," Infect Immun, 2002, 70(6):3068-3072.

Murga et al., "Role of biofilms in the survival of Legionella pneumophila in a model potable-water system," Micro Biol, 2001, 147(Pt 11):3121-3126.

Murray, "Infectious disease complications of combat-related injuries," Crit Care Med, 2008, 36(7 Suppl):S358-364.

Niyonsaba et al., "Antimicrobial peptides human beta-defensins and cathelicidin LL-37 induce the secretion of a pruritogenic cytokine IL-31 by human mast cells," J Immunol, 2010, 184:3526-3534.

Nizet et al., "Innate antimicrobial peptide protects the skin from invasive bacterial infection," Nature, 2001, 414(6862):454-457.

Norrby et al., "Lack of development of new antimicrobial drugs: a potential serious threat to public health," Lancet Infect Dis, 2005, 5(2): 115-119.

Oldak and Trafny, "Secretion of proteases by Pseudomonas aeruginosa biofilms exposed to ciprofloxacin," Antimicrob Agents Chemother, 2005, 49(8):3281-3288.

O'Toole and Koller, "Flagellar and twitching motility are necessary for Pseudomonas aeruginosa biofilm development," Mol Microbiol, 1998, 30(2):295-304.

Ouhara et al., "Increased resistance to cationic antimicrobial peptide LL-37 in methicillin-resistant strains of *Staphylococcus aureus*," J Antimicrob Chemother, 2008, 61:1266-1269.

Overhage et al., "Human host defense peptide LL-37 prevents bacterial biofilm formation," Infect Immun, 2008, 76:4176-4182.

Papanastasiou et al., "Role of acetylation and charge in antimicrobial peptides based on human beta-defensin-3," Apmis, 2009, 117:492-499.

Park et al., "Helix stability confers salt resistance upon helical antimicrobial peptides," J Biol Chem, 2004, 279:13896-13901.

Parsek and Singh, "Bacterial biofilms: an emerging link to disease pathogenesis," Ann Rev Microbiol, 2003, 57:677-701.

Patel, "Biofilms and antimicrobial resistance," Clin Orthop Relat Res, 2005, (437):41-47.

Perez-Iratxeta and Andrade-Navarro, "K2D2: estimation of protein secondary structure from circular dichroism spectra," BMC Struct Biol, 2008, 8:25.

Picioreanu et al., "Microbial motility involvement in biofilm structure formation—a 3D modelling study," Water Sci Technol, 2007, 55(8-9):337-343.

Pollard et al., "Activities of Ceragenin CSA-13 Against Established Biofilms in an In Vitro Model of Catheter Decolonization," Anti-Infective Agents Med Chem, 2009, 8:290-294.

Prince "Biofilms, antimicrobial resistance, and airway infection," N Engl J Med, 2002, 347(14):1110-1111.

Rachid et al., "Effect of subinhibitory antibiotic concentrations on polysaccharide intercellular adhesin expression in biofilm-forming *Staphylococcus epidermidis*," Antimicrob Agents Chemother, 2000, 44(12):3357-3363.

Rello et al., "Impact of previous antimicrobial therapy on the etiology and outcome of ventilator-associated pneumonia," Chest, 1993,104(4):1230-1235.

Ressner et al., "Outcomes of bacteremia in burn patients involved in combat operations overseas," J Am Coll Surg, 2008, 206(3):439-444.

Richards et al., "Nosocomial infections in medical intensive care units in the United States National Nosocomial Infections Surveillance System," Crit Care Med, 1999, 27(5):887-892.

Rogers, Molecular Oral Microbiology, Caister Academic Press, 2008, pp. 65-108.

Ryadnov et al., "A new synthetic all-D-peptide with high bacterial and low mammalian cytotoxicity," Peptides, 2002, 23(10):1869-1871.

Saiman et al., "Cathelicidin peptides inhibit multiply antibiotic-resistant pathogens from patients with cystic fibrosis," Antimicrob Agents Chemother, 2001, 45(10):2838-2844.

Shai, "Mode of action of membrane active antimicrobial peptides," Biopolymers, 2002, 66(4):236-248.

Si et al., "Soluble expression of active human beta-defensin-3 in *Escherichia coli* and its effects on the growth of host cells," Chin Med J (Engl), 2007, 120:708-713.

Sieprawska-Lupa et al., "Degradation of human antimicrobial peptide LL-37 by *Staphylococcus aureus*-derived proteinases," Antimicrob Agents Chemother, 2004, 48(12):4673-4679.

Singh et al., "A component of innate immunity prevents bacterial biofilm development," Nature, 2002, 417(6888):552-555.

Sorensen et al., "An ELISA for hCAP-18, the cathelicidin present in human neutrophils and plasma," J Immunol Methods, 1997, 206:53-59.

Stewart et al., "Biofilm penetration and disinfection efficacy of alkaline hypochlorite and chlorosulfamates," J Appl Microbiol, 2001, 91(3):525-532.

Tack et al., "SMAP-29 has two LPS binding sites and a central hinge," Eur J Biochem, 2002, 269:1181-1189.

Tenover, "Mechanisms of antimicrobial resistance in bacteria," Am J Infect Control, 2006, 34(5 Suppl. 1):S3-10 and S64-873.

Tjabringa et al., "The antimicrobial peptide LL-37 activates innate immunity at the airway epithelial surface by transactivation of the epidermal growth factor receptor," J Immunol, 2003, 171:6690-6696.

Tokumaru et al., "Induction of keratinocyte migration via transactivation of the epidermal growth factor receptor by the antimicrobial peptide LL-37," J Immunol, 2005, 175:4662-4668.

Tomasinsig et al., "The human cathelicidin LL-37 modulates the activities of the P2X7 receptor in a structure-dependent manner," J Biol Chem, 2008, 283:30471-30481.

(56) References Cited

OTHER PUBLICATIONS

Toniolo et al., "Circular Dichroism Spectrum of a Peptide $3_{10}$-Helix," J Am Chem Soc, 1996, 118(11):2744-2745.
Tossi et al., "Amphipathic, alpha-helical antimicrobial peptides," Biopolymers, 2000, 55(1):4-30.
Travis et al., "Bactericidal activity of mammalian cathelicidin-derived peptides," Infect Immun, 2000, 68:2748-2755.
Turner et al., "Activities of LL-37, a cathelin-associated antimicrobial peptide of human neutrophils," Antimicrob Agents Chemother, 1998, 42:2206-2214.
Vad et al., "Divorcing folding from function: How acylation affects the membrane-perturbing properties of an antimicrobial peptide," Biochim Biophys Acta, 2010, 1804(4):806-820 (Epub Dec. 2009).
Van Delden and Iglewski, "Cell-to-cell signaling and Pseudomonas aeruginosa infections," Emerg Infect Dis, 1998, 4(4):551-560.
van 't Hof et al., "Antimicrobial peptides: properties and applicability," Biol Chem, 2001, 382(4):597-619.
Vunnam et al., "Synthesis and study of normal, enantio, retro, and retroenantio isomers of cecropin A-melittin hybrids, their end group effects and selective enzyme inactivation," J Pept Res, 1998, 51(1):38-44.
Wade et al., "All-D amino acid-containing channel-forming antibiotic peptides," Proc Natl Acad Sci USA, 1990, 87:4761-4765.
Wang et al., "Snake cathelicidin from Bungarus fasciatus is a potent peptide antibiotics," PLoS One, 2008, 3:e3217, 9 pages.
Wang, "Structures of human host defense cathelicidin LL-37 and its smallest antimicrobial peptide KR-12 in lipid micelles," J Biol Chem, 2008, 283(47):32637-32643.
Whatley et al., "Systemic absorption of gentamicin nasal irrigations," Am J Rhinol, 2006, 20(3):251-254.
Whitchurch et al., "Characterisation of a Pseudomonas aeruginosa twitching motility gene and evidence for a specialised protein export system widespread in eubacteria," Gene, 1991, 101(1):33-44.
Wilson et al., "Regulation of intestinal α-defensin activation by the metalloproteinase matrilysin in innate host defense," Science, 1999, 286(5437):113-117.
Wolcott et al., "Chronic wounds and the medical biofilm paradigm," J Wound Care, 2010, 19:45-46, 48-50, 52-43.
Yang et al., "Participation of mammalian defensins and cathelicidins in anti-microbial immunity: receptors and activities of human defensins and cathelicidin (LL-37)," J Leukoc Biol, 2001, 69:691-697.
Yao et al., "Conformational Transformation Exhibited by the Peptide Extracted from Crystalline Region of Bombyx mon Silk Fibroin in Solid and Solution States," Chinese J Chem, 2006, 24(5):705-710.
Yasin et al., "Theta defensins protect cells from infection by herpes simplex virus by inhibiting viral adhesion and entry," J Virol, 2004, 78(10):5147-5156.
Yeaman and Yount, "Mechanisms of antimicrobial peptide action and resistance," Pharmacol Rev, 2003, 55:27-55.
Zasloff, "Antimicrobial peptides of multicellular organisms," Nature, 2002, 415:389-395.
Zhu and Shin, "Antimicrobial and cytolytic activities and plausible mode of bactericidal action of the cell penetrating peptide penetratin and its Lys-linked two-stranded peptide," Chem Biol Drug Des, 2009, 73(2):209-15.

* cited by examiner

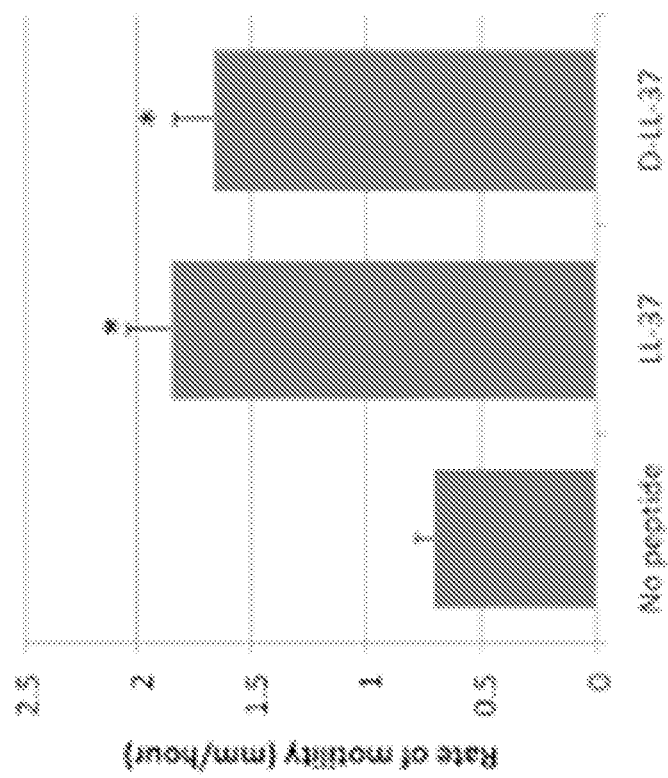

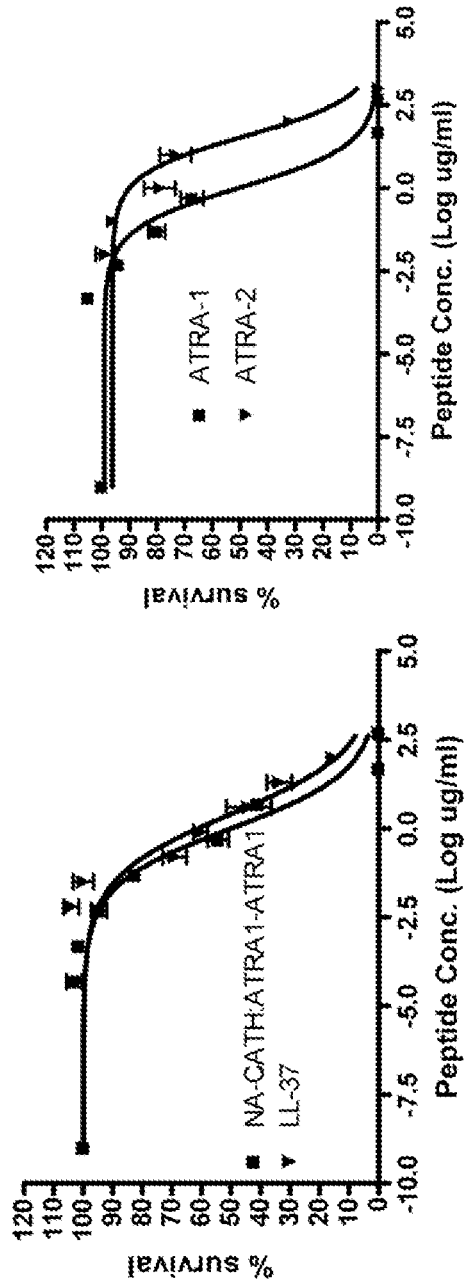

US 10,174,081 B2

ANTIMICROBIAL PEPTIDES AND USES THEREFORE

CROSS-REFERENCE TO RELATED APPLICATIONS

This application is a National Stage application under 35 U.S.C. § 371 of International Application No. PCT/US2012/034529 having an International Filing Date of Apr. 20, 2012, which claims priority from U.S. Provisional Application Ser. No. 61/477,874, filed Apr. 21, 2011, U.S. Provisional Application Ser. No. 61/556,988, filed Nov. 8, 2011, U.S. Provisional Application Ser. No. 61/556,983, filed Nov. 8, 2011, U.S. Provisional Application Ser. No. 61/556,993, filed Nov. 8, 2011, and U.S. Provisional Application Ser. No. 61/635,589, filed Apr. 19, 2012, each of which is incorporated herein by reference in its entirety.

STATEMENT AS TO FEDERALLY SPONSORED RESEARCH

This invention was made with government support under grant no. DE-FC52-04NA25455, awarded by the Department of Energy. The government has certain rights in the invention.

TECHNICAL FIELD

This invention relates to materials and methods for making and using cationic anti-microbial peptides (CAMPs).

BACKGROUND

Before the discovery of antibiotics, community-acquired infections were a major threat to people's health and welfare. Such infections continue to be a major problem, however. Soon after the discovery of penicillin and widespread access to antibiotics in the 1940's, bacteria began to develop varied degrees of resistance to these drugs. While new drugs have been introduced since the discovery of penicillin, the majority of them are the result of varied combinations of substituents on one of nine molecular scaffolds (Barrett et al. (2003) *Curr. Opin. Biotechnol.*, 14(6):621-626). Only two new classes of antibiotics have been introduced over the last thirty years, and only one of those, oxazolidinones, employs a novel anti-microbial mechanism (Norrby et al. (2005) *Lancet Infect. Dis.*, 5(2): 115-119). Therefore, it is hardly surprising that the number of microbes developing resistance is growing rapidly, and their resistance mechanisms are becoming more sophisticated (Tenover (2006) *Am. J. Infect. Control,* 34(5 Suppl. 1):S3-10 and S64-873). Antibiotic resistance initially was a problem associated with nosocomial infections, but occurrences of community-acquired cases are on the increase. Antibiotic resistance threatens the utility of "last resort" drugs such as vancomycin, the drug of choice for treating methicilin- and multidrug-resistant *Staphylococcus aureus* infections (Levy and Marshall (2004) *Nat. Med.,* 10(12 Suppl.):S122-129). Accordingly, there is urgent need for new antibiotics and therapeutic strategies for combating infections, especially those involving pathogens that are multidrug resistant.

SUMMARY

Materials and methods for leveraging the therapeutic potential of cationic anti-microbial peptides (CAMPs) are described herein. The CAMPs and compositions containing the CAMPs can be highly effective against microbial infections and biofilm formation.

In a first aspect, this document features a purified peptide having a length of about ten to about twenty amino acids, where the peptide includes (a) the amino acid sequence set forth in SEQ ID NO:3; (b) the amino acid sequence set forth in SEQ ID NO:3 with one substitution, addition, or deletion; (c) the amino acid sequence set forth in SEQ ID NO:4; (d) the amino acid sequence set forth in SEQ ID NO:4 with one substitution, addition, or deletion; (e) the amino acids sequence set forth in SEQ ID NO:8; or (f) the amino acid sequence set forth in SEQ ID NO:8 with one substitution, addition, or deletion. The peptide can contain D-amino acids. For example, at least 50 percent of the amino acids in the peptide can be D-amino acids. In some embodiments, the peptide can consist of D-amino acids.

In another aspect, this document features a purified peptide containing the amino acid sequence set forth in SEQ ID NO:5, or the amino acid sequence set forth in SEQ ID NO:5 with one or two substitutions, additions, or deletions. The peptide can contain D-amino acids (e.g., at least 50 percent D-amino acids). The peptide can consist of D-amino acids.

In another aspect, this document features a composition containing an excipient and a peptide as described herein (e.g., a peptide containing (a) the amino acid sequence set forth in SEQ ID NO:3; (b) the amino acid sequence set forth in SEQ ID NO:3 with one substitution, addition, or deletion; (c) the amino acid sequence set forth in SEQ ID NO:4; (d) the amino acid sequence set forth in SEQ ID NO:4 with one substitution, addition, or deletion; (e) the amino acids sequence set forth in SEQ ID NO:8; or (f) the amino acid sequence set forth in SEQ ID NO:8 with one substitution, addition, or deletion). The peptide can contain or consist of D-amino acids. The composition can contain about 0.01 µg/ml to about 10 µg/ml peptide, or about 0.05 µg/ml to about 25 µg/ml peptide. The composition can include a molecular crowding agent (e.g., a neutral, highly branched, high-mass, hydrophilic polysaccharide).

In another aspect, this document features a composition containing an excipient, a first peptide as described herein, and a second peptide as described herein, wherein the first and second peptides have different amino acid sequences or different ratios of L- and D-amino acids. The composition can contain about 0.01 µg/ml to about 10 µg/ml of the first peptide and about 0.01 µg/ml to about 10 µg/ml of the second peptide, or about 0.05 µg/ml to about 25 µg/ml of the first peptide and about 0.05 µg/ml to about 25 µg/ml of the second peptide. The composition can include a molecular crowding agent (e.g., a neutral, highly branched, high-mass, hydrophilic polysaccharide).

In still another aspect, this document features a method for treating an infection by microbial organism. The method can include contacting the microbial organism with a composition containing a peptide as described herein (e.g., a peptide containing (a) the amino acid sequence set forth in SEQ ID NO:3; (b) the amino acid sequence set forth in SEQ ID NO:3 with one substitution, addition, or deletion; (c) the amino acid sequence set forth in SEQ ID NO:4; (d) the amino acid sequence set forth in SEQ ID NO:4 with one substitution, addition, or deletion; (e) the amino acids sequence set forth in SEQ ID NO:8; or (f) the amino acid sequence set forth in SEQ ID NO:8 with one substitution, addition, or deletion, where the peptide optionally can contain or consist of D-amino acids). The composition can include a molecular crowding agent. The microbial organism can be a bacteria or a fungus. The composition can contain about 0.01 µg/ml to about 10 µg/ml peptide, or about 0.05 µg/ml to about 25 µg/ml peptide. After the contacting, growth of the microbial organism can be reduced by at least about 25 percent or at least about 50 percent when measured in an assay to measure colony formation.

This document also features a method for treating an infection by microbial organism, where the method can include contacting the microbial organism with a composition containing an excipient, a first peptide as described herein, and a second peptide as described herein, wherein the first and second peptides have different amino acid sequences or different ratios of L- and D-amino acids. The microbial organism can be a bacteria or a fungus. The composition can contain about 0.01 µg/ml to about 10 µg/ml peptide, or about 0.05 µg/ml to about 25 µg/ml peptide. After the contacting, growth of the microbial organism can be reduced by at least about 25 percent or at least about 50 percent when measured in an assay to measure colony formation.

In another aspect, this document features a method for inhibiting the growth of a biofilm on a surface. The method can include contacting the surface with a composition containing a peptide as described herein (e.g., a peptide containing (a) the amino acid sequence set forth in SEQ ID NO:3; (b) the amino acid sequence set forth in SEQ ID NO:3 with one substitution, addition, or deletion; (c) the amino acid sequence set forth in SEQ ID NO:4; (d) the amino acid sequence set forth in SEQ ID NO:4 with one substitution, addition, or deletion; (e) the amino acids sequence set forth in SEQ ID NO:8; or (f) the amino acid sequence set forth in SEQ ID NO:8 with one substitution, addition, or deletion, where the peptide optionally can contain or consist of D-amino acids). The composition can include a molecular crowding agent. The surface can be an environmental surface, or can be a surface in a living organism. After the contacting, growth of the biofilm can be reduced by at least about 25 percent or at least about 50 percent when measured in an assay to measure optical density.

In another aspect, this document features a method for inhibiting the growth of a biofilm on a surface, where the method includes contacting the surface with a composition containing an excipient, a first peptide as described herein, and a second peptide as described herein, wherein the first and second peptides have different amino acid sequences or different ratios of L- and D-amino acids. The surface can be an environmental surface, or can be a surface in a living organism. After the contacting, growth of the biofilm can be reduced by at least about 25 percent or at least 50 percent when measured in an assay to measure optical density.

In another aspect, this document features an article of manufacture containing a peptide as described herein (e.g., a peptide containing (a) the amino acid sequence set forth in SEQ ID NO:3; (b) the amino acid sequence set forth in SEQ ID NO:3 with one substitution, addition, or deletion; (c) the amino acid sequence set forth in SEQ ID NO:4; (d) the amino acid sequence set forth in SEQ ID NO:4 with one substitution, addition, or deletion; (e) the amino acids sequence set forth in SEQ ID NO:8; or (f) the amino acid sequence set forth in SEQ ID NO:8 with one substitution, addition, or deletion, where the peptide optionally can contain or consist of D-amino acids). The article of manufacture can be a personal hygiene product or a wound dressing.

In yet another aspect, this document features a method for treating an infection in a subject in need thereof. The method can include determining whether the subject is resistant to one or more conventional antibiotics, or is suspected of being resistant to one or more conventional antibiotics; and if it is determined that the subject is resistant or suspected of being resistant to the one or more conventional antibiotics, treating the subject with a composition containing a peptide as described herein, and if it is determined that the subject is not resistant to or suspected of being resistant to the one or more conventional antibiotics, treating the subject with the one or more conventional antibiotics. The method can further include monitoring the subject to determine whether the subject responds to the treatment and, if the subject is treated with the one or more conventional antibiotics but is determined or suspected to be resistant to the one or more conventional antibiotics, treating the subject with a composition containing a peptide as described herein.

In another aspect, this document features a method for treating an infection in a subject in need thereof. The method can include determining whether the subject is resistant to one or more conventional antibiotics, or is suspected of being resistant to one or more conventional antibiotics; and if it is determined that the subject is resistant or suspected of being resistant to the one or more conventional antibiotics, treating the subject with a composition containing an excipient, a first peptide as described herein, and a second peptide as described herein, wherein the first and second peptides have different amino acid sequences or different ratios of L- and D-amino acids, and if it is determined that the subject is not resistant to or suspected of being resistant to the one or more conventional antibiotics, treating the subject with the one or more conventional antibiotics. The method can further include monitoring the subject to determine whether the subject responds to the treatment and, if the subject is treated with the one or more conventional antibiotics but is determined or suspected to be resistant to the one or more conventional antibiotics, treating the subject with the composition containing the excipient and the first and second peptides.

This document also features a method for improving the effectiveness of treatment for a microbial infection in a subject in need thereof. The method can include (a) administering to the subject (i) an amount of a peptide as described herein that is sub-anti-microbial but is effective to reduce biofilm levels or inhibit biofilm formation, or (ii) administering a peptide as described herein under conditions that are sub-anti-microbial but are effective to reduce biofilm levels or inhibit biofilm formation; and (b) then administering to the subject (i) an anti-microbial amount of the peptide, or (ii) the peptide under conditions that are anti-microbial, or (iii) one or more conventional antibiotics. In step (a) of the method, the peptide can be administered under high salt conditions (e.g., conditions that include 125 to 150 mM salt).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1a, peptides NACATH (EC50=0.52 µg/ml) and LL-37 (EC50=0.74 µg/ml). FIG. 1b, peptides NACATH:ATRA1-ATRA1 (EC50=0.37 µg/ml) and NA-CATH (EC50=0.52 µg/ml). FIG. 1c, peptides NA-CATH:ATRA1-ATRA1 (EC50=0.37 µg/ml) and LL-37 (EC50=0.47 µg/ml). FIG. 1d, peptides ATRA=1 (EC50=0.64 µg/ml) and ATRA-2 (EC50=62.8 µg/ml). FIG. 1e, peptides DLL-37 (EC50=0.72 µg/ml) and LL-37 (EC50=0.47 µg/ml). FIG. 1f, peptides LL-37, D-LL-37, NA-CATH:ATRA1-ATRA1 were incubated with *P. aeruginosa* at the EC50 (0.47 µg/ml, 0.72 µg/ml, and 0.37 µg/ml, respectively). Killing kinetics assays were plated in triplicate time points over 3 hours.

FIGS. 2a-2e are a series of graphs showing that D- and L-LL-37 inhibit biofilm formation and stimulate twitching motility in *P. aeruginosa*. FIGS. 2a-2c show percent biofilm production in the presence of peptides L-LL-37 (FIG. 2a), D-LL-37 (FIG. 2c), and scrambled LL-37, NA-CATH, NA-CATH:ATRA1-ATRA1 and mCRAMP (FIG. 2b). Growth (absorbance at 600 nm) is indicated by gray bars, with "0 peptide" control set to 100%. Percent biofilm production is indicated by black bars (n=6), relative to "0 peptide" control. Each experiment is a representative of at least two independent trials. Error bars indicate the standard deviation from the mean. * indicates statistically significant differences from the positive control (p<0.01). FIGS. 2d and 2e show that D- and L-LL-37 increased the rate of twitching motility in *P. aeruginosa*. Motility was measured at various time points. Plates were inoculated with D-LL-37, L-LL-37, or controls (n=30) using a needle, and diameters were recorded.

FIGS. 5a-5f are a series of graphs plotting the effectiveness of anti-microbial peptides against *S. aureus*. Percent survival was calculated by counting CFUs after 3 hour incubations with various peptide concentrations. The EC50 is reported±the standard deviation. FIG. 5a shows survival after treatment with NA-CATH or LL-37. The EC50 for NA-CATH was 5.7±1.5 µg/ml, and the EC50 for LL-37 was 2.6±1.7 µg/ml. FIG. 5b shows survival after treatment with NA-CATH:ATRA1-ATRA1 or NA-CATH. The EC50 for NA-CATH:ATRA1-ATRA1 was 1.0±1.4 µg/ml, and the EC50 for NA-CATH was 5.7±1.5 µg/ml. FIG. 5c shows survival after treatment with NA-CATH:ATRA1-ATRA1 or LL-37. The EC50s were 1.0±1.4 µg/ml for NA-CATH:ATRA1-ATRA1 and 2.6±1.7 µg/ml for LL-37. FIG. 5d shows survival after treatment with ATRA-1 or ATRA-2. The EC50s were 1.1±1.5 µg/ml for ATRA-1 and 37±1.6 µg/ml for ATRA-2. FIG. 5e shows survival after treatment with LL-37 or D-LL-37. The EC50s were 26±1.4 µg/ml for D-LL-37 and 2.6±1.7 µg/ml for LL-37. FIG. 5f shows survival after treatment with ATRA-1 or ATRA-1A. The EC50 for ATRA-1 was 1.5±1.5 µg/ml, and the EC50 for ATRA-1A was 1.1±1.5 µg/ml. Curves were fit to the data, and R2 values were as follows: 0.97 for NA-CATH:ATRA1-ATRA1; 0.98 for NA-CATH; 0.95 for LL-37; 0.95 for D-LL-37; 0.98 for ATRA-1; 0.96 for ATRA-2; and 0.96 for ATRA-1A.

FIG. 6a shows inhibition of *S. aureus* biofilm formation by NA-CATH. FIG. 6b shows inhibition of *S. aureus* biofilm formation by NA-CATH:ATRA1-ATRA1. FIG. 6c shows inhibition of *S. aureus* biofilm formation by LL-37. FIG. 6d shows inhibition of *S. aureus* biofilm formation by D-LL-37. FIG. 6e shows inhibition of *S. aureus* biofilm formation by scrambled LL-37.

DETAILED DESCRIPTION

Figure 1:
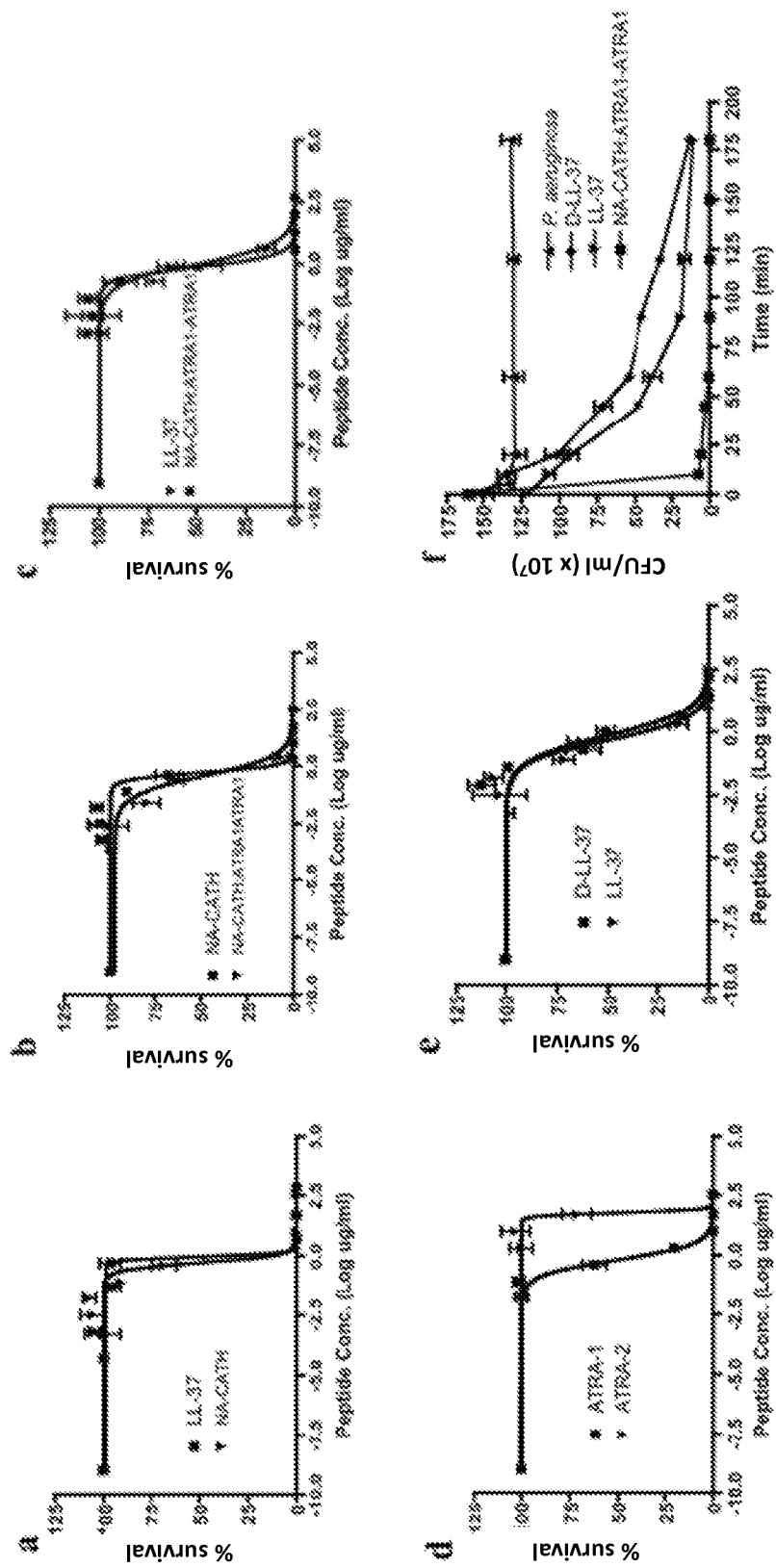
FIGS. 1a-1f are a series of graphs plotting the effectiveness of various anti-microbial peptides against *Pseudomonas aeruginosa*. Percent (%) survival was calculated by counting colony forming units (CFUs) after 3 hour incubations with peptides at various concentrations.

This document provides materials and methods related to developing novel strategies for leveraging the therapeutic potential of CAMPs. CAMPs as described herein, and compositions containing the CAMPs, can be used to treat or inhibit microbial infections, and to prevent or reduce biofilm formation.

Biofilms are aggregates of microorganisms in which cells adhere to each other on a surface. The adherent cells frequently are embedded in a self-produced matrix of extracellular polymeric substance (EPS) that generally is composed of extracellular DNA, proteins, and polysaccharides. Biofilms are ubiquitous, and can form on virtually any non-shedding, living or non-living surface in a non-sterile aqueous (or very humid) environment. Biofilms can be found, for example, in natural, industrial and hospital settings (Hall-Stoodley et al. (2004) Nat. Rev. Microbiol. 2(2):95-108; and Lear and Lewis (eds.) (2012) Microbial Biofilms: Current Research and Applications, Caister Academic Press). Biofilms can be involved in a wide variety of microbial infections in the body ("Research on microbial biofilms (PA-03-047)," NIH, National Heart, Lung, and Blood Institute, 2002), including common problems such as urinary tract infections, catheter infections, ear infections, formation of dental plaque, gingivitis, coating contact lenses, and less common but more serious conditions such as endocarditis, infections in cystic fibrosis, and infections of permanent indwelling devices such as joint prostheses and heart valves (Rogers (2008) Molecular Oral Microbiology, Caister Academic Press, pp. 65-108; Imamura et al. (2008) Antimicrob. Agents Chemother. 52(1):171-182; Lewis (2001) Antimicrob. Agents Chemother. 45(4):999-1007; and Parsek and Singh (2003) Ann. Rev. Microbiol. 57:677-701). Bacterial biofilms also can impair cutaneous wound healing and reduce topical antibacterial efficiency in healing or treating infected skin wounds (Davis et al. (2008) Wound Repair and Regeneration 16(1):23-29).

Chronic opportunistic infections in immunocompromised patients and the aging population are a major challenge for medical professionals, as traditional antibiotic therapies usually are not sufficient to eradicate the infections. One reason for their persistence seems to be the capability of the bacteria to grow within biofilms that protect them from adverse environmental factors. Pseudomonas aeruginosa is an example of an opportunistic pathogen and a causative agent of emerging nosocomial infections. Other examples of microbes that can form medically relevant biofilms include, without limitation, Streptococcus mutans and Streptococcus sanguinis, which are involved in formation of dental plaque (Rogers, supra), Legionella bacteria (Murga et al. (2001) Microbiol. 147(Pt 11):3121-3126), and Neisseria gonorrhoeae, which can form biofilms on human cervical epithelial cells (Apicella et al. (2010) "Gonococcal Biofilms," in Neisseria: Molecular Mechanisms of Pathogenesis, Caister Academic Press, pp. 55-60).

The peptides and compositions described herein can be used for treatment of bacterial infections and biofilms, including infections and biofilms that involve microbial strains that are resistant to antibiotics. These peptides and compositions can have enhanced potency against pathogenic organisms, and can be used, without limitation, for treating infections, as sensors, in sterilization procedures, in surface coatings, in wound dressings, and in personal hygiene products such as mouthwash and body wash.

Anti-microbial Peptides

CAMPs are a defense mechanism pervasively employed by higher organisms to guard against infection. CAMPs can be loosely classified into four groups based on common structural themes: linear α-helical peptides, linear extended peptides with sequences dominated by one or more amino acids, peptides containing loop structures, and peptides with more defined structures constrained by intramolecular disulfide bonds (van't Hof et al. (2001) Biol. Chem., 382(4): 597-619). It is notable that despite their extensive use for millions of years, bacteria have failed to develop widespread resistance to CAMPs. This is in stark contrast with the rampant spread of bacterial resistance to conventional antibiotics that presently threatens the ability to effectively treat infections.

While CAMPs exhibit a diverse range of amino acid sequences and structural properties, they typically are small amphipathic peptides that are rich in lysine and arginine residues, and they exert a direct anti-microbial effect on a broad spectrum of microbes including Gram-positive and Gram-negative bacteria, and fungi. Although there is debate regarding the specific mechanisms employed by anti-microbial peptides and whether secondary targets are involved, CAMPs have been shown to attack bacterial membranes, ultimately disrupting their integrity (Brogden (2005) *Nat. Rev. Microbiol.*, 3(3):238-250). The cationic peptides are proposed to initially associate with the outer surface of bacterial membranes, which tend to contain a greater abundance of lipids with negatively charged head groups than do eukaryotic membranes. The presence of cholesterol in eukaryotic membranes also may contribute to their resistance to disruption by CAMPs. Multiple mechanisms for membrane disruption have been proposed, and these mechanisms appear to be peptide dependent. Proposed mechanisms range from a "barrel-stave" model in which where amphipathic helical peptides insert into the membrane to form helical bundle structures with large central pores, to a "carpet model" in which peptides gather and concentrate at the membrane surface to interact with anionic lipid head groups, causing distortions in the lipid bi-layer and formation of peptide-lined openings in the membrane.

Helical CAMP Enantiomers

Helical CAMPs are one of the most abundant classes of anti-microbial peptides (Tossi et al. (2000) *Biopolymers*, 55(1):4-30). They are short (typically less than 40 amino acids), which facilitates their synthesis, and they have a simple, linear, amphipathic α-helix structure, which makes them amenable to characterization by spectroscopic methods such as circular dichroism (CD). In the absence of the influence of negatively charged bacterial membranes, helical CAMPs assume a relatively unstructured random coil, and only adopt a helical conformation when they interact and bind bacterial membranes. Formation of an amphipathic helix by a peptide can facilitate its insertion and integration into microbial membranes, and usually is essential to the anti-microbial mechanism employed by helical CAMPs. Unfortunately, because helical CAMPs are small peptides that have little or no structure until they interact with bacterial membranes, they are susceptible to degradation by proteases, which could reduce their potential therapeutic utility. Assembling the peptides out of D-amino acids, which are not recognized by proteases, can enable CAMPs to evade digestion and remain intact until reaching the membrane (Wade et al. (1990) *Proc. Natl. Acad. Sci. USA*, 87(12): 4761-4765). Peptides formed from all L- or all D-amino acids form helical structures that differed only by their handedness, with L-CAMPs adopting a right-handed helical conformation and D-CAMPs forming a left-handed helix.

Early studies of the D-enantiomers of three naturally occurring anti-microbial peptides (cecropin A, magainin 2 amide and melittin) and two designed peptides (chimeric peptides combining portions of cecropin A and melittin) did not indicate any significant differences in the anti-microbial or hemolytic properties of the D- and L-isomers (Wade et al., supra). This led to the suggestion that the peptides exert their anti-microbial effect without significant involvement of chiral elements within the bacterial membranes. Later studies, however, found significant differences in the anti-microbial performance of the D- and L-isomers of the cecropin A/melittin chimeric peptides (Vunnam et al. (1998) *J. Pept. Res.*, 51(1):38-44), and attributed the superior anti-microbial potency of the D-isomers against *S. aureus* and *P. aeruginosa* at least in part to their resistance to degradation by microbial proteases. D- and L-enantiomers of pleurocidin, a helical CAMP from the winter flounder, also exhibited significant differences in their anti-microbial effectiveness against a panel of Gram-negative and Gram-positive bacteria (Lee and Lee (2008) *Exp. Mol. Med.*, 40(4):370-376). The D-isomer also displayed much lower hemolytic activity than the corresponding L-peptide.

As described herein, it was proposed that differences in the effectiveness evidenced by some cationic anti-microbial peptides are due at least in part to inherent structural properties of the peptides and their interactions with chiral elements of the lipid bi-layer. The experiments described below were conducted to investigate the role of chirality in the anti-microbial performance of L- and D-CAMPs through comprehensive biophysical and biochemical characterization of peptide interactions with chiral lipids. Factoring in membrane composition and headgroup charge allowed for identification of the physical and chemical features that make a CAMP effective against a specific type of membrane. This approach was novel because of its focus on the chirality of both the peptides and the lipid membrane components.

The properties that make anti-microbial peptides an effective defensive mechanism in higher organisms also can make them ideally suited as a platform for targeting microbes for delivery of anti-microbial compounds. This platform could provide a therapeutic tool for treating infections (e.g., infections of the gastrointestinal tract, respiratory system, circulatory system, lymphatic system, urinary system, muscular system, skeletal system, nervous system, or reproductive system), and could allow for the use of novel anti-microbial agents that otherwise would be unsuitable as therapeutics.

Some interior surfaces of the body, such as the respiratory and the gastrointestinal (GI) tracts, are topographically equivalent to exterior surfaces of the body. Because these surfaces are constantly exposed to potentially pathogenic microbes and are conducive to bacterial growth, novel therapeutic agents and strategies are needed for treating infections of the respiratory and GI tracts, particularly those caused by antibiotic resistant pathogenic microbes. Some agents, such as *Francisella tularensis, Bacillus anthracis,* and *Yersinia pestis*, are known to cause life-threatening pneumonic infections and may be rendered antibiotic resistant, and are of particular concern as potential biological weapons. Similarly, foodborne and waterborne pathogens such as *Shigella dysenteriae, Vibrio cholera,* and *Salmonella typhi* are considered potential biological threats that could be employed to contaminate food and/or water supplies. While infections by many of these microbes usually are responsive to treatment with antibiotics, illness resulting from intentional exposure would likely involve organisms that have been engineered to be resistant to conventional antibiotics.

As described herein, CAMPs may provide a solution to such problems. CAMPs provide an ideal model for the design of molecules that target many bacteria, both Gram-positive and Gram-negative. While there is debate regarding the specific anti-microbial mechanisms employed by CAMPs and the extent to which internal targets are involved, these peptides can attack and disrupt bacterial membranes. In targeting bacteria, CAMPs capitalize on a fundamental physical property of bacterial membranes—negative charge density. In some cases, CAMP-based therapeutics can selectively target a pathogen such that the peptide alone kills the microbe. Alternatively, CAMPs can be used as vehicles for targeted delivery of more potent anti-microbial agents. See, e.g., U.S. Publication No. 20100022750.

The peptides provided herein can have a length between about 10 amino acids and about 50 amino acids. For example, a peptide can have a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids. In some embodiments, a peptide can have a length of, without limitation, about 10 to about 15 amino acids, about 15 to about 20 amino acids, about 20 to about 25 amino acids, about 25 to about 30 amino acids, about 30 to about 35 amino acids, about 35 to about 40 amino acids, about 40 to about 45 amino acids, about 45 to about 50 amino acids, about 10 to about 20 amino acids, about 20 to about 30 amino acids, about 30 to about 40 amino acids, or about 40 to about 50 amino acids. In some cases, smaller peptides can be more useful than larger and/or more complex CAMPs, because smaller peptides are more easily synthesized and characterized.

In some embodiments, the sequence of a helical anti-microbial peptide can be based on the sequence of the 34-residue NA-CATH peptide, which corresponds to a helical cathelicidin identified in cDNA from the venom gland of the elapid snake, *Naja atra* (Zhao et al. (2008) *Peptides* 29(10):1685-1691) or portion of a sequence of a CAMP. NA-CATH has the sequence KRFKKFFKKLKNSVK KRAKKFFKKPKVIGVTFPF (SEQ ID NO:1), and includes two 11 amino acid repeats (underlined) that differ from one another at the third and tenth positions. The peptides provided herein can be shorter or variant versions of the NA-CATH peptide, such that they contain only one repeat or contain repeat sequences that are altered as compared to the wild type NA-CATH sequence. Exemplary peptides are described in the examples and tables below.

Methods for Making Peptides

The peptides provided herein can be produced by any of a number of methods, many of which are well known in the art. In some embodiments, a peptide can be obtained by extraction from a natural source (e.g., from isolated cells, tissues or bodily fluids), by expression of a recombinant nucleic acid encoding the peptide or by chemical synthesis (e.g., using solid phase peptide synthesis methods or a peptide synthesizer such as an ABI Peptide Synthesizer; Applied Biosystems; Foster City, Calif.). For example, standard recombinant technology using an expression vector encoding a peptide provided herein can be used. The resulting peptide then can be purified using, for example, affinity chromatographic techniques and HPLC. The extent of purification can be measured by any appropriate method, including but not limited to: column chromatography, polyacrylamide gel electrophoresis, or high-performance liquid chromatography. In some cases, a peptide can be designed or engineered to contain a tag sequence that allows the peptide to be purified (e.g., captured onto an affinity matrix). For example, a tag such as c-myc, hemagglutinin, polyhistidine, or FLAG™ tag (Kodak) can be used to aid peptide purification. Such tags can be inserted anywhere within the peptide, including at either the carboxyl or amino terminus. Other fusions that can be used include enzymes that aid in the detection of the peptide, such as alkaline phosphatase. In some embodiments, a peptide can be amidated at its carboxy terminus.

In some cases, a peptide provided herein can be purified. A "purified peptide" is a peptide that either has no naturally occurring counterpart (e.g., a peptidomimetic), or has been chemically synthesized and is thus uncontaminated by other peptides, or that has been separated or purified from other cellular components by which it is naturally accompanied (e.g., other cellular proteins, polynucleotides, or cellular components). Typically, a peptide is considered "purified" when it is at least 70%, by dry weight, free from the proteins and other molecules with which it naturally associates. A preparation of a purified peptide therefore can be, for example, at least 80%, at least 90%, or at least 99%, by dry weight, the peptide. Suitable methods for purifying peptides can include, for example, affinity chromatography, immunoprecipitation, size exclusion chromatography, and ion exchange chromatography. The extent of purification can be measured by any appropriate method, including but not limited to: column chromatography, polyacrylamide gel electrophoresis, or high-performance liquid chromatography.

Variants and Peptides with Altered Structures

Also provided herein are peptides that include one or more substitutions, deletions, or additions as compared with the sequences provided herein. For example, a peptide can have an amino acid sequence with one or more (e.g., one, two, three, four, five, or more than five) substitutions, additions, or deletions relative to the sequence set forth in any of SEQ ID NOS:1-14. In some embodiments, amino acid substitutions can be conservative amino acid substitutions. Conservative amino acid substitutions can be, for example, aspartic-glutamic as acidic amino acids; lysine/arginine/histidine as basic amino acids; leucine/isoleucine, methionine/valine, alanine/valine as hydrophobic amino acids; serine/glycine/alanine/threonine as hydrophilic amino acids. Conservative amino acid substitutions also include groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. After making an amino acid substitution, the activity of a peptide containing the amino acid substitution can be assessed using the assays described herein.

The term "amino acid" as used herein refers to natural amino acids, unnatural amino acids, and amino acid analogs, all in their D and L stereoisomers if their structures so allow. Natural amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. Unnatural amino acids include, without limitation, azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, 2,4-diaminoisobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, N-methylisoleucine, N-methylvaline, norvaline, norleucine, ornithine, and pipecolic acid.

An "analog" is a chemical compound that is structurally similar to another but differs slightly in composition (as in the replacement of one atom by an atom of a different element or in the presence of a particular functional group).

An "amino acid analog" therefore is structurally similar to a naturally occurring amino acid molecule as is typically found in native peptides, but differs in composition such that either the C-terminal carboxy group, the N-terminal amino group, or the side-chain functional group has been chemically modified to another functional group. Amino acid analogs include natural and unnatural amino acids that are chemically blocked, reversibly or irreversibly, or modified on their N-terminal amino group or their side-chain groups, and include, for example, methionine sulfoxide, methionine sulfone, S-(carboxymethyl)-cysteine, S-(carboxymethyl)-cysteine sulfoxide and S-(carboxymethyl)-cysteine sulfone. Amino acid analogs may be naturally occurring, or can be synthetically prepared. Non-limiting examples of amino acid analogs include 5-Hydroxytrpophan (5-HTP), aspartic acid-(beta-methyl ester), an analog of aspartic acid; N-ethylglycine, an analog of glycine; and alanine carboxamide, an analog of alanine Other examples of amino acids and amino acids analogs are listed in Gross and Meienhofer, *The Peptides: Analysis, Synthesis, Biology*, Academic Press, Inc., New York (1983).

The stereochemistry of a peptide can be described in terms of the topochemical arrangement of the side chains of the amino acid residues about the peptide backbone, which is defined by the peptide bonds between the amino acid residues and the α-carbon atoms of the bonded residues. In addition, polypeptide backbones have distinct termini and thus direction. The majority of naturally occurring amino acids are L-amino acids, and naturally occurring polypeptides are largely comprised of L-amino acids. D-amino acids are the enantiomers of L-amino acids. The peptides provided herein can be made up of L-amino acids, D-amino acids, or a combination thereof. For example, a peptide can have an amino acid composition in which at least 10% (e.g., at least 10%, at least 20%, at least 25%, at least 30%, at least 40%, at least 50%, at least 60%, at least 70%, at least 75%, at least 80%, at least 85%, at least 90%, at least 95%) of the amino acids are D-amino acids.

In some embodiments, peptidomimetic compounds can be used in place of the peptides provided herein. Peptidomimetic compounds are synthetic, non-peptide compounds having a three-dimensional conformation (i.e., a "peptide motif,") that is substantially the same as the three-dimensional conformation of a selected peptide, and can thus confer the same or similar function as the selected peptide. Peptidomimetic compounds can be designed to mimic any of the peptides described herein.

Peptidomimetic compounds that are protease resistant can be particularly useful. Further, peptidomimetic compounds may have additional characteristics that enhance therapeutic utility, such as increased cell permeability and prolonged biological half-life. Such compounds typically have a backbone that is partially or completely non-peptide, but with side groups that are identical or similar to the side groups of the amino acid residues that occur in the peptide upon which the peptidomimetic compound is based. Several types of chemical bonds (e.g., ester, thioester, thioamide, retroamide, reduced carbonyl, dimethylene and ketomethylene) are known in the art to be useful substitutes for peptide bonds in the construction of peptidomimetic compounds.

Testing Peptides for Anti-Microbial and Anti-Biofilm Activity

The anti-microbial and anti-biofilm activities of the peptides provided herein can be tested using any of a number of suitable methods, including those described in the Examples herein. The activity of a peptide against bacteria such as *E. coli*, for example, can be tested by incubating the bacteria in Luria Bertani broth at 37° C. until cells reach an $OD_{600}$ of 0.8 to 1.1. Cells then can be diluted to a suitable concentration (e.g., $10^6$ CFU/ml) in, for example, 10 mM sodium phosphate (pH 7.5) containing varying concentrations of peptide. Peptide concentrations used in the assays can range from 0 μg/ml to about 100 μg/ml with intermediate concentrations (e.g., about 0.01 μg/ml, 0.05 μg/ml, 0.1 μg/ml, 0.5 μg/ml, 1 μg/ml, 2.5 μg/ml, 5 μg/ml, 7.5 μg/ml, 10 μg/ml, 25 μg/ml, 50 μg/ml, 75 μg/ml, about 0.01 μg/ml to about 0.1 μg/ml, about 0.05 μg/ml to about 0.5 μg/ml, about 0.1 to about 1 μg/ml, about 0.5 μg/ml to about 5 μg/ml, about 2.5 μg/ml to about 10 μg/ml, or any other range between about 0.01 μg/ml and about 100 μg/ml) that vary for each peptide in order to maximize the number of data points. Assay cultures can be incubated at 37° C. for about two hours, and serial dilutions of each sample can be prepared and plated in triplicate onto Luria Bertani broth plates. The plates can be incubated at 37° C. overnight (~16 hours), and colonies can be counted the following morning.

Bacterial survival at each peptide concentration can be calculated according to the ratio of the number of colonies on the plates corresponding to the peptide concentration and the average number of colonies observed for assay cultures lacking peptide. The peptide concentration required to kill about 50% of the viable cells in the assay cultures (EC50) can be determined by plotting percent survival as a function of the log of peptide concentration (log μg/ml) and fitting the data to Equation (1) using, for example, GraphPad Prism (GraphPad Software, Inc., San Diego, Calif.), which describes a sigmoidal dose-response.

$$S = S_B + ((S_T - S_B)/(1 + 10^{(Log\ EC50 - X)H})) \tag{1}$$

In Equation (1), S is percent survival, $S_T$ and $S_B$ represent the upper and lower survival boundaries, X is the log of the peptide concentration, and H is the Hill slope of the transition region. Equation (1) is presented in different form in Example 1 below.

The effect of a peptide on biofilm production can be assessed by, for example, incubating a biofilm-forming bacteria or other microbe with varying concentrations of the peptide for a certain length of time (e.g., 24 hours at 37° C.). Optical density of the cultures (OD600 nm) can be measured to assess microbial growth, and cultures then can be stained with crystal violet to assess biofilm production. See, e.g., Durham-Colleran et al. (2010) *Microb. Ecol.*, 59(3):457-465.

Compositions

A peptide as provided herein can be formulated as a composition by admixture with one or more pharmaceutically acceptable, non-toxic excipients or carriers. Such compositions can be used to treat or prevent microbial infection, for example. In some embodiments, a composition can include one particular peptide, while in other embodiments a composition can include two or more different peptides (e.g., peptides having different sequences or different amounts of D- and L-amino acids). Excipients (also referred to as pharmaceutically acceptable carriers) can be liquid or solid, and can be selected with the planned manner of administration in mind so as to provide for the desired bulk, consistency, and other pertinent transport and chemical properties, when combined with one or more of peptides and any other components of a given composition. Common excipients include, without limitation, sterile water, saline, polyalkylene glycols such as polyethylene glycol, oils of vegetable origin, hydrogenated naphthalenes, binding agents (e.g., polyvinylpyrrolidone or hydroxypropyl methylcellulose), fillers (e.g., lactose and other sugars, gelatin, or calcium sulfate), lubricants (e.g., starch, polyethylene glycol, or sodium acetate), disintegrates (e.g., starch or sodium starch glycolate), and wetting agents (e.g., sodium lauryl sulfate). In some cases, biocompatible, biodegradable lactide polymer, lactide/glycolide copolymer, polyoxethylene-polyoxypropylene copolymers, or combinations thereof can be used as excipients for controlling the release of a peptide in vivo.

In some embodiments, a composition can include a peptide and one or more molecular crowding agents such as, by way of example and not limitation, FICOLL™ (e.g., FICOLL™ 70), polyethylene glycol (PEG), and dextran. FICOLL™ is a neutral, highly branched, high-mass, hydrophilic polysaccharide that dissolves readily in aqueous solutions. PEG is a polymer of ethylene oxide, and is commercially available over a wide range of molecular weights from 300 g/mol to 10,000,000 g/mol. Dextran is a complex, branched polysaccharide made of glucose molecules. Without being bound by a particular mechanism, such agents may help to mimic the natural cellular environment, which may enhance the activity of the peptide. Such agents can be included in the compositions in amounts from about 5% to about 50% wt/vol (e.g., about 5%, about 10%, about 15%, about 20%, about 25%, about 30%, about 35%, about 40%, about 45%, or about 50% wt/vol, or any range therebetween).

Compositions can be prepared for topical (e.g., transdermal, sublingual, ophthalmic, or intranasal) administration, parenteral administration (e.g., by subcutaneous, intrathecal, intraventricular, intramuscular, or intraperitoneal injection, or by intravenous drip, in the form of liquid solutions or suspensions in aqueous physiological buffer solutions), for oral administration (e.g., in the form of tablets or capsules), or for intranasal administration (e.g., in the form of powders, nasal drops, or aerosols), depending on whether local or systemic treatment is desired and on the area to be treated. Administration can be rapid (e.g., by injection) or can occur over a period of time (e.g., by slow infusion or administration of slow release formulations). Compositions for other routes of administration also can be prepared as desired using appropriate methods. In addition, compositions can be prepared for in vitro use (e.g., for use on environmental surfaces or on medical devices).

Formulations for topical administration of peptides include, for example, sterile and non-sterile aqueous solutions, non-aqueous solutions in common solvents such as alcohols, or solutions in liquid or solid oil bases. Such solutions also can contain buffers, diluents and other suitable additives. Pharmaceutical compositions and formulations for topical administration can include transdermal patches, ointments, lotions, creams, gels, drops, suppositories, sprays, liquids, and powders. Nasal sprays also can be useful, and can be administered by, for example, a nebulizer, an inhaler, or another nasal spray device. Conventional pharmaceutical carriers, aqueous, powder or oily bases, thickeners and the like may be useful.

Compositions and formulations for oral administration include, for example, powders or granules, suspensions or solutions in water or non-aqueous media, capsules, sachets, or tablets. Such compositions also can incorporate thickeners, flavoring agents, diluents, emulsifiers, dispersing aids, or binders.

Compositions and formulations for parenteral, intrathecal or intraventricular administration can include sterile aqueous solutions, which also can contain buffers, diluents and other suitable additives (e.g., penetration enhancers, carrier compounds and other pharmaceutically acceptable carriers).

Pharmaceutical compositions can include, but are not limited to, solutions, emulsions, aqueous suspensions, and liposome-containing formulations. These compositions can be generated from a variety of components that include, for example, preformed liquids, self-emulsifying solids and self-emulsifying semisolids. Emulsions are often biphasic systems comprising of two immiscible liquid phases intimately mixed and dispersed with each other; in general, emulsions are either of the water-in-oil (w/o) or oil-in-water (o/w) variety. Emulsion formulations can be useful for oral delivery of therapeutics due to their ease of formulation and efficacy of solubilization, absorption, and bioavailability.

Liposomes are vesicles that have a membrane formed from a lipophilic material and an aqueous interior that can contain the composition to be delivered. Liposomes can be particularly useful due to their specificity and the duration of action they offer from the standpoint of drug delivery. Liposome compositions can be formed, for example, from phosphatidylcholine, dimyristoyl phosphatidylcholine, dipalmitoyl phosphatidylcholine, dimyristoyl phosphatidylglycerol, or dioleoyl phosphatidylethanolamine. Numerous lipophilic agents are commercially available, including LIPOFECTIN® (Invitrogen/Life Technologies, Carlsbad, Calif.) and EFFECTENE™ (Qiagen, Valencia, Calif.).

The peptides provided herein further encompass pharmaceutically acceptable salts, esters, or salts of such esters, or any other compound which, upon administration to an animal including a human, is capable of providing (directly or indirectly) the biologically active metabolite or residue thereof. Accordingly, for example, provided herein are pharmaceutically acceptable salts of peptides, prodrugs and pharmaceutically acceptable salts of such prodrugs, and other bioequivalents. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of the peptides described herein (i.e., salts that retain the desired biological activity of the parent peptide without imparting undesired toxicological effects). Examples of pharmaceutically acceptable salts include, without limitation, salts formed with cations (e.g., sodium, potassium, calcium, or polyamines such as spermine), acid addition salts formed with inorganic acids (e.g., hydrochloric acid, hydrobromic acid, sulfuric acid, phosphoric acid, or nitric acid), and salts formed with organic acids (e.g., acetic acid, citric acid, oxalic acid, palmitic acid, or fumaric acid).

Compositions additionally can contain other adjunct components such as, for example, lubricants, preservatives, stabilizers, wetting agents, emulsifiers, salts for influencing osmotic pressure, buffers, colorings, flavorings, and aromatic substances. When added, however, such materials should not unduly interfere with the biological activities of the peptide components within the compositions provided herein. The formulations can be sterilized if desired.

Dosing of compositions for administration to a subject typically is dependent on the severity and responsiveness of the condition to be treated, with the course of treatment lasting from several days to several months, or until a cure is effected or a diminution of the condition is achieved. Persons of ordinary skill in the art routinely determine optimum dosages, dosing methodologies and repetition rates. Optimum dosages can vary depending on the relative potency of individual peptides, and can generally be estimated based on EC50 found to be effective in in vitro and in vivo animal models. Typically, dosage is from 0.01 µg to 100 g per kg of body weight, and may be given once or more daily, biweekly, weekly, monthly, or even less often. Following successful treatment, it may be desirable to have the patient undergo maintenance therapy to prevent the recurrence of the disease state.

It is noted that treatments may differ if the patient is resistant or suspected of being resistant to certain antibiotics. For example, if the patient has an infection that is resistant to antibiotics, the dose may be increased or the treatment may include two or more different peptides.

The peptides and compositions described herein also can be used in the manufacture of a medicament for treating a microbial infection or for inhibiting or reducing biofilm growth. Peptides can be admixed, encapsulated, conjugated or otherwise associated with other molecules, molecular structures, or mixtures of compounds such as, for example, liposomes, polyethylene glycol, receptor targeted molecules, or oral, topical or other formulations, for assisting in uptake, distribution, absorption, or activity.

Uses for Anti-Microbial Peptides

The peptides and compositions described herein can be used to inhibit microbial growth and to reduce or prevent biofilm formation. For example, a composition containing an anti-microbial, helical peptide as described herein can be used to treat a subject having a microbial (e.g., bacterial or fungal) infection. In some embodiments, a composition containing an anti-microbial, helical peptide can be used to inhibit or prevent biofilm growth, either in vivo be administration to a subject, or in vitro such as in a sterilization procedure for an environmental surface (e.g., in a hospital, a public restroom, or another public setting). The peptides and compositions described herein also can be used in surface coatings for medical devices (e.g., catheters and other indwelling devices), or in dressings to be applied to wounds on or in a patient. In some cases, the peptides provided herein can be formulated into compositions that serve as personal hygiene products, including mouthwash, hand sanitizer, or body wash.

The peptides and compositions also can be used in methods that include determining whether a subject having a microbial infection is resistant to one or more conventional antibiotics (e.g., methicillin), or is suspected of being resistant to one or more conventional antibiotics. If the subject is determined to be resistant to the one or more conventional antibiotics, or is suspected of being resistant to the one or more conventional antibiotics, s/he can be treated with a peptide or composition provided herein. In contrast, if the subject is determined not to be resistant to the one or more conventional antibiotics, or is not suspected of being resistant to the one or more conventional antibiotics, s/he can be treated with the one or more conventional antibiotics. In such methods, the subject can be monitored to determine whether the treatment is effective, and the treatment can be adjusted accordingly. For example, if the subject is treated with one or more conventional antibiotics but is subsequently determined to be resistant to the conventional antibiotic(s), the subject can be treated with a peptide or composition as provided herein.

In addition, the peptides and compositions provided herein can be used in methods for improving the effectiveness of treatment for microbial infection. For example, a method can include administering to a subject an amount of a peptide or composition that is sub-anti-microbial but is effective to reduce biofilm levels or inhibit biofilm formation, or administering a peptide under conditions that are sub-anti-microbial but are effective to reduce biofilm levels or inhibit biofilm formation. As described in the Examples below, for example, a peptide can be less effective as an anti-microbial agent under high salt conditions (e.g., about 125 to about 150 mM salt, including about 130 mM, about 135 mM, about 140 mM, or 145 mM salt), but can retain effectiveness as an anti-biofilm agent under such conditions. After one or more sub-anti-microbial treatments, the subject can be treated with an anti-microbial amount of the peptide or composition, with the peptide under conditions that are anti-microbial, or with one or more conventional antibiotics. The sub-anti-microbial and anti-microbial treatments can be separated by any length of time, ranging from an hour or less to several hours to a day or more (e.g., about 0.5 hour, about one hour, about two hours, about three hours, about four hours, about six hours, about 12 hours, about 1 day, or more than 1 day). Treatments can be repeated as needed or desired.

The effectiveness of a peptide or composition containing one or more peptides as described herein can be determined by assessing microbial growth or biofilm growth before, during, and/or after treatment. In some embodiments, for example, samples can be obtained from a subject before treatment, and at one or more different time points during or after treatment with a peptide or composition as provided herein, and microbial growth can be measured by counting the number of colonies that grow up from the samples after they are plated on a solid medium. Biofilm growth can be measured based on optical density (e.g., at 600 nm) and/or staining with crystal violet, for example. Treatment with a peptide or composition can be considered effective if microbial growth or biofilm formation is reduced by at least 5% (e.g., at least 10%, at least 20%, at least 25%, at least 30%, at least 40%, at least 50%, at least 60%, at least 70%, at least 75%, at least 80%, at least 90%, or at least 95%) during or after treatment, as compared to an earlier time point.

The invention will be further described in the following examples, which do not limit the scope of the invention described in the claims.

EXAMPLES

Example 1—Susceptibility of *Pseudomonas aeruginosa* Biofilm to Alpha-Helical Peptides 1. Materials and Methods Bacterial Strains and Media—

*P. aeruginosa* (ATCC 19429, American Type Culture Collection, Manassas, Va.) was grown in Nutrient Broth (Difco Laboratories, Detroit, Mich.) at 37° C. for 24 hours with shaking at 200 rpm. The CFU/ml was determined by growth on Nutrient Agar plates. For anti-microbial assays, frozen enumerated aliquots were thawed immediately before use.

Anti-Microbial Assays—

Anti-microbial activity of the NA-CATH and NA-CATH: ATRA1-ATRA1 (AAPPTEC, Louisville, Ky.), the variations on the ATRA peptides (Genscript, Piscataway, N.J.), LL-37 (AnaSpec 61302) and D-LL-37 (Lifetein, South Plainfield, N.J.) against *P. aeruginosa* were determined as previously described, with some modification (Han et al. (2008) *Biochem. Biophys. Res. Commun.*, 371(4): 670-674; and Papanastasiou et al. (2009) *Apmis*, 117(7):492-499). The sequences and net charges of the peptides are shown in Table 1.

In a 96-well plate, $1 \times 10^5$ CFU per well of bacteria were incubated with different peptide concentrations (in serial dilutions of 1:10 or 1:5 per dilution) in a solution of buffer containing 10 mM sodium phosphate at pH 7.4 (3 hours, 37°

C.). Serial dilutions were then carried out in 1× Dulbecco's PBS and plated in triplicate on Nutrient Agar plates, incubated (37° C., 24 hours) and CFUs counted. Bacterial survival at each peptide concentration was calculated as previously described (Amer et al. (2010) *Biochem. Biophys. Res. Commun.*, 396(2):246-251; and de Latour et al. (2010) *Biochem. Biophys. Res. Commun.*, 396(4):825-830) based on the percentage of colonies in each experimental plate relative to the average number of colonies observed for assay cultures lacking peptide. The peptide concentration required to kill 50% of the *P. aeruginosa* in the antimicrobial assay cultures (EC50) was determined by plotting percent survival as a function of the log of peptide concentration ($\log_{10}$) and fitting the data using GraphPad Prism 5 (GraphPad Software Inc., San Diego, Calif., USA), using the equation:

$$Y = \text{Bottom} + ((\text{Top} - \text{Bottom})/(1 + 10^{[(\log EC50 - X)*\text{Hill Slope}]}))$$

where Y corresponds to bacterial survival (in percentage) at a given peptide concentration (μg/ml), with X being the logarithm of that concentration. In the equation, "Top" and "Bottom" refer to the upper and lower boundaries and were constrained to values <100% and >0%, respectively. For graphing purposes, samples that had no peptide were plotted at $10^{-9}$ μg/ml peptide. EC50 values were determined by fitting the data from the anti-microbial assays to a standard sigmoidal dose-response curve. Each experiment was repeated at least twice, and a representative experiment is shown, for clarity. 95% confidence intervals (CI) are reported to indicate the error of each EC50 determination.

In order to study the in vitro killing kinetics of the LL-37, D-LL-37, and NACATH:ATRA1-ATRA1 peptides, cultures of *P. aeruginosa* were incubated with the peptides in 10 mM sodium phosphate. The concentrations used in the assay were: 1.0 μg/ml of LL-37, 1.0 μg/ml of NA-CATH, and 0.73 μg/ml of NA-CATH:ATRA1-ATRA1. The anti-microbial activity of the peptides was determined over a period of 3 hours, and plated in triplicate, as previously described (Amer et al., supra).

CD Spectroscopy—

CD spectra of the peptides were collected using Jasco J-815 spectropolarimeter. Samples were allowed to equilibrate for 10 minutes at 25° C. prior to data collection in a 0.1-cm path length cuvette, with a chamber temperature 25° C. throughout each scan. Spectra were collected from 190 to 260 nm using 0.2-nm intervals; 3 scans per sample were averaged. All peptides were analyzed at 250 μg/mL in 10 mM sodium phosphate (pH 7), 50% (v/v) trifluoroethanol (TFE) in 10 mM sodium phosphate (pH 7) (Lee et al. (2003) *Biochem. Biophys. Res. Commun.*, 309(3):591-597).

Biofilm Production—

Biofilm production was measured as previously described (Durham-Colleran et al. (2010) *Microb. Ecol.*, 59(3):457-465) with the following modifications. *P. aeruginosa* ($1 \times 10^5$ CFU) in 200 μl of TSB media (Trypticase Soy Broth) was incubated with peptide at concentrations of 1.0, 0.1, and 0.01 μg/ml for 24 hours at 37° C. (Table 2). Optical density of the cultures (OD600 nm) at 24 hours was determined prior to staining as a measure of bacterial growth. Six wells were used for each peptide concentration (n=6). Biofilm production was measured using the crystal violet stain technique (Durham-Colleran et al., supra).

Motility Assays—

Twitching motility of *P. aeruginosa* was measured after 16 hours, 20 hours, 24 hours, and 48 hours of incubation at 37° C. on LB plates containing 1% (wt/vol) agar and LB broth (Overhage et al. (2008) *Infect. Immun.*, 76(9):4176-4182). *P. aeruginosa* cells were spot inoculated using a needle, and zone diameters were determined by measuring at least 3 times across the zone. Assays were carried out with 4 μg/ml D-LL-37 or L-LL-37, or controls (n=30).

Examination of D- and L-LL-37 Sensitivity to Trypsin—

The proteolytic stability of the enantiomers L-LL-37 and D-LL-37 was assessed in the presence of trypsin. The peptides (18 μg) were dissolved in 90 μl of water. Either water or 0.05% trypsin (10 μl) was added to the peptide solutions, and the mixtures were incubated at 37° C. for 1 hour. After incubation, 10 μl aliquots were taken into an 18% Tris-Glycine gel. After running, the gel was transferred to a clean tray and a silver stain was performed.

*Galleria mellonella* Experiment—

*Galleria mellonella* (wax moth caterpillars) were obtained from Vanderhorst Wholesale (Saint Marys, Ohio). Eight to twelve caterpillars of equal size/weight were randomly assigned to each group. A 1 mL tuberculin syringe was used to inject 10 μl of $1 \times 10^3$ CFU/ml of *P. aeruginosa* into each caterpillar via the last left proleg. The caterpillars were then immediately injected in the dorsal side with 10 μl of either PBS, 5 μg of ciprofloxacin, 10 μg D- or L-LL-37, or 10 μg of NA-CATH:ATRA1-ATRA1. Caterpillar control groups included: injected with only PBS, ciprofloxacin, or AMPs. The insects were then observed daily for their survival status.

Statistical Analysis—

Anti-microbial assay measurements were performed in triplicate, biofilm assays were done at least in duplicate, and representative experiments are shown. Standard deviations of the mean of each set are represented on each graph. Where error bars are not shown, the error was very small. Confidence Interval (CI) (95%) is presented to demonstrate the statistical overlap of the data. Statistically significant differences were assessed using Student's t tests.

TABLE 1

Peptides used in the studies described in Example 1

| Anti-microbial peptide | Sequence | Net charge | SEQ ID NO: |
|---|---|---|---|
| NA-CATH | KRFKKFFKKLKNSVKKRAKKFFKKPKVIGVTFPF* | 15 | 1 |
| NA-CATH: ATRA1-ATRA1 | KRFKKFFKKLKNSVKKRFKKFFKKLKVIGVTFPF | 15 | 2 |
| ATRA-1 | KRFKKFFKKLK-NH₂ | 8 | 3 |
| ATRA-2 | KRAKKFFKKPK-NH₂ | 8 | 4 |
| LL-37 | LLGDFFRKSKEKIGKEFKRIVQRIKDFLRNLVPRTES | 6 | 5 |
| D-LL-37 | *LLGDFFRKSKEKIGKEFKRIVQRIKDFLRNLVPRTES* | 6 | 5 |

TABLE 1 -continued

Peptides used in the studies described in Example 1

| Anti-microbial peptide | Sequence | Net charge | SEQ ID NO: |
|---|---|---|---|
| mCRAMP | GLLRKGGEKIGEKLKKIGQKIKNFFQKLVPQPEQ | 6 | 6 |
| Scrambled LL-37 | GLKLRFEFSKIKGEFLKTPEVRFRDIKLKDNRISVQR | 6 | 7 |

*ATRA motifs are underlined.

TABLE 2

EC50 of AMPs against *P. aeruginosa*

| Anti-microbial peptide | Molecular weight (g/mol)* | EC50 (µg/ml) | 95% CI | EC50 (µM) |
|---|---|---|---|---|
| NA-CATH | 5885.5 | 0.52 | 0.39-0.69 | 0.09 |
| NA-CATH: ATRA1-ATRA1 | 5977.6 | 0.37 | 0.21-0.63 | 0.06 |
| ATRA-1 | 2409.06 | 0.64 | 0.52-0.79 | 0.27 |
| ATRA-2 | 2316.96 | 62.8 | 27.7-949 | 27.1 |
| LL-37 | 5177.42 | 0.47 | 0.28-0.78 | 0.09 |
| D-LL-37 | 5177.42 | 0.72 | 0.37-1.36 | 0.14 |

*The molecular weight for each peptide reflects the TFA salts of the peptide. The molecular weights were used to convert the EC50 in µg/ml to µM, to enable comparisons on a molecule-by-molecule basis.

2. Results

Anti-Microbial Performance: Effect of Chirality (D-LL-37 Vs L-LL-37 Against *P. aeruginosa*)—

A concern regarding the use of anti-microbial peptides as potential therapeutics is their potential sensitivity to host or bacterial proteases (Braff et al. (2005) *Infect. Immun.*, 73(10):6771-6781). To determine whether a protease-resistant peptide mimetic of the human cathelicidin (Wade et al. (1990) *Proc. Natl. Acad. Sci. USA*, 87(12):4761-4765) could be generated, an all-D-amino acid version of LL-37 was tested. The anti-microbial EC50 for D-LL-37 against *P. aeruginosa* was determined to be 0.72 µg/ml, compared to 0.47 µg/ml for wild-type LL-37 (Table 2, FIG. 1*e*). Thus, there was no significant difference in anti-microbial activity between the two peptides.

Anti-Microbial Performance: Small Synthetic Peptides Demonstrate Anti-Microbial Activity Against *P. aeruginosa*—

*P. aeruginosa* also was subjected to treatment with two short, synthetic peptides (Table 1), ATRA-1 and ATRA-2. These two peptides differ at the 3rd (F/A) and 10th (L/P) position, which has been shown to affect the anti-microbial activity of those peptides against *Francisella novicida*, *Escherichia coli* (Amer et al., supra), *Aggregatibacter actinomycetemcomitans* (de Latour et al., supra), and *Staphylococcus aureus*. The EC50 values of ATRA-1 and ATRA-2 were determined to be statistically different (P<0.05, Student's t test) at 0.64 and 62.8 µg/ml, respectively (Table 2, FIG. 1*d*). These two peptides have the same net charge of +8, highly similar sequences, and are both 11 amino acid residues in length.

Anti-Microbial Performance: LL-37 and NA-CATH-Derived Peptide are Anti-Microbial Against *P. aeruginosa*—

The anti-microbial effectiveness of NA-CATH was tested against *P. aeruginosa*, and the performance of this peptide was compared to that of the well-studied cathelicidin LL-37. The EC50 for NA-CATH was found to be 0.52 µg/ml (FIG. 1*a*). The peptide NA-CATH:ATRA1-ATRA1 incorporates modifications to the NA-CATH sequence in which the second ATRA motif has been changed to match the sequence of the first ATRA motif (Table 2) thus creating a perfect repeat. This synthetic cathelicidin had an EC50 value that was determined to be 0.37 µg/ml, and thus was not statistically more effective against *P. aeruginosa* than the NA-CATH parent peptide (FIG. 1*b*) or LL-37 (FIG. 1*c*). In agreement with reported potencies (Gordon et al. (2005) *Curr. Eye Res.*, 30(5):385-394), it was found that the EC50 for LL-37 was 0.47 µg/ml, which is within the range LL-37 levels reported in human plasma (1.18 µg/ml) (Sorensen et al. (1997) *J. Immunol. Methods*, 206(1-2):53-59), suggesting that this is a physiologically relevant potency of LL-37. Previous experiments had shown that the alterations made to NA-CATH to create NA-CATH:ATRA1-ATRA1 resulted in a statistically significant (P<0.05, Student's t test) improvement in anti-microbial activity against *S. aureus* (Dean et al. (2011) *BMC Microbiol.*, 11:114).

Inhibition of Biofilm Formation at Sub-Anti-Microbial Concentrations or Under Non-Anti-Microbial Conditions—

A concern of the utility of anti-microbial peptides as potential therapeutics is the sensitivity of the anti-microbial activity to salt. Multiple studies have shown that LL-37 demonstrates reduced anti-microbial action in environments with high ionic concentrations (Travis et al. (2000) *Infect. Immun.*, 68(5):2748-2755; and Cox et al. (2003) *Peptides* 24(11): 1741-1746) such as in physiologic salt concentration (123-150 mM NaCl). However, LL-37 can inhibit biofilm formation by *P. aeruginosa* (Overhage et al., supra), *S. epidermidis* (Hell et al. (2010) *Lett. Appl. Microbiol.*, 50(2): 211-215), *F. novicida* (Amer et al., supra), and *S. aureus* in media with high concentrations of salt. LL-37 also is capable of degrading pre-formed biofilms of *S. aureus* and *P. aeruginosa* (Altman et al. (2006) *Antimicrob. Chemother.*, 58(1): 198-201).

Figure 2A:
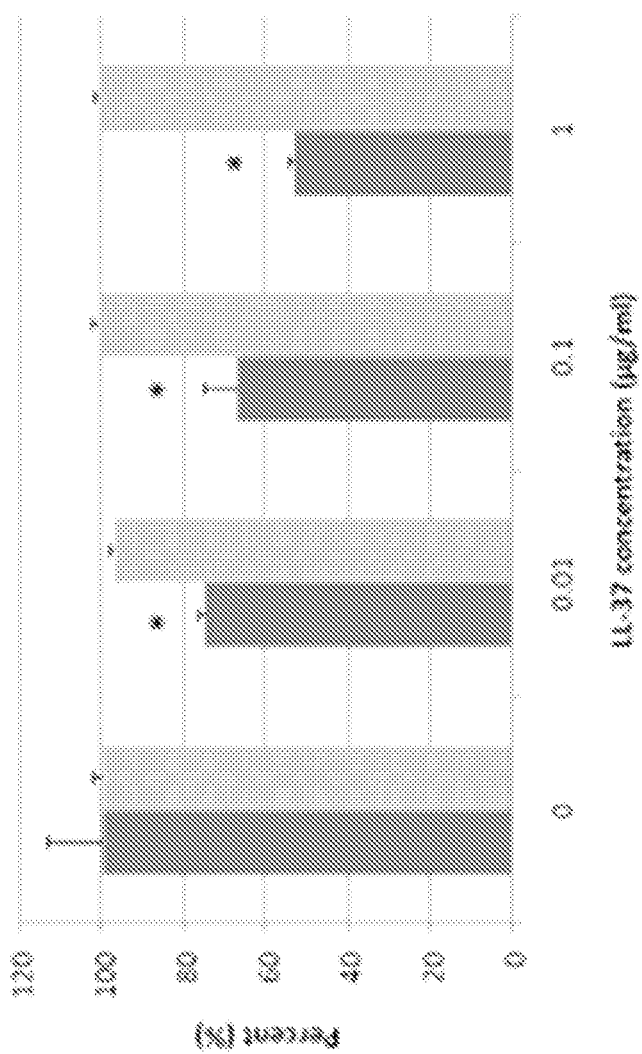
Figure 2B:
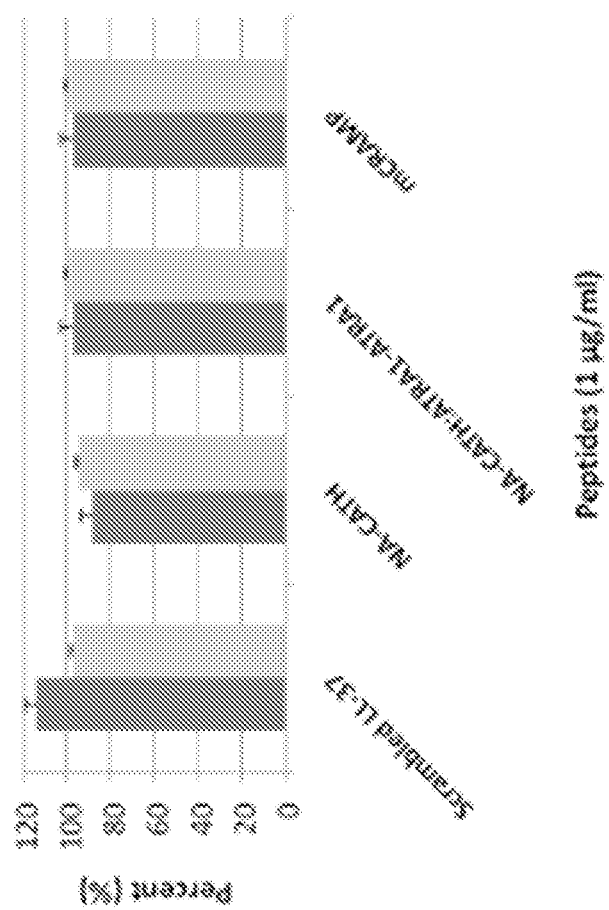
Figure 2C:
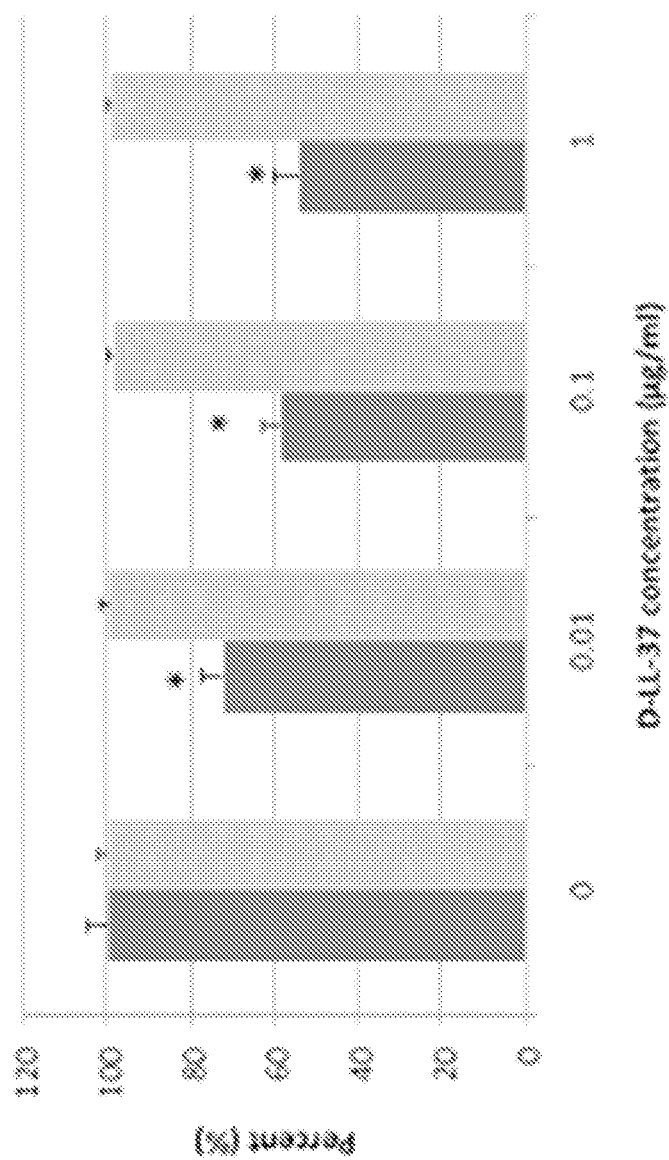
Figure 2D:
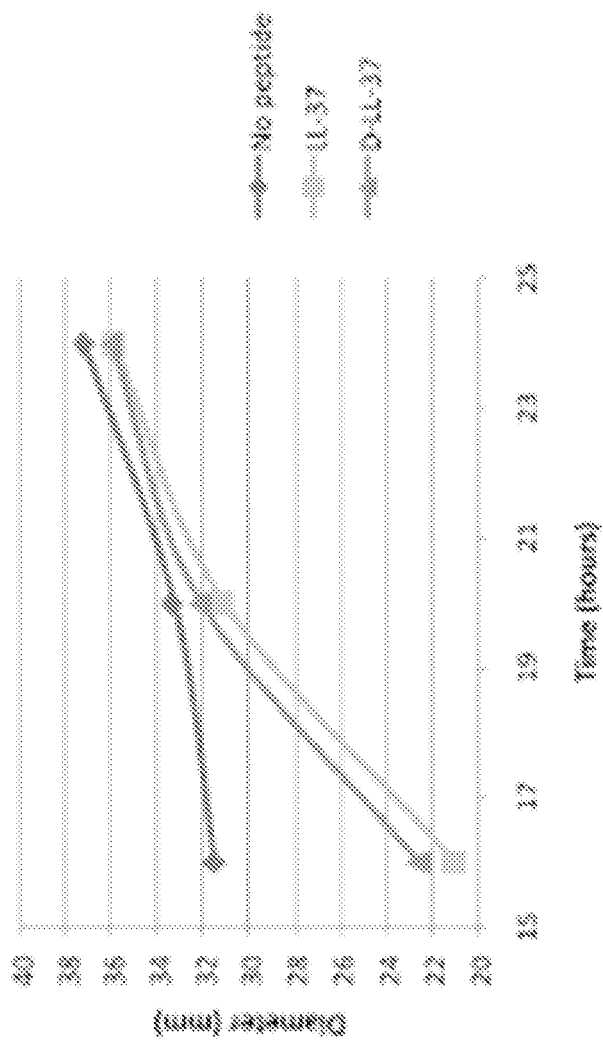

The present studies demonstrated similar salt-independent anti-biofilm activity for D-LL-37 against *P. aeruginosa*. Various concentrations of NA-CATH, NA-CATH:ATRA1-ATRA1, LL-37, D-LL-37, mCRAMP, and scrambled LL-37 were incubated with *S. aureus* in biofilm experiments in TSB (relatively high salt (86 mM NaCl)) for 24 hours. Both mCRAMP, a murine homolog of LL-37 (67% identical to LL-37 in amino acid sequence), and scrambled LL-37 (identical amino acids in random order) functioned as negative controls for this experiment; the former was previously known to have no inhibitory effect (Overhage et al., supra). The scrambled version of LL-37, having the same charge and net amino-acid composition as LL-37 but lacking significant helical character, showed no inhibition of biofilm formation at any concentration tested (FIG. 2*b*), thus demonstrating sequence specificity of the anti-biofilm effect.

FIG. 2 (2*a*-2*c*) shows that levels of bacterial growth (OD600 nm at 24 hours) were not decreased even at the peptide concentrations equal to that of its calculated EC50 in 10 mM phosphate buffer. The MIC could not be calculated because there was no inhibition of growth at any concentration tested, thus MIC >1 µg/ml. When biofilm production was determined in the presence of varying amounts of peptide, there was significant inhibition of biofilm formation by L- and D-LL-37; all other peptides were ineffective. Thus, LL-37 was found to inhibit biofilm formation up to ~50% of control at 1 µg/ml (FIG. 2c). D-LL-37 also was found to be an active anti-biofilm peptide, with maximal biofilm inhibition observed at 1 µg/ml, inhibiting ~50% of biofilm formation (FIG. 2b).

D-LL-37 and L-LL-37 Stimulate Twitching Motility—

Twitching motility is required for the formation of Pseudomonas biofilm (O'Toole and Kolter (1998) Mol. Microbiol., 30(2):295-304). The ability of D-LL-37 and L-LL-37 to stimulate twitching motility of P. aeruginosa was assessed. Both D- and L-LL-37 stimulated the rate of twitching motility (FIGS. 2d and 2e) at low concentrations of peptide (4 µg/ml). This significant (P<0.01, Student's t test) increase in the rate of twitching on surface motility was 1.7 and 1.9 mm/hour on LB (1% agarose) plates, for D- and L-LL-37, respectively. P. aeruginosa in the absence of peptide was determined to have a twitching motility rate of 0.7 mm/hr. LL-37 has been shown to have an insignificant effect on the swimming and swarming motility of P. aeruginosa (Overhage et al., supra), so this was not examined.

CD Spectral Analysis of the Secondary Structure of D- and L-LL-37—

Figure 3:
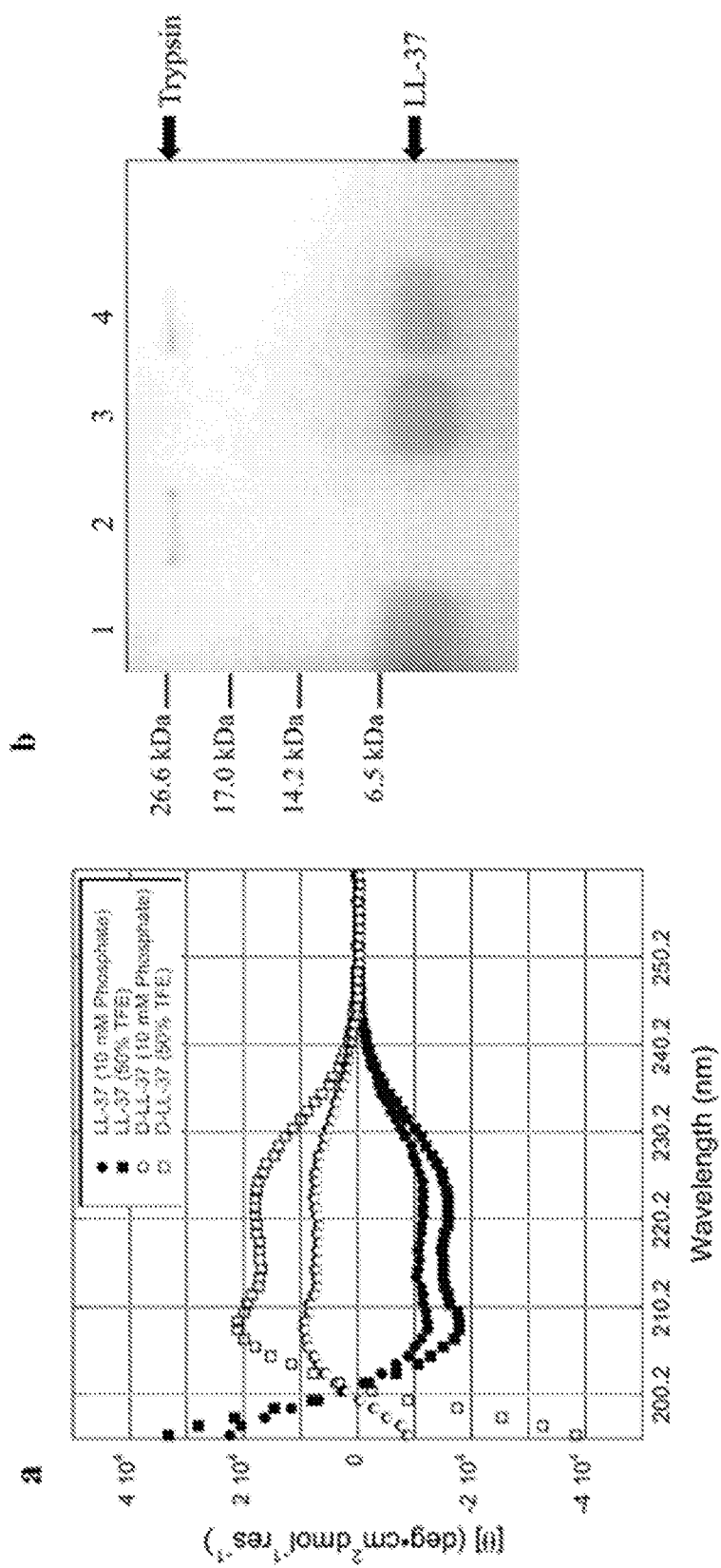
FIG. 3a is a graph plotting the spectra for L-LL-37 and D-LL-37, showing that these peptides exhibit significant helical character in 10 mM phosphate buffer at pH 7.4. The spectrum for D-LL-37 (open circles) was the mirror image of that of the L-peptide (filled circles). The spectra for both D- and L-LL-37 (open and filled squares, respectively) became more intense when the peptides were in 50% TFE in 10 mM phosphate at pH 7.4, consistent with the peptides exhibiting more helical character.
FIG. 3b is a picture of a silver-stained gel showing the effects of trypsin on L-LL-37 and D-LL-37. Lane 1, L-LL-37; Lane 2, L-LL-37 with trypsin; Lane 3, D-LL-37; Lane 4, D-LL-37 with trypsin.

CD spectra of the peptides were obtained for D- and L-LL-37. Pronounced dichroic minima at 222 and 208 nm are traits of helical peptides. Cathelcidins often exhibit little helical behavior at low concentrations in aqueous buffer (Johansson et al. (1998) J. Biol. Chem. 273(6):3718-3724), assuming their most helical structure when in association with a biological membrane or a hydrophobic membrane mimic such as trifluoroethanol (TFE), a strongly helix-promoting environment. The stable helical character, when interacting with bacterial membranes, may contribute to their potent anti-microbial activity (Park et al. (2004) J. Biol. Chem., 279(14):13896-13901). The spectra for L- and D-LL-37 exhibited helical character in pH=7.4 in 10 mM phosphate buffer, consistent with previous results (Johansson et al., supra). As expected, the spectrum for D-LL-37 was the mirror image of that of the L-enantiomer (FIG. 3a). The spectra for both D- and L-LL-37 demonstrated more helical character when the peptides were in 50% TFE in pH 7.4 10 mM phosphate (a membrane mimic).

D-LL-37 is Resistant to Trypsin—

FIG. 3b shows the stability of the enantiomeric peptides, D-LL-37 and L-LL-37, in the presence of 0.05% trypsin after incubation for 1 hour at 37° C. The L-form peptide, LL-37 at 200 µg/ml, was 100% digested by the protease after the 1 hour incubation. D-LL-37 at 200 µg/ml showed no degradation in the presence of trypsin, with equal band intensities as quantified by densitometry (NIH ImageJ).

G. mellonella Infection by P. aeruginosa with AMP and Antibiotic Treatments—

Figure 4:
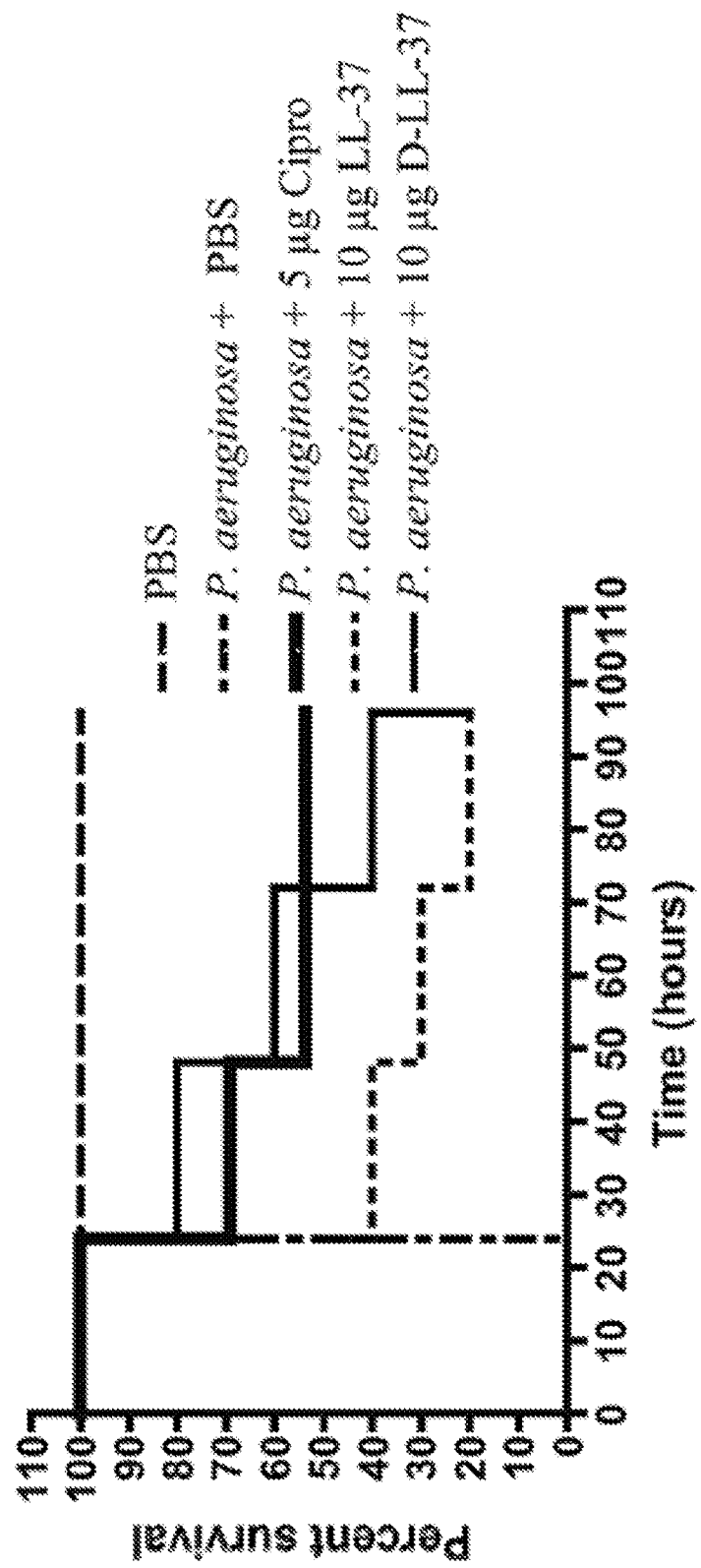
FIG. 4 is a graph plotting survival of non-infected (PBS only) *Galleria mellonella* or *G. mellonella* infected with *P. aeruginosa* and the treated with PBS, ciprofloxacin, D-LL-37, or L-LL-37, as indicated. Non-infected groups fared similarly to the PBS only group. The non-infected PBS group had the highest survival rate and was significantly different from all other groups (p<0.002). Infected cells without treatment failed to survive beyond 24 hours. A single dose of ciprofloxacin or either D- or L-LL-37 was effective when compared to the infected control group (p<0.01), but these groups were not different from each other. NA-CATH:ATRA1-ATRA1 also was tested, but was ineffective at prolonging survival.

G. mellonella infected with P. aeruginosa was used as a model in vivo system (Jander et al. (2000) J. Bacteriol., 182(13):3843-3845) to study the effectiveness of treatment with selected anti-microbial peptides. G. mellonella were infected with either $1 \times 10^3$ CFU bacteria of P. aeruginosa and immediately treated with a single dose of 10 µl PBS (no treatment control), 5 µg ciprofloxacin, 10 µg LL-37, 10 µg D-LL-37, or 10 µg NA-CATH:ATRA1-ATRA1 (FIG. 4). Multiple controls were utilized (PBS or and injection of non-infected G. mellonella with the treatment used in the experiment) in order to measure the effects that the injection or the anti-microbials had on the host system. These negative controls had similar effects; no death was observed. In the positive control, no P. aeruginosa-infected G. mellonella survived beyond 24 hours. The ciprofloxacin (55%), LL-37 (20%), and D-LL-37 (20%) treated groups all demonstrated similarly prolonged survival (p-value <0.01) and were not statistically different from each other. NA-CATH:ATRA1-ATRA1 treatment did not improve survival, with all G. melonella dead by 24 hours. There was no significant difference in the survival rate between D- and L-LL-37.

Taken together, these studies demonstrated that LL-37 and its D-enantiomer, D-LL-37, as well as NA-CATH, and NA-CATH-derived peptides, have anti-microbial activity against the gram-negative opportunist pathogen, Pseudomonas aeruginosa. The effective peptides' EC50 values, when converted from µg/ml to µM to reflect the number of molecules of peptide and to accommodate the different molecular weights of the peptides, ranged from 0.06 to 0.27 µM. The lowest EC50 belonged to NA-CATH:ATRA1-ATRA1, a result consistent with prior observations for other bacteria (Dean et al., supra). In addition, it was determined that L- and D-LL-37 were able to inhibit the development of biofilms in two ways: stimulatory activity in twitching motility assays, and anti-biofilm activity in anti-biofilm assays. Further, trypsin did not degrade D-LL-37 (FIG. 3), while L-LL-37 was completely degraded. Such protease resistance may allow D-LL-37 to remain active in a wound such that it can inhibit biofilm formation in vivo. Incorporation of anti-biofilm peptides or their synthetic derivatives in therapeutic topical applications may improve outcomes for infections ranging from wounds, burns, implanted medical devices and pneumonia.

Example 2—Cathelicidin Peptides with Anti-Microbial and Anti-Biofilm Activity Against *Staphylococcus aureus*

1. Materials and Methods

Bacterial Strains and Media—

S. aureus (ATCC 25923, American Type Culture Collection, Manassas, Va.) was grown in Nutrient Broth (Difco Laboratories, Detroit, Mich.) at pH 7, 37° C., for 24 hours with shaking at 200 rpm. The overnight culture was frozen with 20% glycerol and stored at −80° C. The frozen stock was enumerated (CFU/ml) by dilution plating and growth on Nutrient Agar plates.

Peptides and Anti-Microbial Assays—

Sequences and net charges of the peptides are shown in Table 1. The molecular weight reported for each peptide reflects the trifluoroacetic acid (TFA) salt form. NA-CATH, NA-CATH:ATRA1-ATRA1, ATRA-1, ATRA-1A, ATRA-2 peptides (86.1 and 89.7, 97.2, 94.5, and 88.2%, respectively) (Genscript, Piscataway, N.J.), LL-37 (95% purity) (AnaSpec 61302) and D-LL-37 (92.0% purity) (Lifetein, South Plainfield, N.J.) were synthesized commercially.

The anti-microbial activity of the NA-CATH and NA-CATH:ATRA1-ATRA1, the variations on the ATRA peptides LL-37 and D-LL-37 against S. aureus were determined as previously described, with some modification (de Latour et al., supra; and Papanastasiou et al., supra). For anti-microbial assays, frozen enumerated aliquots were thawed and gently mixed immediately before use. In a 96-well plate (BD Falcon 353072), $1 \times 10^5$ CFU per well bacteria were incubated with different peptide concentrations (in serial dilutions of 1:10 across the plate) in a solution of buffer containing sterile 10 mM sodium phosphate (pH 7.4) and incubated (3 hours, 37° C.). Negative control wells contained bacteria with no peptide. Serial dilutions were then carried out in sterile 1×PBS (Fisher Scientific) (pH 7)

and plated in triplicate on Nutrient Agar plates, incubated (37° C., 24 hours) and counted. Bacterial survival at each peptide concentration was calculated as previously described (Amer et al., supra, and de Latour et al., supra) based on the percentage of colonies in each experimental plate relative to the average number of colonies observed for assay cultures lacking peptide. The EC50 was calculated as previously described (de Latour et al., supra).

Each experiment was repeated at least twice, and a representative experiment is shown for clarity. Errors were reported based on the standard deviation from the mean of the $\log_{10}$ EC50 values (Gordon et al., supra). 95% confidence intervals were used to determine whether points were statistically different at p=0.05.

CD Spectroscopy—

CD spectra of the peptides were collected using a Jasco J-815 spectropolarimeter. Samples were allowed to equilibrate (10 minutes, 25° C.) prior to data collection in a 0.1 cm path length cuvette, with a chamber temperature 25° C. throughout each scan. Spectra were collected from 190 to 260 nm using 0.2-nm intervals, and 3 scans per sample were averaged. All peptides were analyzed at 250 µg/ml concentration in multiple media: 10 mM sodium phosphate (pH 7), 50% (v/v) trifluoroethanol (TFE) in 10 mM sodium phosphate (pH 7), and 60 mM sodium dodecyl sulfate (SDS) in 10 mM sodium phosphate (pH 7) (Lee et al., supra). Helical wheel projections were made with http://kael.org/helical.htm, projecting peptide sequences onto the helical backbone.

Biofilm Production—

Biofilm production was measured as previously described (Durham-Colleran et al., supra) with the following modifications. S. aureus ($1 \times 10^5$ CFU) in 200 µl of sterile trypticase soy broth media (TSB) (Becton Dickinson and Company) (pH 7) was incubated with either with no peptide, NACATH: ATRA1-ATRA1, NA-CATH, LL-37, D-LL-37, or LL-37 scrambled at concentrations of 1.0, 0.1, and 0.01 µg/ml (24 hours, 37° C.) in a 96 well plate (BD Falcon 353072). The positive control was S. aureus in TSB with no peptide. Six wells were used for each peptide concentration (n=6). After 24 hours, the optical densities (OD) of the wells were taken at 600 nm to quantify biofilm formation. The biofilm production was measured using the crystal violet stain technique (Durham-Colleran et al., supra). All experiments were repeated at least twice.

Biofilm Attachment Assay—

Biofilm attachment assays were performed in 96-well microtiter plates (BD Falcon 353072) as previously described (Overhage et al., supra). Overnight cultures of S. aureus were grown in TSB to an OD600 of about 1.0. 200 µl culture was added to the wells, followed by no peptide, LL-37 scrambled, LL-37, D-LL-37, NA-CATH, or NA-CATH:ATRA1-ATRA1 at 1 µg/ml. The plates were incubated (1 hour, 37° C.) to allow the S. aureus to adhere to the wells. The wells were washed and OD600 measurements were taken, as in the biofilm production experiments, and the average absorbance for each treatment was determined (n=16).

Hemolysis Assay—

Hemolytic activities of the peptides were determined using equine erythrocytes (Hema Resource Inc., Eugene, Oreg., USA) in an assay adapted to a microtiter plate format (Papanastasiou et al., supra). Briefly, erythrocytes were prepared by centrifuging 1 ml fresh defibrinated blood (1620×g, 10 minutes) and resuspending the pelleted cells in 1 ml sterile PBS (Fisher Scientific) (pH 7). The cells were washed with PBS three times, and in the final wash the cells were re-suspended in 0.75 ml PBS. From this, a 2% erythrocyte suspension was prepared for the assay. Aliquots of sterile water (positive control), peptide, and PBS (negative control) were used in a microtiter plate. Various peptide concentrations in sterile 10 mM sodium phosphate (0.1, 1, 10, and 100 µg/ml) were tested (n=12). The assay was then incubated (1 hour, 37° C.). After centrifugation (1000×g, 10 minutes), aliquots of supernatant were carefully transferred to a new microtiter plate and the absorbance was obtained for each well. Percent hemolysis was calculated as previously described (de Latour et al., supra).

Statistical Analysis—

Anti-microbial assay measurements were performed in triplicate biofilm assays with n=6. Standard deviations of the mean of each set are represented on each graph. Where the error bars are not seen, the error was very small. Confidence Interval (CI) (95%) is presented to demonstrate the statistical overlap of the data. For all other assays, p-values were determined by performing a standard T-test.

TABLE 3

Peptides used in the studies described in Example 2

| Anti-microbial peptide | Sequence | Net charge | SEQ ID NO: |
| --- | --- | --- | --- |
| NA-CATH | <u>KRFKKFFKKLK</u>NSVK<u>KRAKKFFKKPK</u>VIGVTFPF* | 15 | 1 |
| NA-CATH: ATRA1-ATRA1 | <u>KRFKKFFKKLK</u>NSVK<u>KRFKKFFKKLK</u>VIGVTFPF | 15 | 2 |
| ATRA-1 | KRFKKFFKKLK-NH2 | 8 | 3 |
| ATRA-2 | KRAKKFFKKPK-NH2 | 8 | 4 |
| ATRA-1A | KRAKKFFKKLK-NH2 | 8 | 8 |
| LL-37 | LLGDFFRKSKEKIGKEFKRIVQRIKDFLRNLVPRTES | 6 | 5 |
| D-LL-37 | *LLGDFFRKSKEKIGKEFKRIVQRIKDFLRNLVPRTES* | 6 | 5 |
| Scrambled LL-37 | GLKLRFEFSKIKGEFLKTPEVRFRDIKLKDNRISVQR | 6 | 7 |

*ATRA motifs are underlined.

TABLE 4

EC50 of AMPs against S. aureus

| Anti-microbial peptide | Molecular weight (g/mol)* | EC50 (µg/ml) | 95% CI | EC50 (µM) |
| --- | --- | --- | --- | --- |
| NA-CATH | 5885.5 | 5.74 ± 1.5 | 2.61-12.6 | 0.98 |
| NA-CATH: ATRA1-ATRA1 | 5977.6 | 1.01 ± 1.4 | 0.50-2.06 | 0.17 |
| ATRA-1 | 2409.06 | 1.06 ± 1.5 | 0.49-2.31 | 0.44 |
| ATRA-2 | 2316.96 | 37.1 ± 1.6 | 14.6-94.3 | 16.0 |
| ATRA-1A | 2332.96 | 1.45 ± 1.5 | 0.64-3.29 | 0.62 |
| LL-37 | 5177.42 | 2.6 ± 1.7 | 0.83-8.12 | 0.60 |
| D-LL-37 | 5177.42 | 26.2 ± 1.4 | 12.5-54.8 | 5.06 |

*Molecular weights reflect the TFA salt for each peptide, and were used to convert EC50s in µg/ml to µM, for comparison on a molecule-by-molecule basis.

2. Results

Anti-Microbial Performance: LL-37 and NA-CATH are Anti-Microbial Against S. aureus—

Figure 5A:
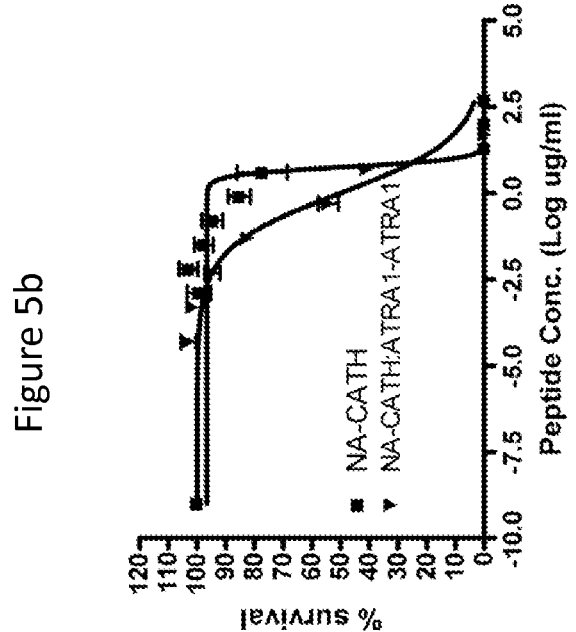

Peptide sequences are shown in Table 3. The anti-microbial effectiveness of NA-CATH was tested against S. aureus, and the performance of this peptide was compared to the activity of LL-37. The EC50 for NA-CATH was found to be 5.7 µg/ml (FIG. 5a). The peptide NA-CATH:ATRA1-ATRA1 incorporates a modification to NA-CATH in which the second ATRA motif has been changed to match the sequence of the first ATRA motif (Table 3). This synthetic cathelicidin had an EC50 value that was determined to be 1.0 µg/ml, more effective against S. aureus (p<0.05) than the parental NA-CATH (FIG. 5b), but not statistically different from LL-37 (FIG. 5c). In agreement with reported potencies (Gordon et al., supra), the EC50 for LL-37 was 2.6 µg/ml. This is similar to the level of LL-37 reported in human plasma (1.18 µg/ml) (Sorensen et al., supra), suggesting that this is a physiologically relevant potency of LL-37.

Anti-Microbial Performance: Synthetic Peptides Demonstrate Anti-Microbial Activity Against S. aureus—

S. aureus also was subjected to treatment with the synthetic peptides ATRA-1, ATRA-2, ATRA-1A, and NA-CATH:ATRA1-ATRA1 (Table 3), which represent variations on the ATRA-repeated motif of NA-CATH. ATRA-1 and ATRA-2 differ at the $3^{rd}$ (F/A) and $10^{th}$ (L/P) positions. This has been shown to affect the anti-microbial activity of those peptides against Francisella novicida, Escherichia coli (Amer et al., supra) and Aggregatibacter actinomycetemcomitans (de Latour et al., supra). The EC50 values of ATRA-1 and ATRA-2 were determined to be statistically different (p<0.05) at 1.1 and 37 µg/ml, respectively (Table 4), with non-overlapping 95% confidence intervals (FIG. 5d). These two peptides have the same net charge of +8, highly similar sequence and the same length of 11 amino acid residues. The ATRA-1A peptide is a variation on the ATRA-1 peptide that differs from ATRA-1 at the $3^{rd}$ position, which in previous studies with gram-negative bacteria improved its anti-microbial activity. The EC50 of ATRA-1A against S. aureus was 1.5 µg/ml (FIG. 5f); the additional alanine did not significantly improve its activity, as the EC50 for ATRA-1 was 1.1 µg/ml (Table 4), with overlapping confidence intervals.

Figure 5B:
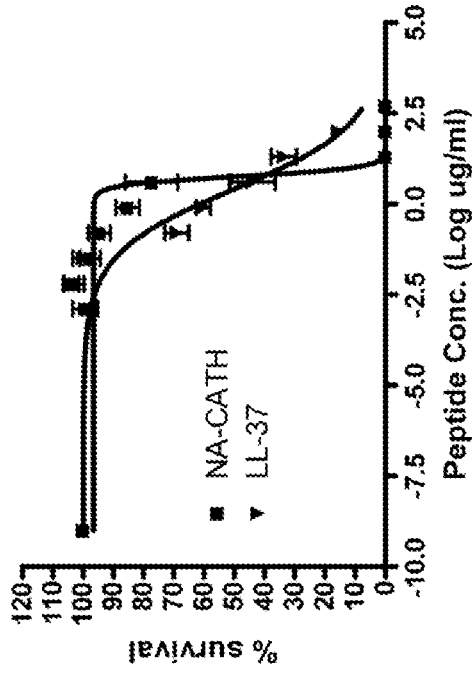
Figures 5E, 5F:
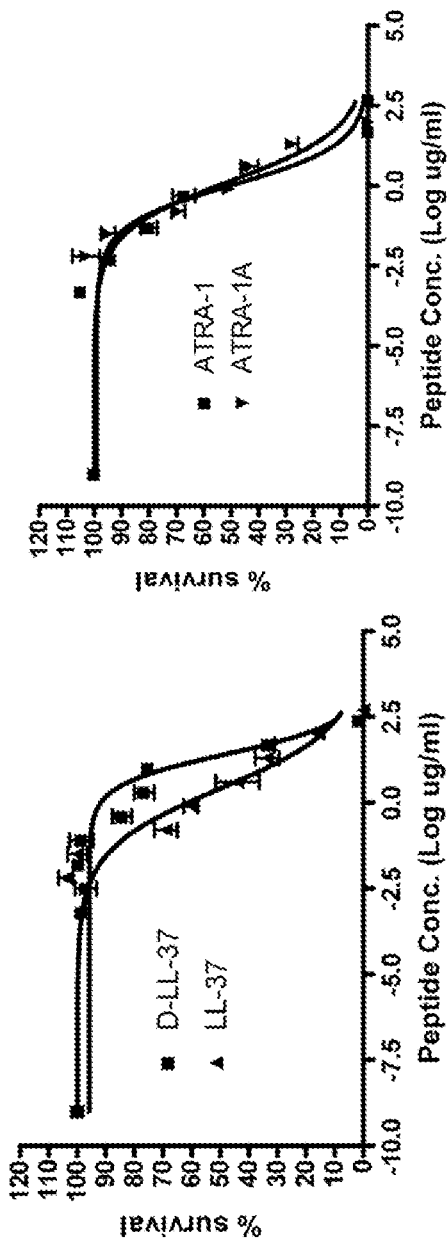

When examined on a molar basis (Table 2), taking into account the activity per molecule of peptide, whether short or long, it was observed that the short, synthetic ATRA-1A peptide was as potent as the full-length NA-CATH against S. aureus (FIGS. 5a and b). In addition, LL-37 was a more effective anti-microbial peptide than either ATRA-1A or NA-CATH (FIG. 5a). However, altering the NA-CATH peptide to have a perfect ATRA repeat (NA-CATH:ATRA1-ATRA1) resulted in the greatest potency, judged either in terms of molarity or µg/ml (FIGS. 5b and 5c).

Anti-Microbial Performance: Effect of Chirality (D-LL-37 Vs. L-LL-37 Against S. aureus)—

A concern regarding the use of anti-microbial peptides as therapeutics is their potential sensitivity to host or bacterial proteases (Braff et al., supra). To generate a protease-resistant peptide mimetic of the human cathelicidin (Wade et al., supra), an all-D-amino acid version of LL-37 was tested. This peptide is the chiral opposite to LL-37, but has an otherwise identical sequence and net charge. The anti-microbial EC50 value of the D-peptide against S. aureus was determined to be 26 µg/ml, compared to 2.6 µg/ml for wild-type LL-37 (Table 4, FIG. 5e). The apparently decreased potency of D-LL-37 may reflect deficiencies in the ability of the peptide isomer to effectively interact with the gram-positive bacterial cell membrane, or it may have diminished helical character relative to the L-isomer. Alternatively, it may indicate the existence of a previously unidentified chiral binding target for the LL-37 peptide in S. aureus.

Hemolytic Activity of Peptides—

The hemolytic activity of each of the peptides was determined using 2% horse erythrocytes as previously described (Papanastasiou, supra). In these assays, no significant hemolysis was demonstrated by any of the tested peptides up to a concentration of 100 µg/ml. Low hemolytic activity of the ATRA series of peptides was previously reported (de Latour et al., supra). At 100 µg/ml, NA-CATH:ATRA1-ATRA1 did not elicit statistically significant hemolysis compared to PBS (Fisher Scientific) (pH 7) or to the parent compound, NA-CATH (p=0.98). Other studies have examined hemolytic activity of cathelicidins up to 200 µg/ml, and found similarly low levels for full-length LL-37 and short ATRA fragments (Zhao et al. (2008) Peptides 29:1685-1691; de Latour et al., supra). At 100 µg/ml, D-LL-37 also elicited no significant hemolysis and was not statistically significantly different from the L-form (p=0.29 compared to LL-37).

Inhibition of Biofilm Formation at Sub-Anti-Microbial Concentrations or Under Non-Anti-Microbial Conditions—

Another concern regarding the utility of anti-microbial peptides as therapeutics is the sensitivity of anti-microbial activity to salt. LL-37 has demonstrated reduced anti-microbial action in environments with high ionic concentrations (Cox et al., supra; and Travis et al., supra), such as in physiologic salt concentrations (123-150 mM NaCl). However, LL-37 can inhibit biofilm formation by P. aeruginosa (Overhage et al., supra), S. epidermidis (Hell et al., supra), and F. novicida (Amer et al., supra) in media with high concentrations of salt. Thus, although the LL-37 peptide loses its anti-microbial activity in high salt, it retains its anti-biofilm activity.

Figure 6A:
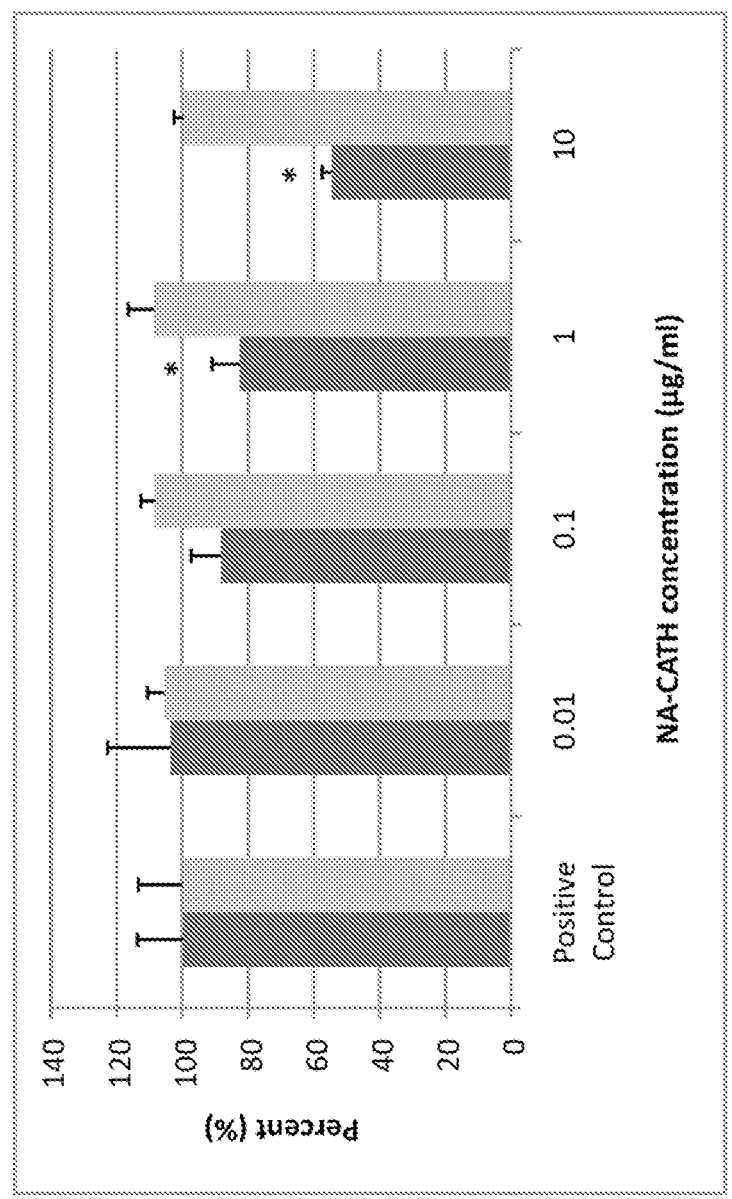
FIGS. 6a-6e are a series of graphs plotting inhibition of *S. aureus* biofilm formation after incubation with various peptides. In each graph, growth (absorbance at 600 nm) is indicated by gray bars with "0 peptide" control set to 100%. Biofilm growth was detected as the absorbance of crystal violet stain (570 nm). Percent biofilm production is indicated by black bars (n=6), relative to "0 peptide" control. Each experiment is a representative of at least two independent trials. Error bars indicate the standard deviation from the mean. The asterisk (*) indicates statistical difference from the positive control (p<0.01).
Figure 6B:
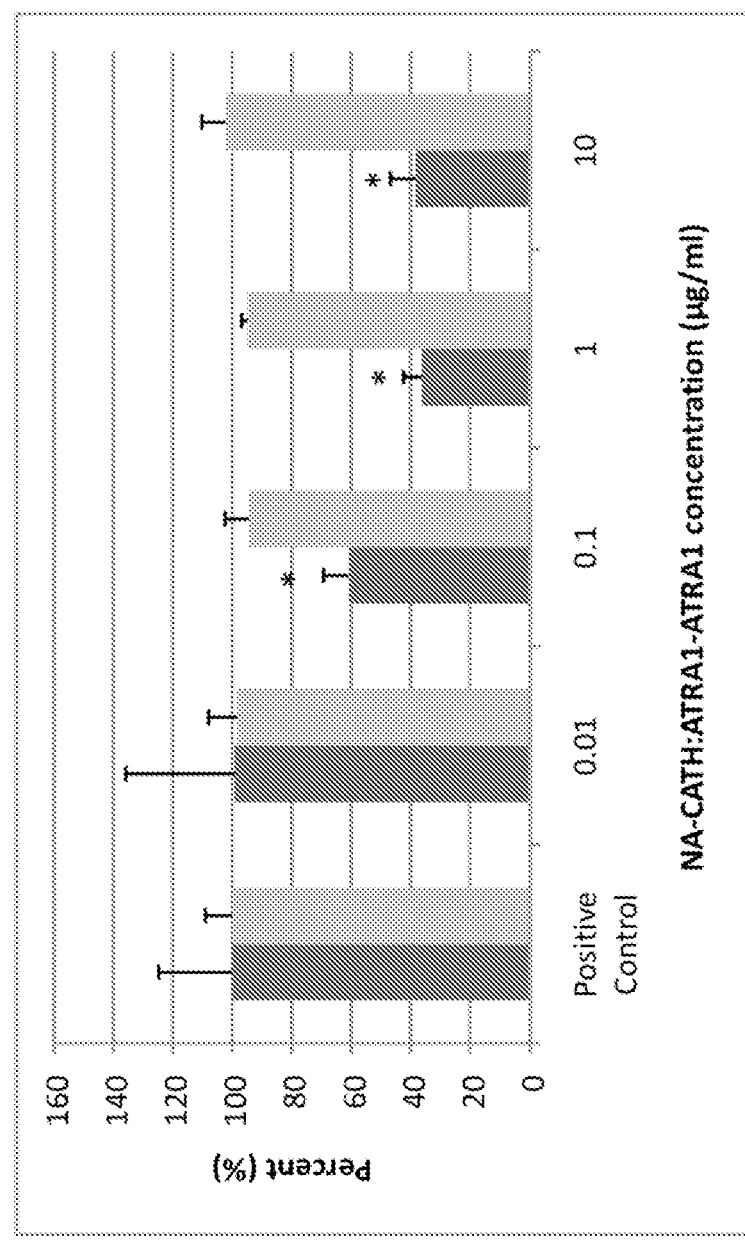

These studies demonstrated similar salt-independent anti-biofilm activity for the NACATH, NA-CATH:ATRA1-ATRA1, and D-LL-37 peptides. Various concentrations of NA-CATH, NA-CATH:ATRA1-ATRA1, LL-37, D-LL-37, and scrambled LL-37 were incubated with S. aureus in biofilm experiments in sterile TSB (relatively high salt) for 24 hours. FIGS. 6a-6e show that levels of bacterial growth (OD600 at 24 hours) were not decreased even at peptide concentrations equal to the calculated EC50 concentrations in sterile 10 mM sodium phosphate. The MIC of LL-37 against S. aureus was determined to be >400 µg/ml in TSB. When the biofilm production was determined in the presence of varying amounts of peptide, significant inhibition of biofilm formation by each peptide except the scrambled LL-37 peptide was observed at concentrations in which no anti-microbial activity was observed. Thus, wild-type NA-CATH was found to inhibit biofilm formation up to ~50% of control at 10 µg/ml (FIG. 6a). NA-CATH:ATRA1-ATRA1 was the most active anti-biofilm peptide, with maximal biofilm inhibition observed at 1 µg/ml, inhibiting ~60% of biofilm formation (FIG. 6b).

Figure 6C:
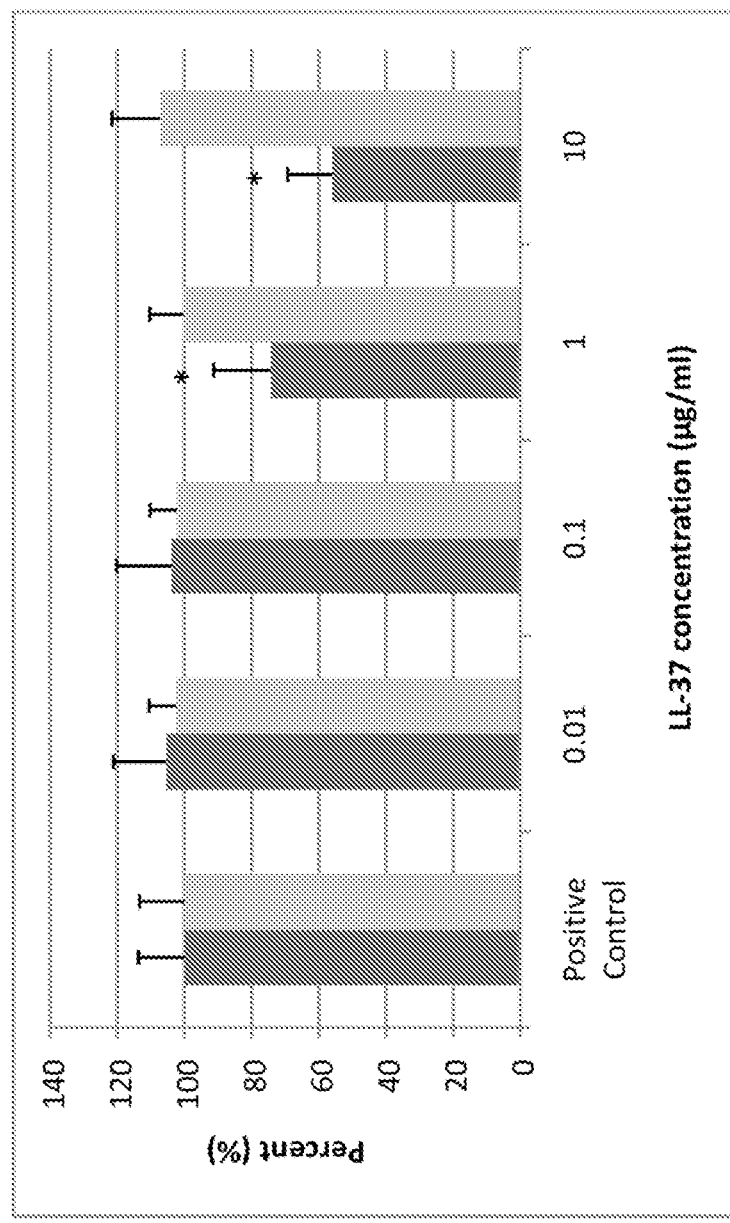
Figure 6D:
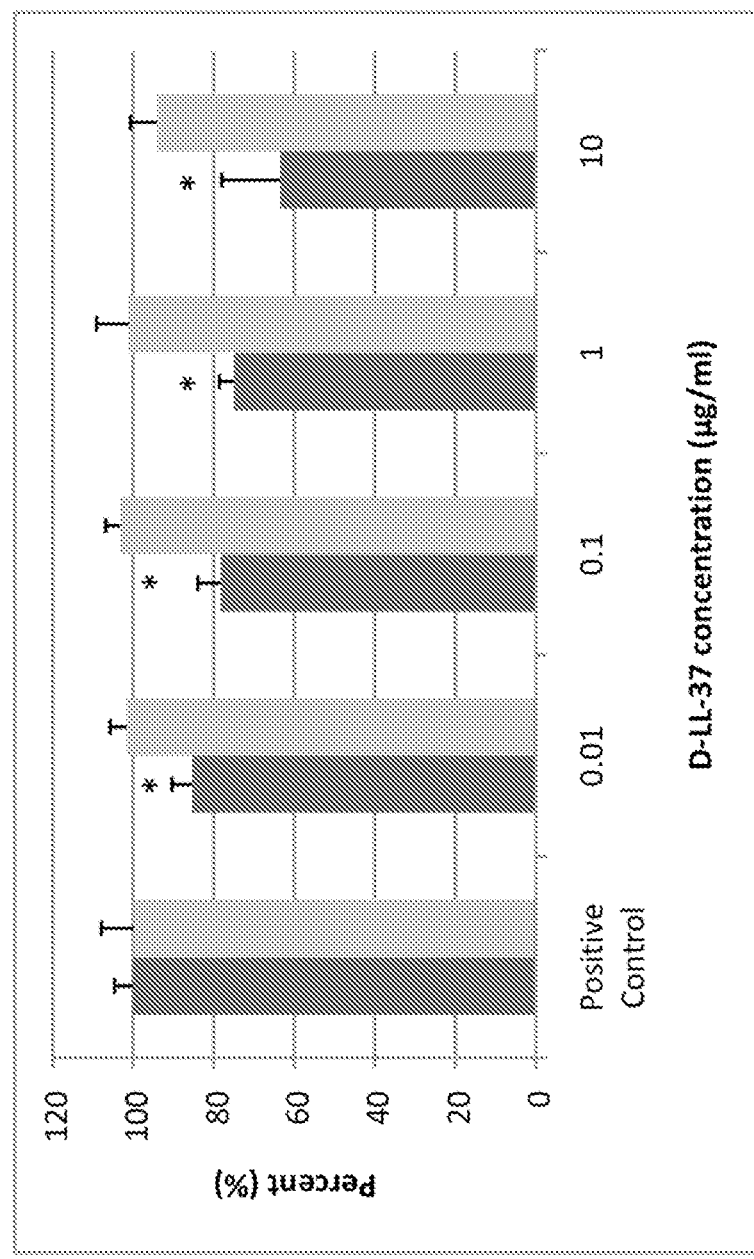
Figure 6E:
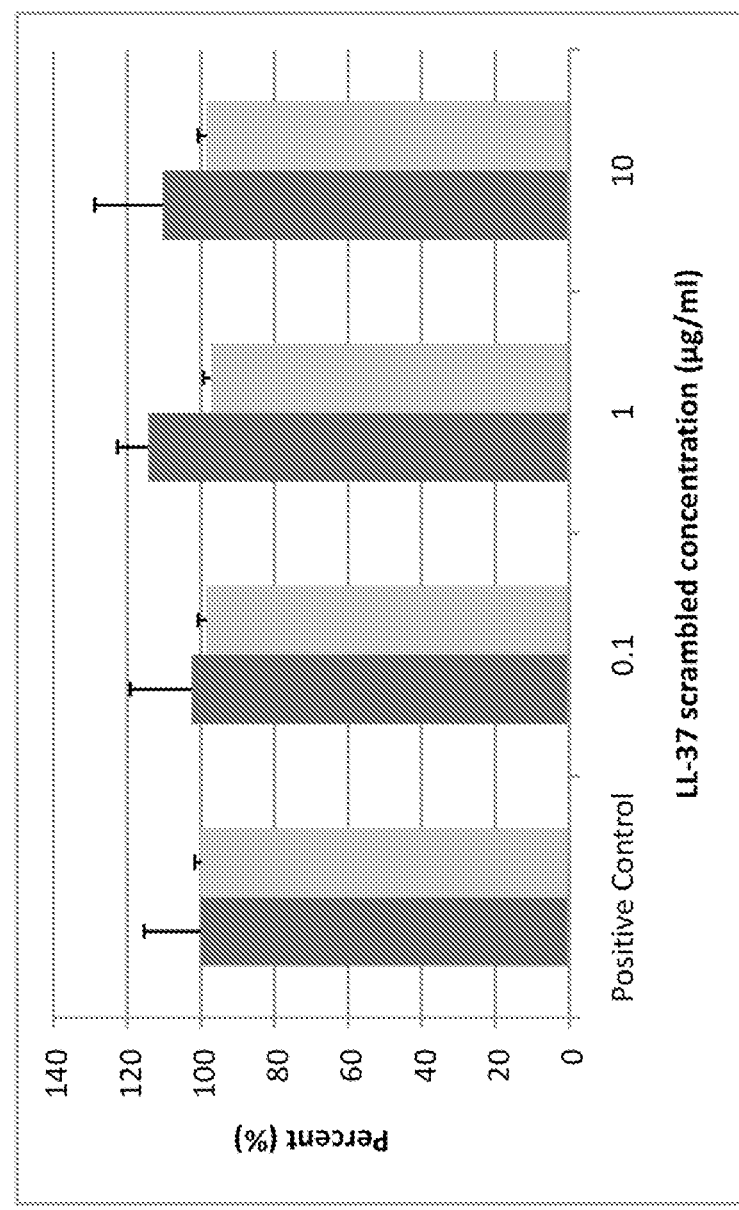

For LL-37, significant anti-biofilm inhibition for *S. aureus* was observed at 10 µg/ml, inhibiting ~40% biofilm formation (FIG. 6c). The anti-biofilm activity of D-LL-37 was very similar to that of LL-37, showing ~40% inhibition at 10 µg/ml (FIG. 6d). In other experiments, D-LL-37 at 26 µg/ml was able to inhibit as much as ~80% of biofilm formation. The strong anti-biofilm effect of D-LL-37 was surprising, as it had been categorized as an ineffective AMP (Table 4), and was 10 fold less effective than LL-37. This result suggested that anti-microbial activity and anti-biofilm activity of peptides may be due to different mechanisms. For example, the anti-microbial activity could result from direct physical interaction of the peptide on the bacterial membrane, while anti-biofilm activity could be mediated by alteration of bacterial gene expression (Overhage et al., supra). The scrambled version of LL-37, having the same charge and net amino-acid composition as LL-37 but lacking significant helical character, showed no inhibition of biofilm formation at any concentration tested (FIG. 6e), thus demonstrating sequence specificity of the anti-biofilm effect.

D- and L-LL-37 Affect *S. Aureus* Biofilm Attachment—

Figure 7:
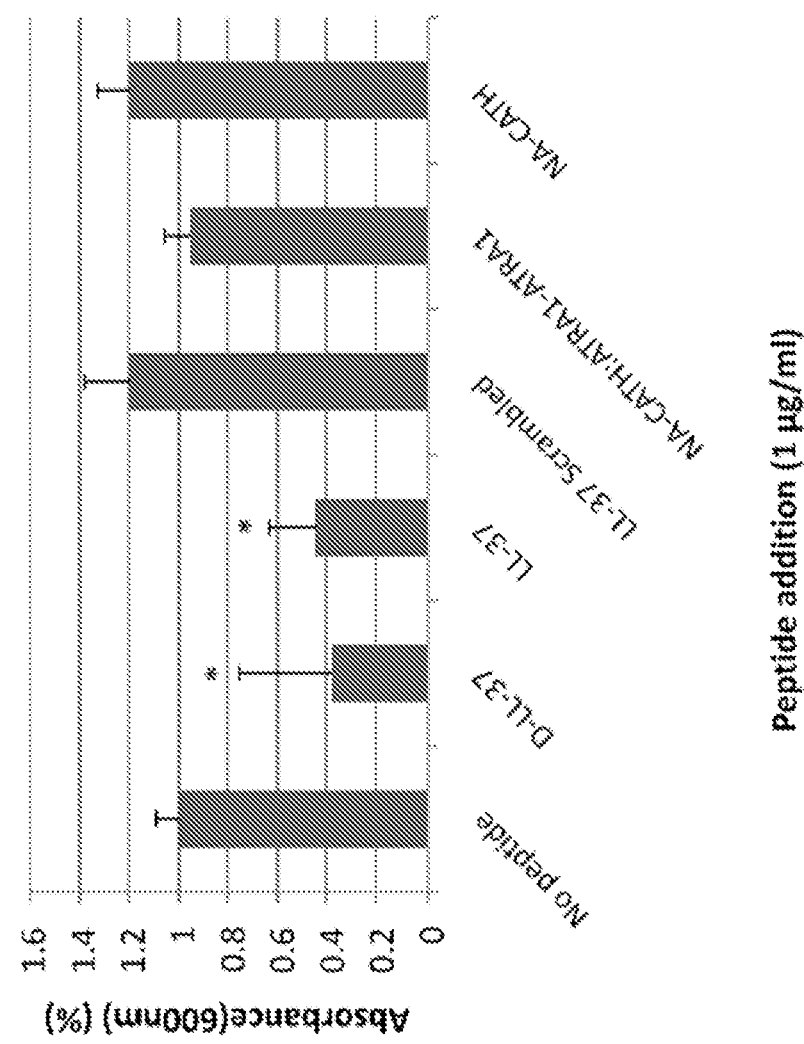
FIG. 7 is a graph plotting initial attachment of *S. aureus* to wells in the presence of LL-37 scrambled (negative control), LL-37, D-LL-37, NA-CATH, or NA-CATH:ATRA1-ATRA1, as indicated.

The attachment of *Staphylococcus* spp. to solid surfaces is largely seen as an essential step in the formation of biofilm. Since most of the peptides tested in the biofilm assays described herein were capable of inhibiting biofilm formation (except for scrambled LL-37), a possible mechanism for this action was investigated. LL-37, D-LL-37, NACATH, NA-CATH:ATRA1-ATRA1, and a negative control (scrambled LL-37) were tested against *S. aureus* for a short duration at a concentration of 1 µg/ml, only allowing for initial adherence to the wells. For LL-37 and D-LL-37, the measured attachment to the polystyrene wells was significantly decreased (P<0.01, Student's t test; FIG. 7). Scrambled LL-37, NA-CATH, and NA-CATH:ATRA1-ATRA1 did not decrease *S. aureus* adherence.

CD Spectral Analysis of Peptides—

Figure 8A:
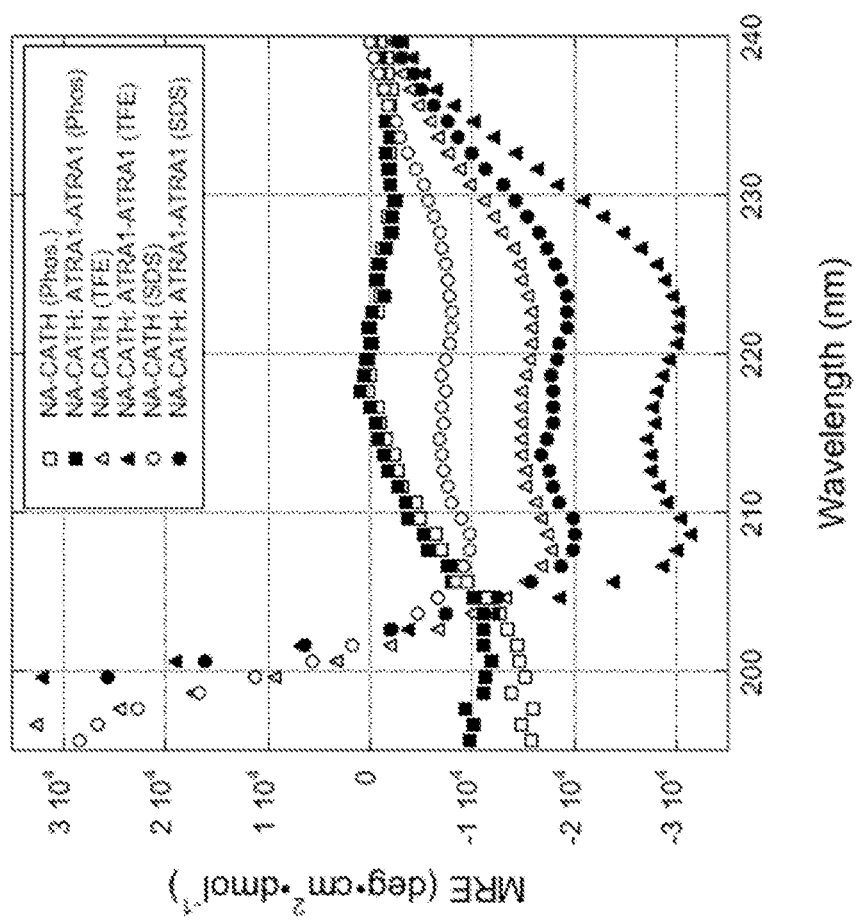
FIG. 8a is a graph plotting Circular dichroism (CD) spectra of NA-CATH and NA-CATH:ATRA1-ATRA1 in SDS, 10 mM phosphate buffer (pH 7), or 50% TFE in 10 mM phosphate buffer (pH 7). The pronounced dichroic minima at 222 and 208 nm are traits of helical peptides.
Figure 8B:
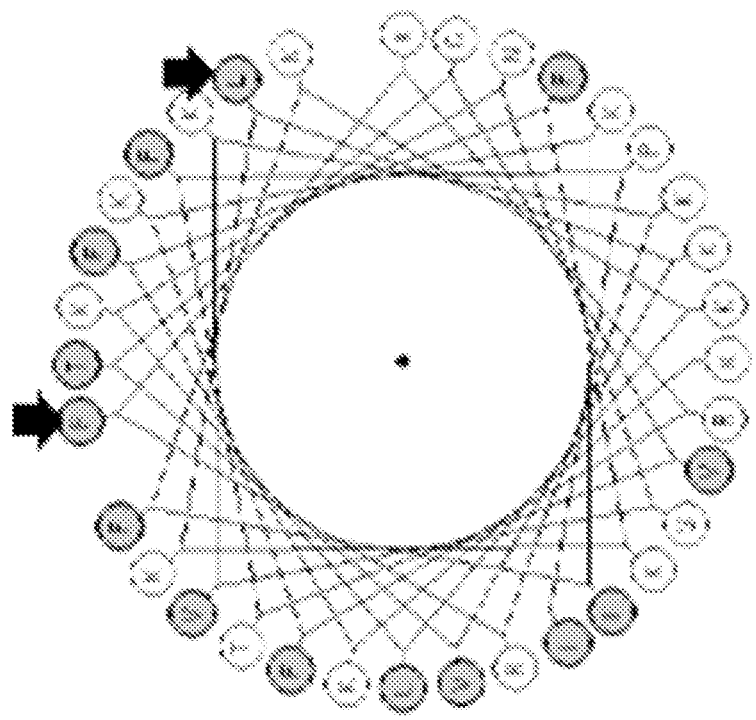
FIG. 8b shows a pair of helical wheel projections in which the sequences of NACATH (left panel) and NA-CATH:ATRA1-ATRA1 (right panel) were projected onto a helical backbone. Altered residues are indicated by the arrows. Shaded circles indicate hydrophobic residues.
Figure 8B:
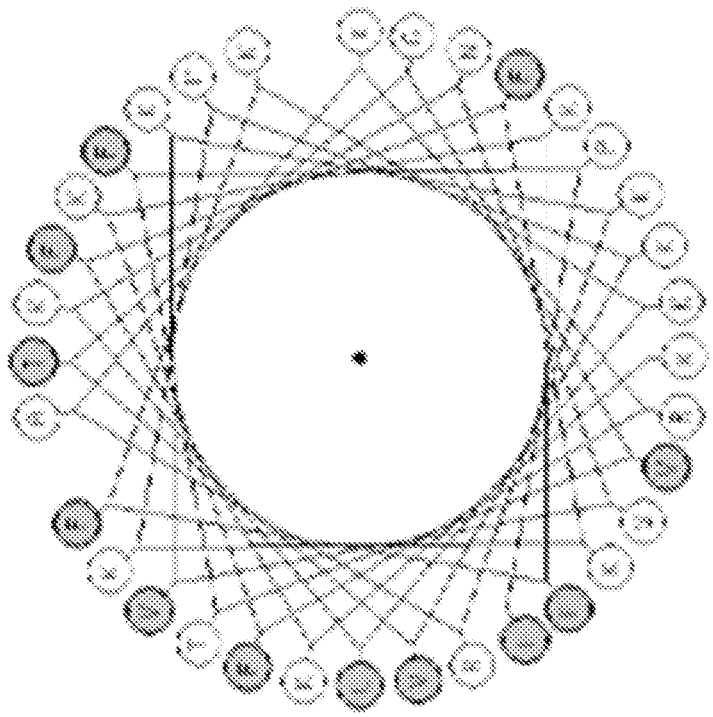
Figure 8C:
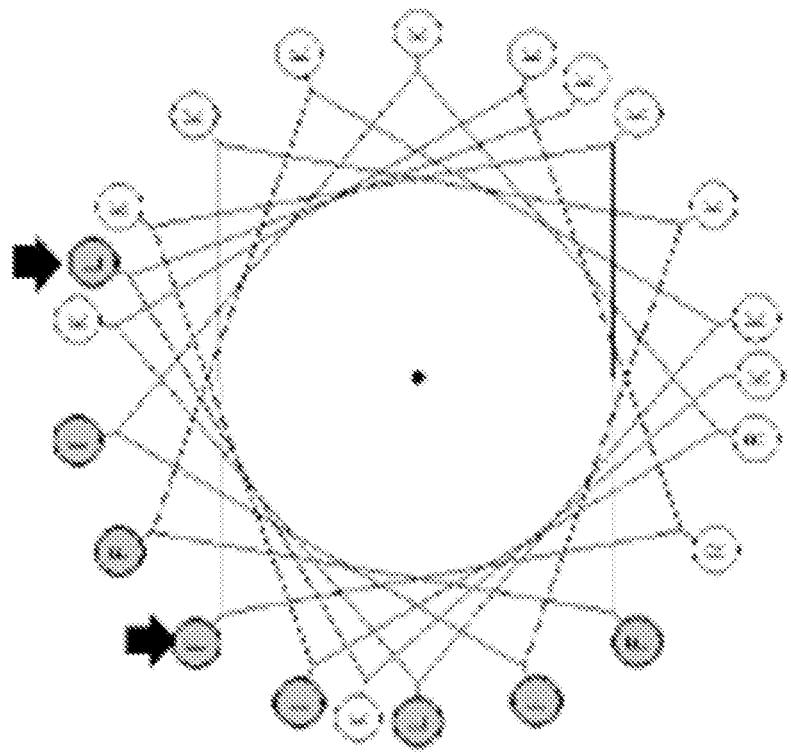
FIG. 8c shows a pair of helical wheel projections in which the sequences of ATRA-2 (left panel) and ATRA-1 (right panel) were projected onto a helical wheel backbone. To enable easier viewing of the contribution of the key differences between the ATRA-2 and ATRA-1 motifs to the hydrophobic face of the peptide, each motif is projected alone on the helical wheel. Altered residues are indicated by arrows, and shaded circles indicate hydrophobic residues.
Figure 8C:
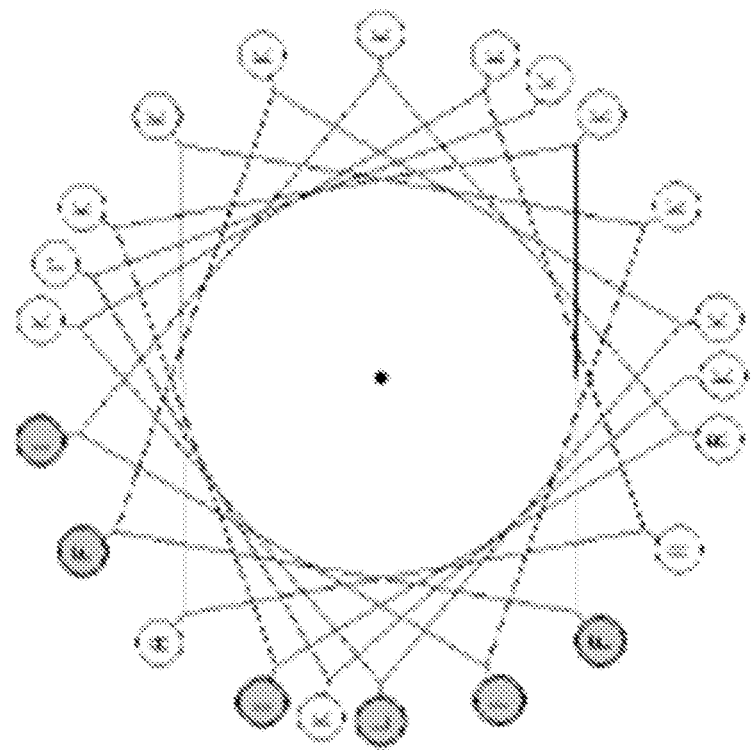

CD spectra of the peptides were obtained. Pronounced dichroic minima at 222 and 208 nm are traits of helical peptides (FIG. 8a). Cathelcidins often exhibit little helical behavior in aqueous buffer, assuming their helical structure only in association with a biological membrane, a membrane mimic such as SDS, or trifluoroethanol (TFE), a strongly helix-promoting environment. SDS can be used to mimic the anionic bacterial membrane (Heilborn et al. (2003) *J. Invest. Dermatol.* 120:379-389), and structural studies using this method have provided insight into peptide-membrane interactions (Mookherjee et al. (2009) *J. Immunol.* 183:2688-2696). Previous studies demonstrated that the ATRA-1 peptide exhibits very strong helical properties, while ATRA-2 peptide had poor helical properties (Amer et al., supra; and de Latour et al., supra), probably due to the proline at the $10^{th}$ position. ATRA-1 also was predicted to present a more cohesive hydrophobic face than ATRA-2 (see below). These characteristics, taken together, may account for the high level of anti-microbial effectiveness displayed by ATRA-1. It was hypothesized that compared to the parental NA-CATH (containing both ATRA-1 and ATRA-2 segments), the NACATH:ATRA1-ATRA1 peptide may benefit from greater and more stable helical character when interacting with bacterial membranes, which may contribute to its increased anti-microbial activity (Park et al., supra). Neither NA-CATH nor NA-CATH:ATRA1-ATRA1 showed well-defined secondary structure in 10 mM sodium phosphate (pH 7) (FIG. 8a). However, both peptides appeared to adopt a helical conformation in 50% TFE, with the NA-CATH:ATRA1-ATRA1 spectrum indicating significantly more helical character than was noted for the NA-CATH parental peptide. SDS may more closely approximate the conditions associated with the interaction between CAMPs and bacterial membranes, and thus CD spectra were also collected for NA-CATH and NA-CATH:ATRA1-ATRA1 in the presence of 60 mM SDS. Both peptides demonstrated helical character under these conditions, but less than they presented in 50% TFE. Again, NACATH:ATRA1-ATRA1 demonstrated more helical character than the wild-type peptide. Moreover, the CD spectrum of NA-CATH:ATRA1-ATRA1 in SDS was comparable to that of NA-CATH in TFE, suggesting that the alterations made in the sequence of NA-CATH:ATRA1-ATRA1 significantly increased its propensity for forming helical structure. When the peptide sequences were projected on a helical wheel (FIG. 8b), the contribution of the substitutions at positions 18 and 25 to a potential hydrophobic face of the NA-CATH:ATRA1-ATRA1 peptide were observed at the top of the helical wheel diagram. On net, the Ala→Phe and Pro→Leu substitutions at positions 18 and 25, respectively, increase the hydrophobicity at those positions, which may improve the interactions between the peptides and the hydrophobic tails in surfactant micelles (and lipid membranes), further stabilizing helical structure in NA-CATH:ATRA1-ATRA1 when interacting with anionic surfactants or lipids. Similarly, when the ATRA-2 and ATRA-1 peptides were projected individually in helical wheel format, the contribution of these two positions to the potential hydrophobic peptide face of each peptide could be seen (FIG. 8c). ATRA-1 may present a more helical face that also is significantly more uniform than that of ATRA-2, with the side chain of phenylalanine at the 3rd position of ATRA-1 exhibiting significantly greater hydrophobic character than the alanine residue at the same position in ATRA-2.

Example 3—Susceptibility of *Candida albicans* to Anti-Microbial Peptides

1. Materials and Methods

*C. albicans* (ATCC 14053) was grown up in 25 mL of Sabouraud Dextrose (SO) broth for 48 hours at 25° C., after which samples were aliquoted into 2 mL microcentrifuge tubes at 0.5 mL. ATRA-1 (SEQ ID NO:3), ATRA-2 (SEQ ID NO:4), ATRA-1A (SEQ ID NO:8), and D-ATRA-1A (SEQ ID NO:8) were tested against *C. albicans* in anti-microbial assays as follows.

On a 96-well plate, $1 \times 10^4$ CFU per well of *C. albicans* were incubated with different peptide concentrations (in serial dilutions of 1:10 and 1:5) starting with 1000 mg in a solution of buffer containing 10 mM sodium phosphate at pH 7.4 (3 hours, 37° C.). Serial dilutions were then carried out in 1x Dulbecco's PBS, and samples were plated in triplicate on Sabouraud Dextrose Agar plates, incubated (25° C., 48 hours) and CFUs were counted. *C. albicans* survival at each peptide concentration was calculated as previously described (Amer et al., supra; de Latour et al., supra), based on the percentage of the number of colonies in each experimental plate relative to the average number of colonies observed for assay cultures lacking peptide. The peptide concentration required to kill 50% of the viable bacteria in the anti-microbial assay cultures (EC50) was determined by plotting percent survival as a function of the log of peptide concentration (log µg/ml) and fitting the data using Graph-Pad Prism 4, using the equation:

$$Y = \text{Bottom} + (\text{Top} - \text{Bottom})/(1 + 10^{[(\log EC50 - X) \cdot \text{Hill Slope}]})$$

where Y corresponds to yeast survival (in percentage) at a given peptide concentration (µg/ml), with X being the logarithm of that concentration (log µg/ml). In the equation, "Top" and "Bottom" refer to the upper and lower boundaries, and were constrained to values <100% and >0%, respectively. For graphing purposes, samples that had no peptide were plotted at $10^{-9}$ µg/ml peptide. EC50 values were determined by fitting the data from the anti-microbial assays to a standard sigmoidal dose-response curve. Each experiment was repeated at least twice, and representative experiments are shown in the figures. Errors were reported based on the standard deviation from the mean of the log EC50 values.

2. Results

Figure 9A:
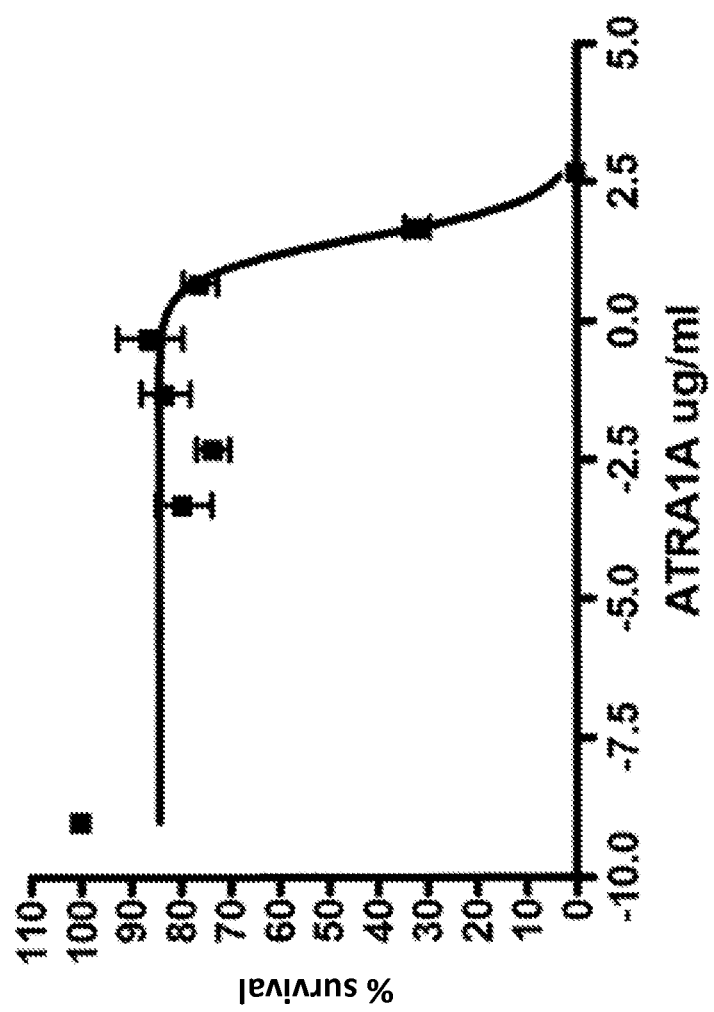
FIGS. 9a-9d are a series of graphs plotting percent survival of *C. albicans* in the presence of anti-microbial peptides ATRA-1A (FIG. 9a), D-ATRA-1A (FIG. 9b), ATRA-1 (FIG. 9c), and ATRA-2 (FIG. 9d).
Figure 9B:
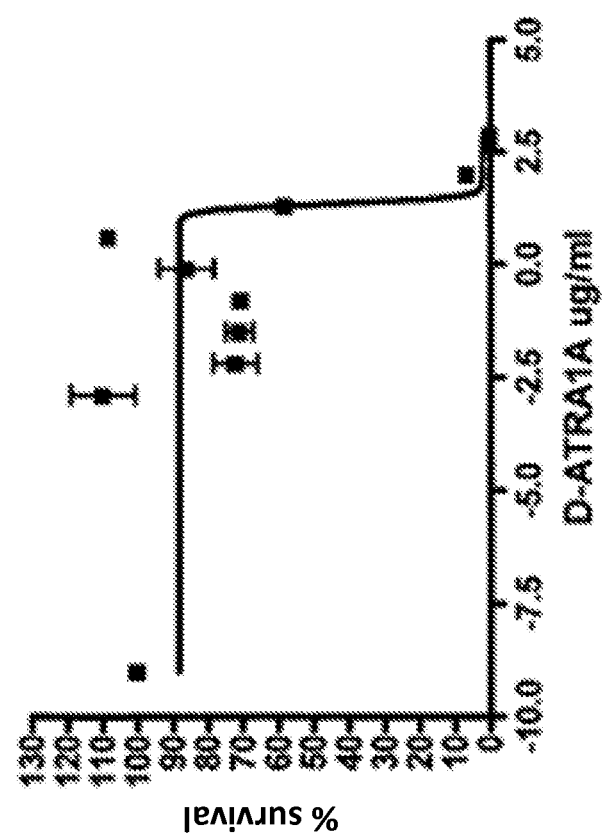
Figure 9C:
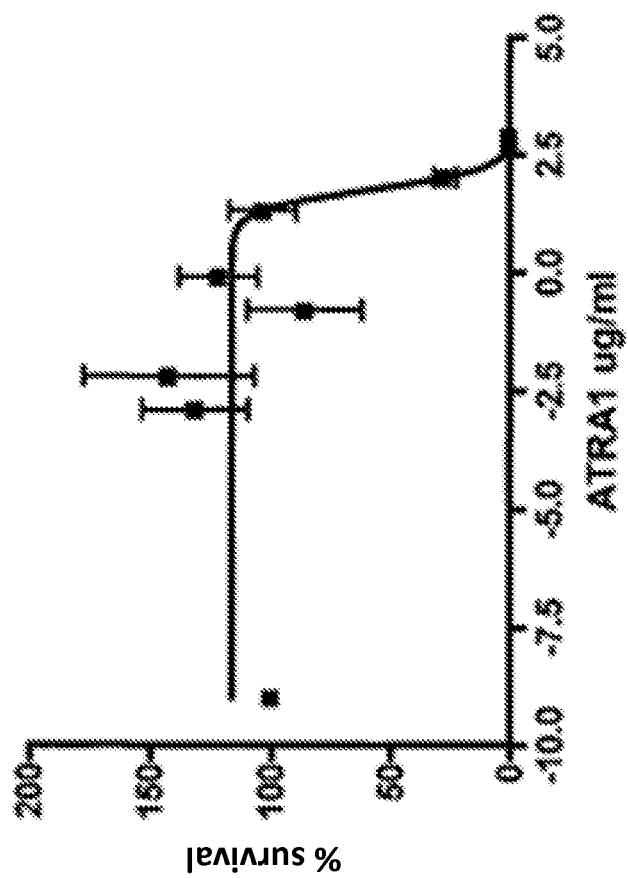
Figure 9D:
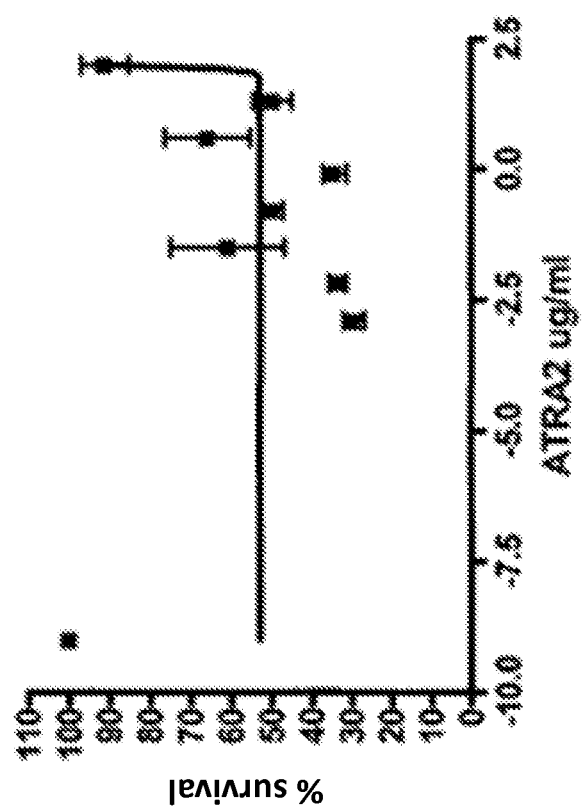

Inhibition of *C. albicans* by the selected ATRA peptides did seem to occur based on the EC50 values calculated by Graphpad (Table 5). 95% CI EC50 values were not available for some graphs, however, and unusual graph shapes also were seen (e.g., FIG. 9d), due to inconsistent growth of the *C. albicans* colonies.

TABLE 5

EC50s for anti-microbial peptides against *C. albicans*

| Anti-microbial peptide | Molecular Weight (g/mol) | EC50 (µg/mL) | 95% CI (µg/mL) | EC50 (µM) |
|---|---|---|---|---|
| ATRA-1 | 1496.9 | 56.37 | 22.06-144.1 | 37.7 |
| ATRA-2 | 1404.8 | 97.27 | NA | 69.2 |
| ATRA-1A | 1420.8 | 33.38 | 18.23-61.1 | 23.5 |
| D-ATRA-1A | 1420.8 | 22.10 | NA | 15.6 |

Although Table 5 provides EC50 values for the selected ATRA peptides against *C. albicans*, the *C. albicans* colonies displayed inconsistent growth on SD plates. This means that colony counts did not display a trend that would accurately determine EC50. Inhibition of *C. albicans* by the ATRA-1A, D-ATRA-1A, and ATRA-1 was consistently seen at 500 and 100 µg, but from that point showed inconsistency in that colony counts of *C. albicans* at concentrations below 100 µg would fluctuate from high to low across trials. Such fluctuating colony counts were seen most strongly in an assay testing ATRA-2 against *C. albicans*, in which the highest concentration of ATRA-2 (500 µg) had higher colony counts than all lower concentrations of ATRA-2. The peptide did not likely cause these fluctuations, as the negative control colony counts for all trials (*C. albicans*+PBS and no peptide) also displayed inconsistent numbers. The *C. albicans* colonies did not seem to grow consistently on the SD plates even when factors such as incubation time and temperature were kept the same.

It is noted that the SD plates were made from scratch (10 g peptone, 40 g dextrose, 15 g agar for 1 L at pH 5.6), rather than with pre-made, commercially available media. This could explain why the *C. albicans* did not display consistent growth.

Example 4—D-Enantiomers of Anti-Microbial Peptides

Peptide Enantiomers:

A panel of CAMPs was selected for study, including peptides ranging from 11 to 37 residues in length (Table 6), although a primary focus for future studies is on the enantiomeric pairs of the shorter peptides (having 11 to 26 residues). The longer peptides (NA-CATH and CAP-18) were included to provide a basis for comparing the performance and biophysical data of the shorter peptide isomers to that of full-length anti-microbial peptides.

NA-CATH and ATRA-1A:

The 34-residue NA-CATH peptide has potent anti-microbial activity against Gram-negative bacteria, including the oral pathogen *Aggregatibacter actinomycetemcomitans* (de Latour et al., supra; and Amer et al., supra). The sequence of NA-CATH reveals an 11-amino acid pattern of residues that is repeated, differing only at two positions. A series of 11-residue peptide amides were designed based on the repeated pattern from NA-CATH, and the anti-microbial effectiveness of these short peptides and the parent *N. atra* cathelicidin was evaluated against *E. coli*, *A. actinomycetemcomitans* and *F. tularensis* (de Latour et al., supra; and Amer et al., supra). ATRA-1A was one of the 11-residue NA-CATH-based peptides that demonstrated significant anti-microbial activity, slightly less than that of the full length NA-CATH.

Figure 10:
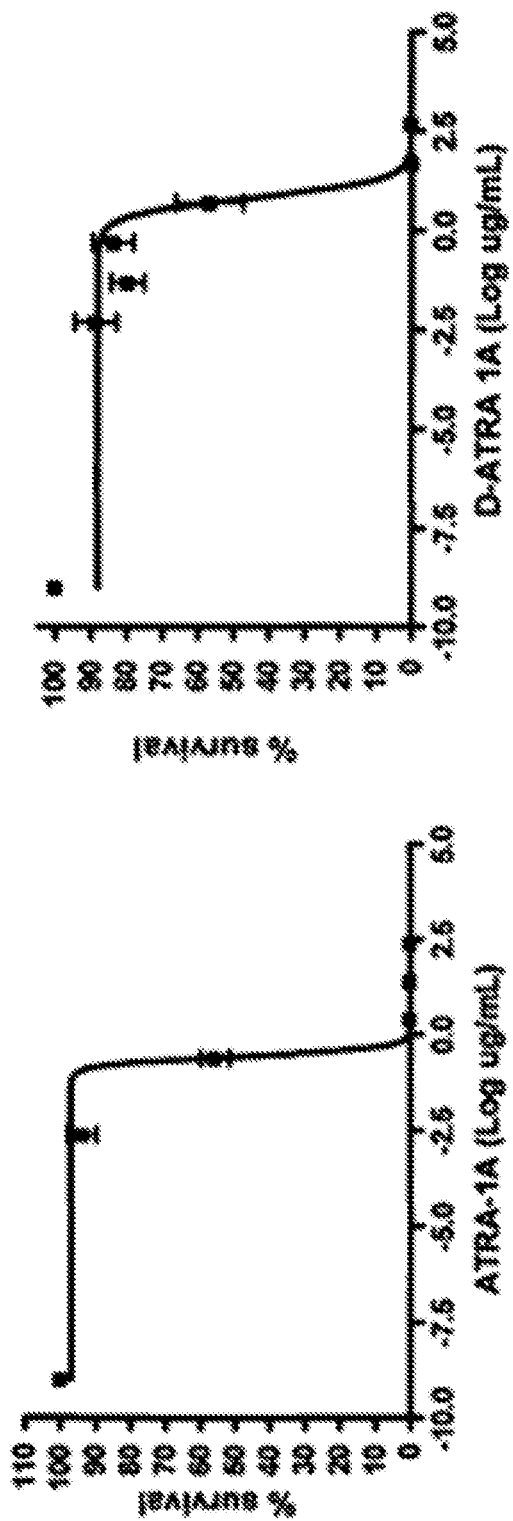
FIG. 10 is a pair of graphs plotting survival of S. aureus after treatment with D-ATRA-1A (left panel) and D-ATRA-1A (right panel).

The scope of the studies was then expanded to include the D-isomer of ATRA-1A. In preliminary studies, the L- and D-isomers of ATRA-1A demonstrated significantly different anti-microbial potencies against the Gram-positive microbe *S. aureus* (FIG. 10). L-ATRA-1A had an EC50 of 0.27 µg/ml, while D-ATRA-1A proved significantly less effective with an EC50 of 6.97 µg/ml, corresponding to a 30-fold difference in their activities.

Figure 11A:
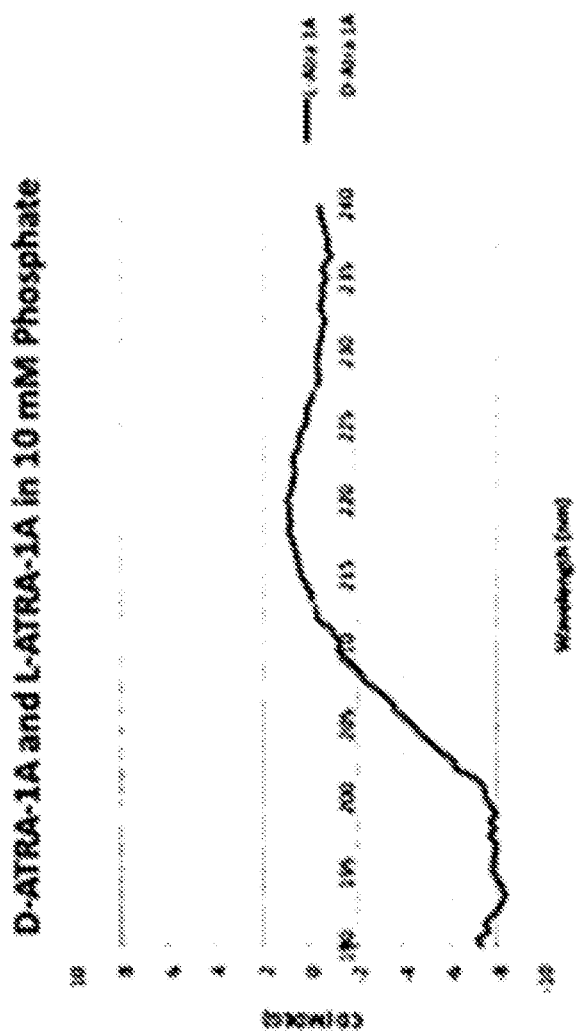
FIGS. 11a and 11b are a pair of graphs plotting CD spectra of L-ATRA-1A (black line) and D-ATRA-1A (gray line) in pH 7.4 10 mM phosphate (FIG. 11a) and pH 7.4 10 mM phosphate with 50% trifluoroethanol (FIG. 11b).
Figure 11B:
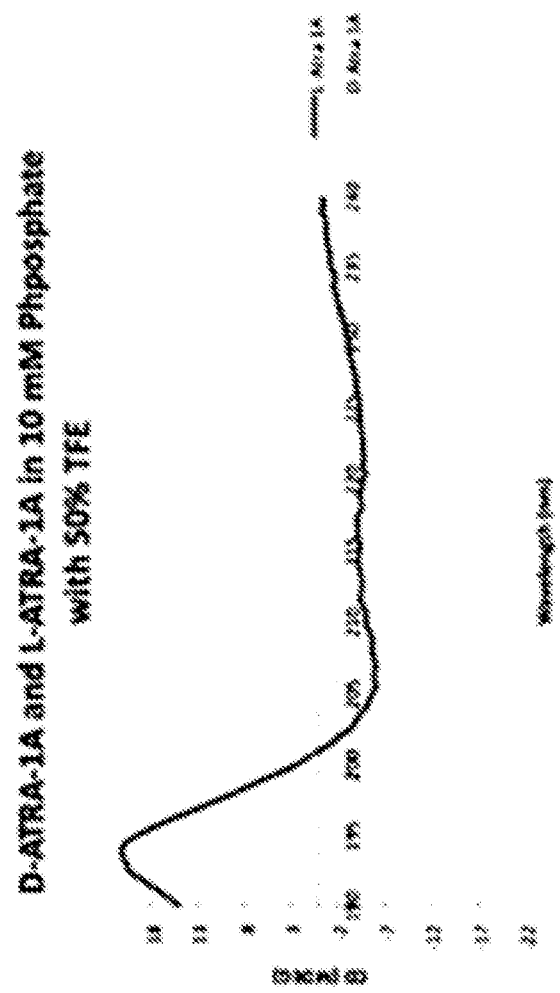

Spectroscopic analysis of the L-ATRA-1A in phosphate buffer (pH 7.4) using CD afforded a spectrum consistent with a peptide having a random coil conformation (FIG. 11), and analysis of the D-isomer afforded a spectrum that was the mirror image of that of the L-peptide, consistent with a D-peptide with a random coil conformation. When the ATRA-1A isomers were placed in phosphate buffer containing 50% trifluoroethanol (TFE), which is known to stabilize helical structure in membrane active peptides, the L-ATRA-1A presented a spectrum characteristic of a peptide that assumes a right-handed helical conformation, and the spectrum of D-ATRA-1A was the mirror image, indicating that the D-ATRA-1A assumed a left-handed helical conformation (FIGS. 11a and 11b). This behavior was consistent with the reported structural characteristics reported for enantiomeric pairs of other helical anti-microbial peptides.

These results for the L- and D-isomers of ATRA-1A suggested that they are good candidates. Further, their small size makes them amenable to designing variants to probe the contribution of peptide stereochemistry and other parameters to the performance of D-isomers of anti-microbial peptides.

TABLE 6

Helical cationic anti-microbial peptides

| Peptide | Sequence | Length | C terminus | Net charge* | SEQ ID NO: |
|---|---|---|---|---|---|
| ATRA-1A | KRAKKFFKKLK | 11 | -CONH$_2$ | +8 | 8 |
| NA-CATH | KRFKKFFKKLKNSVKKRAKKFFKKPKVIGVTFPF | 34 | -CO$_2$H | +15 | 1 |
| CAP-18 | GLRKRLRKFRNKIKEKLKKIGQKIQGLLPKLAPRTDY | 37 | -CO$_2$H | +13 | 9 |
| CAP-18$_{21a}$ | GLRKRLRKFRNKIKEKLKKIG | 21 | -CO$_2$H | +10 | 10 |
| Pleurocidin | GWGSFFKKAAHVGKHVGKAALTHYL | 25 | -CONH$_2$ | +5 | 11 |
| CA(1-13)-M(1-13) | KWKLFKKIEKVGQGIGAVLKVLTTGL | 26 | -CONH$_2$ | +6 | 12 |
| Melittin | GIGAVLKVLTTGLPALISWIKRKRQQ | 26 | -CONH$_2$ | +6 | 13 |

*Nominal charge at pH 7

Example 5—ATRA Peptide Stereochemistry and Performance

A series of peptide amides (Table 7) was designed based on the 11-residue repeat found in the *N. atra* NA-CATH peptide (Zhao et al., supra; de Latour et al., supra; and Amer et al., supra). ATRA-1A is a C-terminally amidated peptide with the sequence KRAKKFFKKLH-NH$_2$ (SEQ ID NO:8) and a charge of +8 at neutral pH. The sequence of the peptide is consistent with that of a helical anti-microbial peptide. With its largely positive charge, ATRA-1A interacts favorably with membranes rich in anionic lipids.

Short peptides such as ATRA-1A can be susceptible to proteolytic degradation, which could reduce their therapeutic potential. Thus, experiments were conducted to determine whether the D-enantiomer of ATRA-1A might be more resistant to proteases, enhancing the therapeutic potential relative to the parent L-peptide.

Environment and Peptide Structure:

To ascertain the significance of peptide stereochemistry and interactions between the peptide isomers and membranes, CD was used to study the structural properties of the peptide isomers in the presence of liposomes of varied PC/PG formulations. Using CD, the ratios of the signals corresponding to the n→π* and π→π* transition can provide insights into the nature of the helical conformation of a peptide (Yao et al. (2006) *Chinese J. Chem.* 24(5):705-710). Differences in the backbone dihedral angles associated with the different helical conformations (such as alpha- and 3-10 helices) result in characteristic CD spectral properties.

Figure 12B:
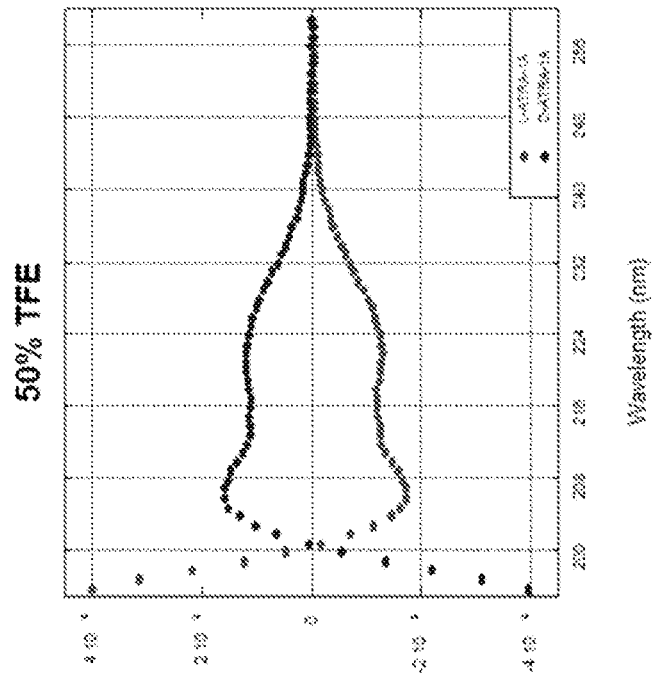
FIGS. 12a-12f are a series of graphs plotting CD spectra of L-ATRA-1A and D-ATRA-1A in 10 mM phosphate (FIG. 12a), 50% TFE (FIG. 12b), 100% PC liposomes (FIG. 12c), 80:20 PC/PG liposomes (FIG. 12d), 70:30 PC/PG liposomes (FIG. 12e), and 60:40 PC/PG liposomes (FIG. 12f).
Figure 12A:
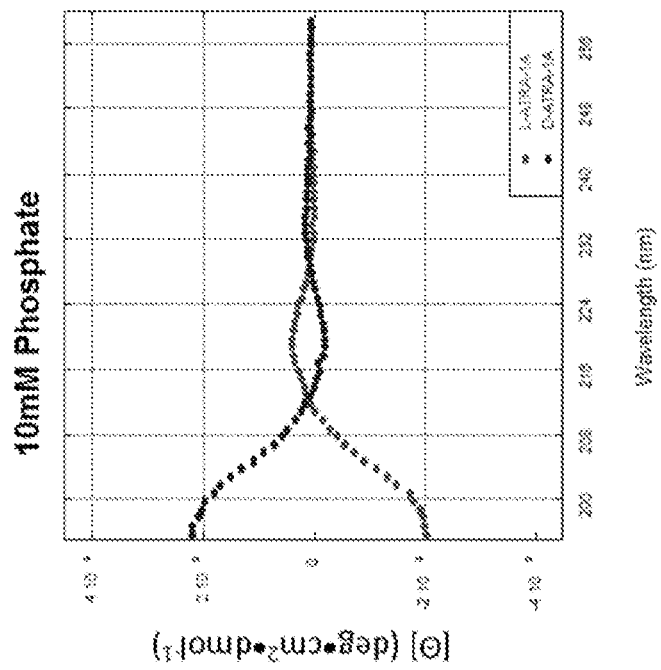
Figures 12C, 12D:
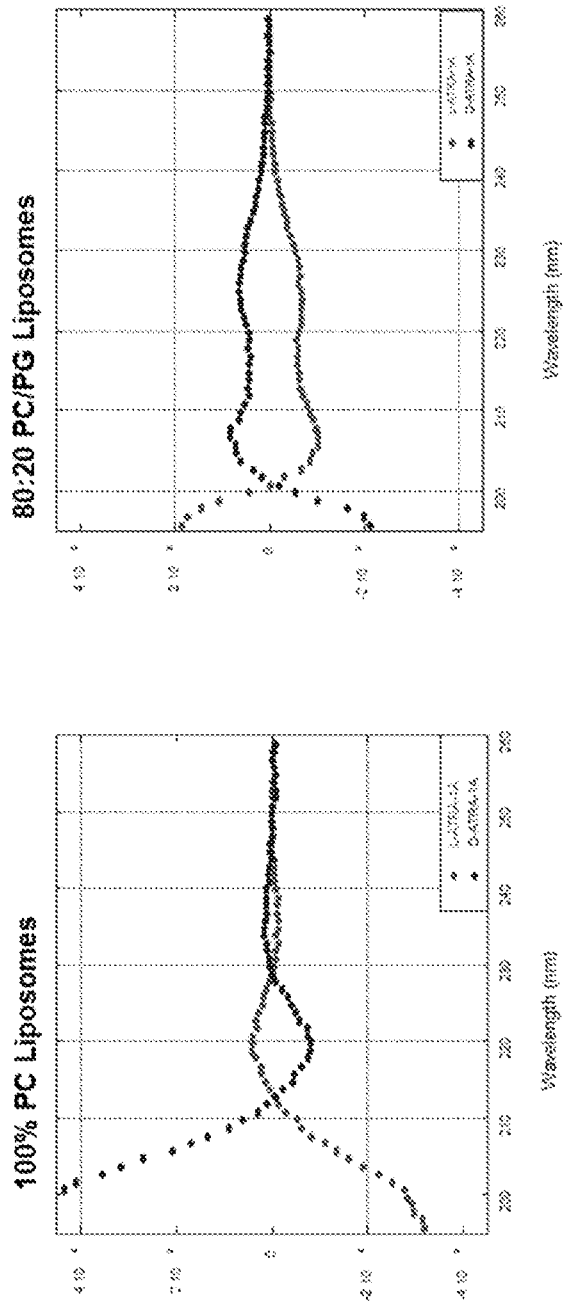
Figure 12F:
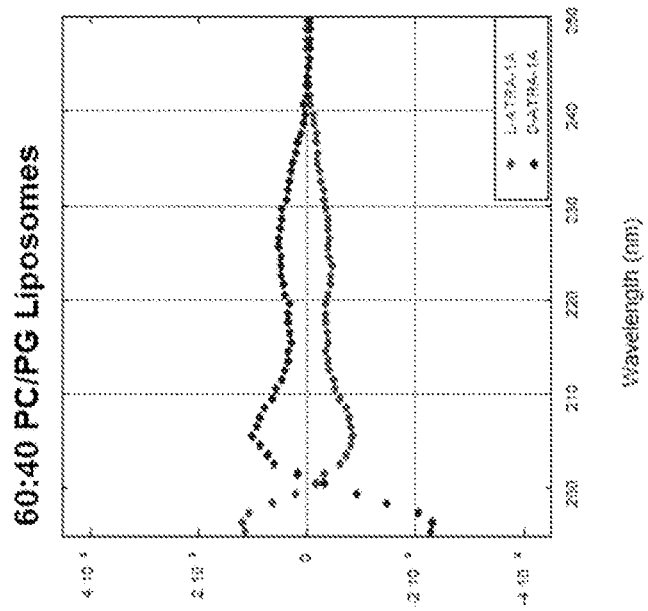
Figure 12E:
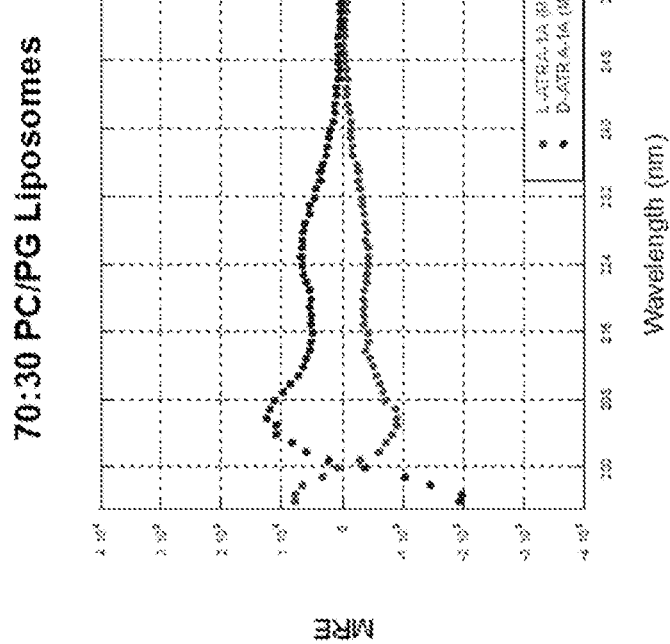

A Jasco J-815 spectropolarimeter was used to collect CD spectra. FIGS. 12*a*-12*e* show spectra from 190 to 260 nm at 25° C. using 0.2 nm intervals between scans at a scan speed of 5 nm/minute, with a total of five scans collected and averaged for each sample, where the peptide concentration in all samples was 62.5 µg/mL. In 10 mM phosphate buffer (pH 7.4), both ATRA-1A isomers exhibited spectra consistent with a random coil conformation (FIG. 12*a*). In 50% TFE, the L-ATRA-1A spectrum (FIG. 12*b*), with minima at 222 and 208 nm, denoted significant helical character. The spectrum for D-ATRA-1A was the mirror image of that for the L-peptide, indicating that it adopted a left-handed helical conformation. Both peptide isomers also adopted varied degrees of helical structure in 100% PC liposomes (FIG. 12*c*), 80:20 PC/PG liposomes (FIG. 12*d*), 70:30 PC/PG liposomes (FIG. 12*e*), and 60:40 PC/PG liposomes (FIG. 12*f*), with L-ATRA-1A adopting a right-handed helical conformation and the D-isomer forming a left-handed helix. The differences in peak ratios observed between peptide isomers interacting with 80:20 PC/PG liposomes, 70:30 PC/PG liposomes, and 60:40 PC/PG liposomes suggested that the helical conformation of the peptide isomers may differ as a function of lipid composition.

Further CD spectra were collected in SDS. The spectra for L- and D-ATRA-1A in 60 mM SDS in 10 mM phosphate, pH 7.4, again indicated that the peptide isomers had helical character, with D-ATRA-1A adopting a helix with the opposite chirality of that adopted by the L-isomer. A comparison of the spectra for D- and L-ATRA-1A in SDS and TFE suggested that neither peptide had as much helical character in SDS as it did in TFE.

The peak ratios of the n→π* and π→π* splitting were calculated for all helix forming samples (Table 8). The shift seen in the peak ratios between 50% TFE, 80:20 PC/PG liposomes and 60:40 PC/PG liposomes indicated a change in the helical conformations of these peptides. The peak ratio difference observed between D- and L-ATRA-1A in the 80:20 PC/PG liposomes suggested that the helical conformation of the peptide isomers differed under these conditions.

TABLE 7

NA-CATH-based peptides

| Peptide | Sequence | Molecular Weight | Nominal Charge* | SEQ ID NO: |
|---|---|---|---|---|
| NA-CATH | KRFKKFFKKLKNSVKKRAKKFFKKPKVIGVTFPF | 4175.2 | +15 | 1 |
| ATRA-1 | KRFKKFFKKLK-NH$_2$ | 1497.0 | +8 | 3 |
| ATRA-1A | KRAKKFFKKLK-NH$_2$ | 1420.8 | +8 | 8 |

TABLE 7 -continued

NA-CATH-based peptides

| Peptide | Sequence | Molecular Weight | Nominal Charge* | SEQ ID NO: |
|---|---|---|---|---|
| ATRA-1P | KRFKKFFKKPK-NH$_2$ | 1480.9 | +8 | 14 |
| ATRA-2 | KRAKKFFKKPK-NH$_2$ | 1404.8 | +8 | 4 |

*Nominal charge at pH 7

TABLE 8

Peak ratios of n → π* and π → π* splitting for helical peptides

| | 50% TFE | | 80:20 PC/PG liposomes | | 60:40 PC/PG liposomes | |
|---|---|---|---|---|---|---|
| | Wavelength (nm) | Signal Intensity (MRE) | Wavelength (nm) | Signal Intensity (MRE) | Wavelength (nm) | Signal Intensity (MRE) |
| | D-ATRA-1A | | D-ATRA-1A | | D-ATRA-1A | |
| n → π* | 221.4 | 1.21E+09 | 225.4 | 6.42E+08 | 226.4 | 5.27E+08 |
| π → π* | 206.2 | 1.61E+09 | 207.0 | 8.72E+08 | 205.8 | 9.98E+08 |
| Ratio | | 0.75 | | 0.74 | | 0.53 |
| | L-ATRA-1A | | L-ATRA-1A | | L-ATRA-1A | |
| n → π* | 222.2 | −1.30E+09 | 224.2 | −6.99E+08 | 223.8 | −4.43E+08 |
| π → π* | 206.0 | −1.72E+09 | 206.0 | −1.06E+09 | 205.4 | −8.44E+08 |
| Ratio | | 0.75 | | 0.66 | | 0.53 |

Figure 13:
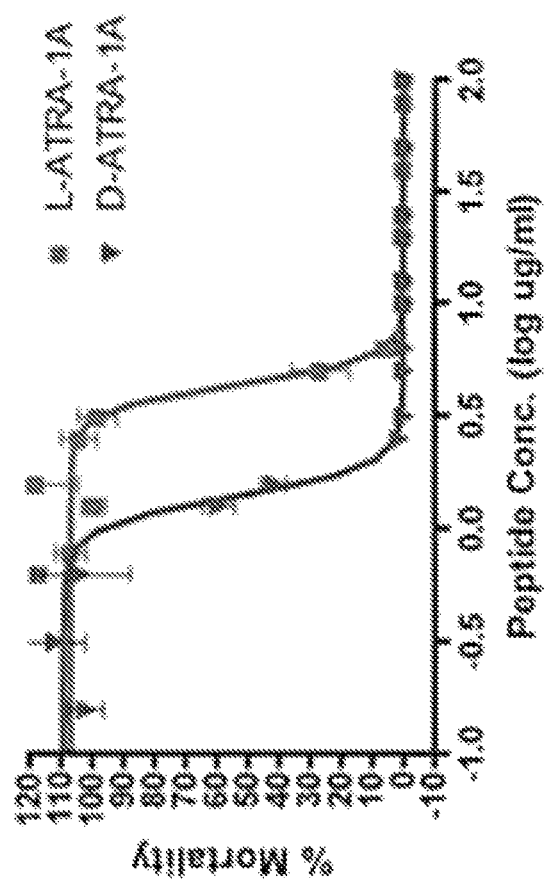
FIG. 13 a graph plotting survival of E. coli ATCC:25922 after treatment with L-ATRA-1A (squares) or D-ATRA-1A (triangles).

Anti-Microbial Performance:

The anti-microbial effectiveness of the D- and L-ATRA-1A isomers was determined against a panel of bacteria that included both Gram-positive (S. aureus) and Gram-negative (E coli ATCC:25922 and A. baumannii) microbes. Anti-microbial activity was determined for each peptide isomer by enumerating the number of viable colony forming units after incubating bacteria in media containing varied concentrations of peptide. In these studies, L-ATRA-1A exhibited higher potency against the Gram-positive bacterium than did the D-isomer, but D-ATRA-1A was more effective than the L-isomer against both of the Gram-negative bacteria that were tested (FIG. 13 and Table 8). Thus, the D- and L-isomers of the ATRA-1A peptide exhibited divergent anti-microbial potencies against Gram-negative and Gram-positive bacteria.

TABLE 9

Anti-microbial performance of ATRA-1A isomers (EC50, µg/mL)

| | L-ATRA-1A | D-ATRA-1A |
|---|---|---|
| S. aureus | 1.45 | 26.53 |
| E coli (ATCC 25922) | 4.323 | 1.302 |
| A. baumannii | 53.25 | 9.73 |

Electron Paramagnetic Resonance (EPR) and Perturbation:

In further studies, spectra were collected on a Bruker EMX X-band spectrometer (Bruker BioSpin Corp.; Billerica, Mass.) equipped with a high=−sensitivity resonator. Solution phase samples were held in a 0.6 mm I.D. glass capillary inserted into a larger quartz EPR tube. The nitroxide spin labeled lipids DOXYL-5 PC or TEMPO (Avanti Polar Lipids, Inc.; Alabaster, Ala.) were incorporated into the E. coli total lipid extract at a concentration of 1% on a molar basis. D- and L-ATRA-1A peptides were added at lipid:peptide ratios of 50, 25, and 10:1. The final lipid concentration was 1 mM.

Both peptides altered the behavior of the spin label in both the head group and the C-5 position of the acyl chain, which is close to the surface. Spectral shapes were consistent with the peptides constraining the spin label. Spectral shape analysis and rotational correlation times indicted that the D-isomer had a smaller effect on the motion of the spin-labels at both positions and at all lipid:peptide ratios tested.

Taken together, these results suggest a complex relationship between peptide stereochemistry and anti-microbial performance.

Example 6—D-ATRA Anti-Microbial Peptides

To further investigate the possibility that differences in the effectiveness of various cationic anti-microbial peptides are due at least in part to inherent structural properties of the peptides and their interactions with chiral elements of the lipid bi-layer, the role of chirality in determining the anti-microbial performance of L- and D-CAMPs was studied through comprehensive biophysical and biochemical characterization of peptide interactions with chiral lipids. By factoring in membrane composition and headgroup charge, the physical and chemical features that make CAMPs effective against specific types of membranes were identified. This approach was novel because of its focus on the chirality of both the peptides and the lipid membrane components.

Peptide Enantiomers:

A panel of CAMPs was selected to include peptides ranging from 11 to 37 residues in length (Table 6), although the primary focus was on the enantiomeric pairs of the shorter peptides (11-26 residues). The longer peptides (NA-CATH and CAP-18) were included to provide a basis for comparing the performance and biophysical data of the shorter peptide isomers to that of full-length anti-microbial peptides.

A series of 11-residue peptide amides based on the repeated NA-CATH pattern was designed, and evaluated for anti-microbial effectiveness against different organisms. ATRA-1A was one of the 11-residue NA-CATH-based peptides that was found to demonstrate significant anti-microbial activity, slightly less than that of the full length NA-CATH. Effects of the L- and D-isoforms of the ATRA-1A peptide on cell survival and biofilm formation were then examined.

Figure 14:
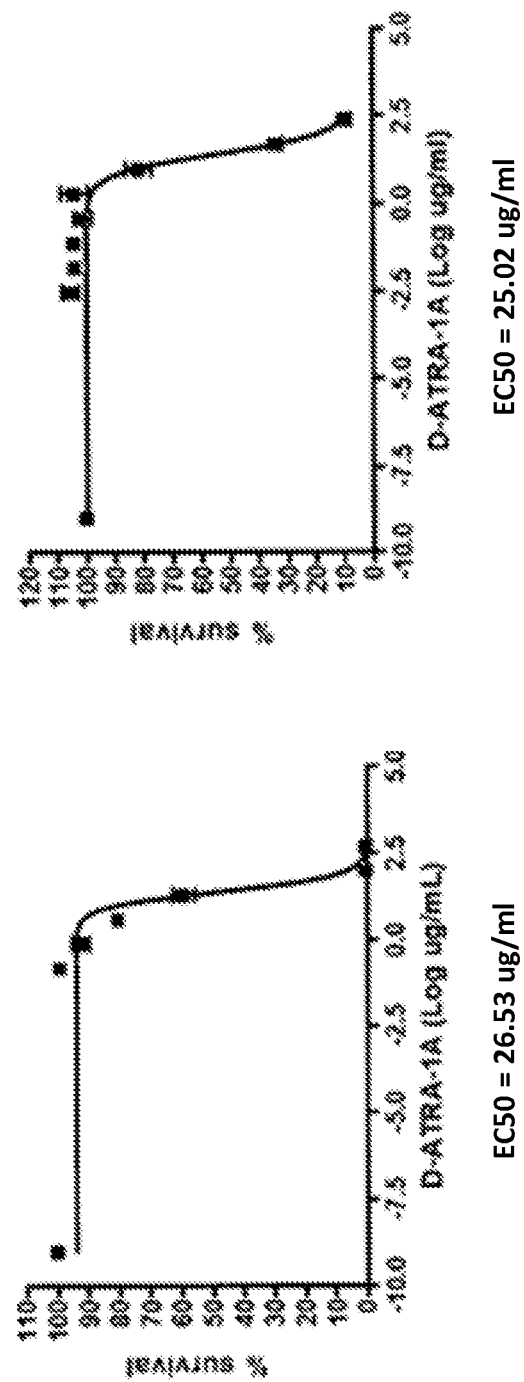
FIG. 14 is a pair of graphs plotting the results of representative experiments demonstrating the anti-microbial effectiveness of D-ATRA-1A against S. aureus.
Figure 15:
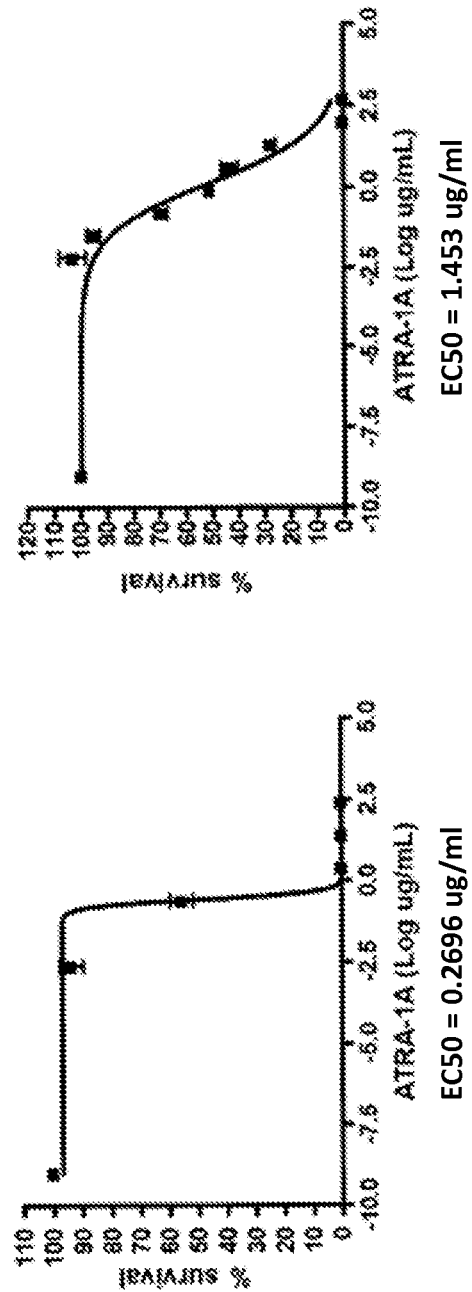
FIG. 15 is a pair of graphs plotting the results of representative experiments demonstrating the anti-microbial effectiveness of L-ATRA-1A against S. aureus.
Figure 16:
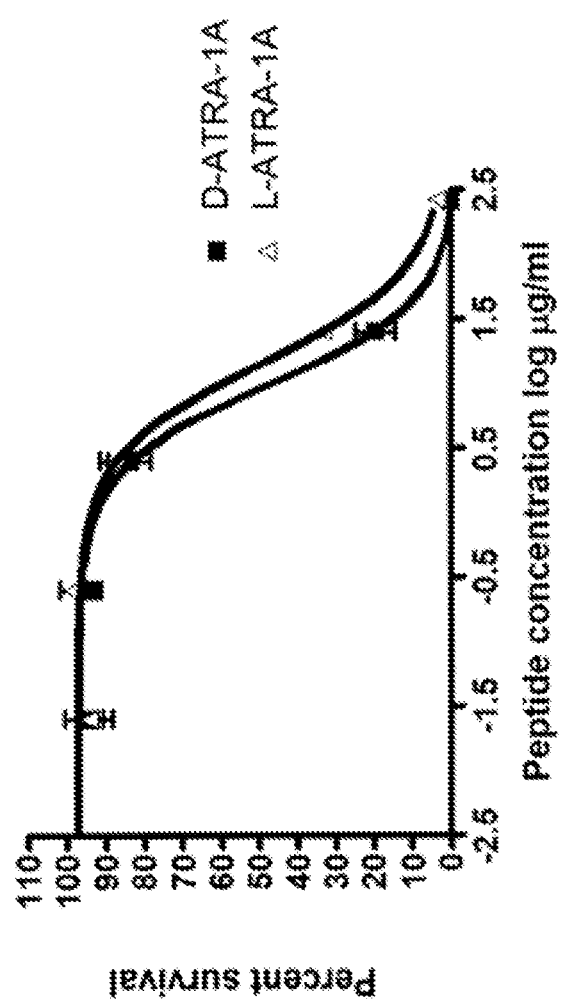
FIG. 16 is a graph plotting survival of P. aeruginosa after treatment with D-ATRA-1A (solid squares) or L-ATRA-1A (open triangles).

Anti-Microbial Activity of L- and D-ATRA-1A:

The L- and D-isomers of ATRA-1A demonstrated significantly different anti-microbial potencies against *S. aureus, P. aeruginosa*, and *A. baumannii*. In experiments using *S. aureus*, fitting the two best data sets provided EC50 values of 26.53 and 25.02 µg/ml for D-ATRA-1A (FIG. 14, left and right panels, respectively), and 0.2696 and 1.453 µg/ml for L-ATRA-1A (FIG. 15, left and right panels, respectively). L-ATRA-1A thus was more effective against *S. aureus* than the D-isoform. In contrast, experiments using *P. aeruginosa* showed that D-ATRA-1A had an average EC50 of 9.643 (CI 6.5 to 14.2), while L-ATRA-1A had an average EC50 of 14.22 (CI 10.4 to 19.4) (FIG. 16). Thus, D-ATRA-1A was slightly more effective than L-ATRA-1A as an anti-microbial agent against *P. aeruginosa*.

Figure 17:
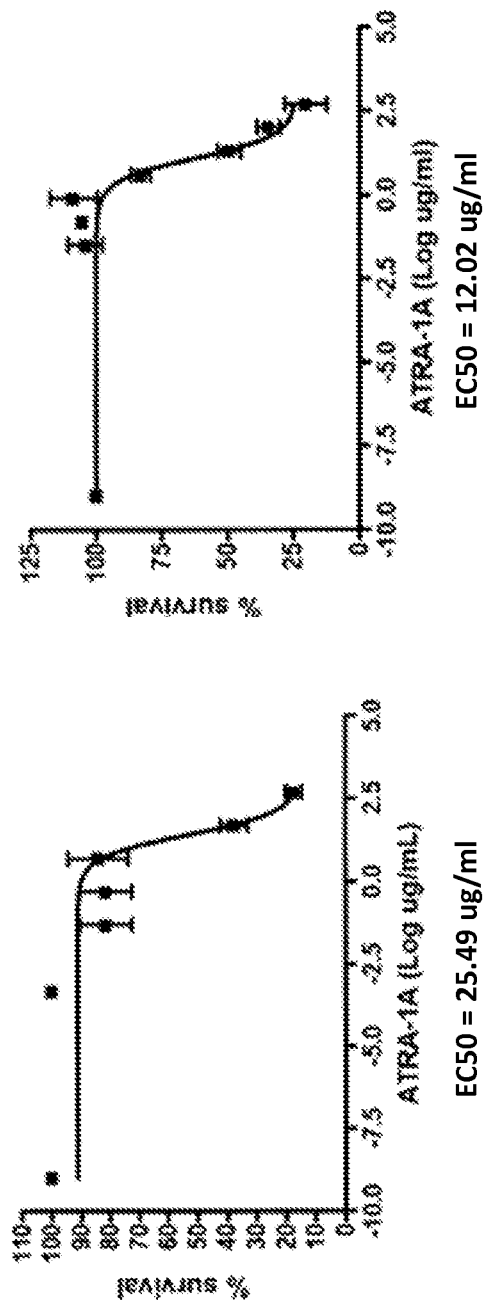
FIG. 17 is a pair of graphs plotting the results of representative experiments demonstrating the anti-microbial effectiveness of L-ATRA-1A against P. aeruginosa.
Figure 18:
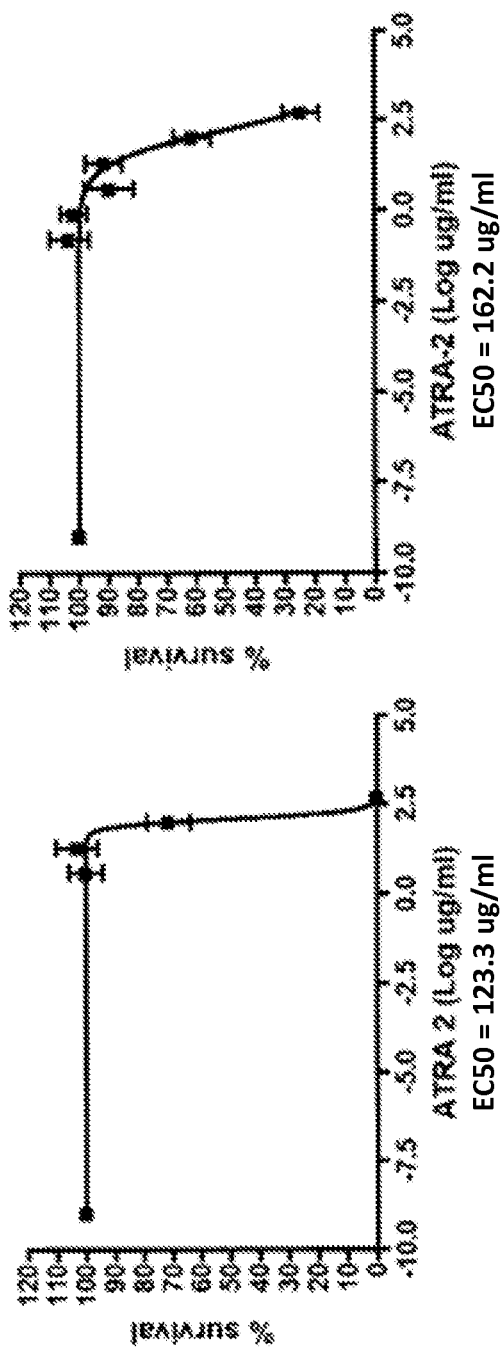
FIG. 18 is a pair of graphs plotting the results of representative experiments demonstrating the anti-microbial effectiveness of L-ATRA-2 against P. aeruginosa.
Figure 19:
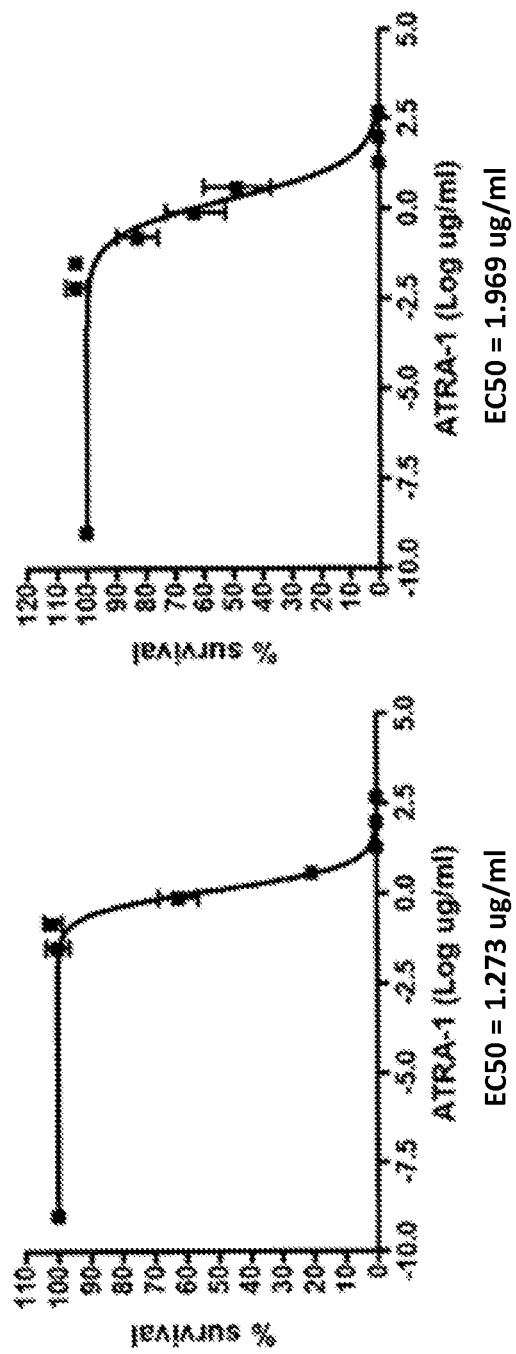
FIG. 19 is a pair of graphs plotting the results of representative experiments demonstrating the anti-microbial effectiveness of L-ATRA-1 against P. aeruginosa.

Additional studies were conducted to examine the effectiveness of L-ATRA-1A, L-ATRA-1, and L-ATRA-2 against *P. aeruginosa*. L-ATRA-1A [FIG. 17; EC50s of 25.49 µg/ml (left panel) and 12.02 µg/ml (right panel)] was more effective than L-ATRA-2 [FIG. 18; EC50s of 123.3 µg/ml (left panel) and 162.2 µg/ml (right panel)], but not quite as effective as L-ATRA-1 [FIG. 19; EC50s of 1.273 µg/ml (left panel) and 1.969 µg/ml (right panel)].

Figure 20:
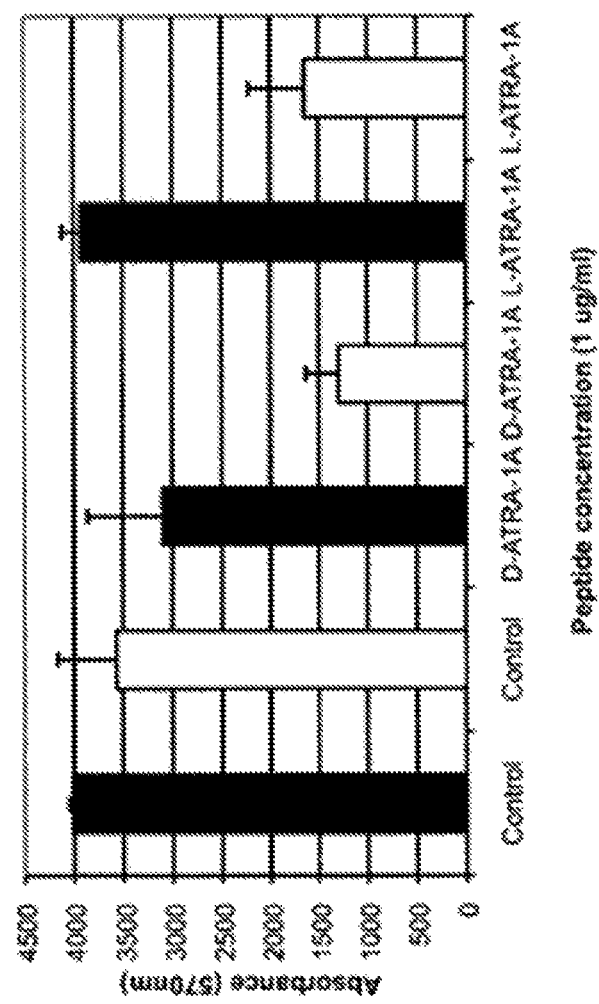
FIG. 20 is a graph plotting biofilm growth of P. aeruginosa (black bars) and S. aureus (white bars) in the presence of D-ATRA-1A and L-ATRA-1A.

Anti-Biofilm Properties of L- and D-ATRA-1A:

The peptides also had anti-biofilm activity in *P. aeruginosa* and *S. aureus*. As shown in FIG. 20, 1 µg/ml D-ATRA-1A was more effective at inhibiting biofilm growth of both *P. aeruginosa* (black bars) and *S. aureus* (white bars).

Example 7—Effect of Molecular Crowding Agents on CAMP Activity

Molecular crowding is a major factor in the cellular environment. Cells contain hundreds of different macromolecules that occupy 20-30% of the cell volume. Molecular crowding agents such as FICOLL™ 70 (a cross-linked polysaccharide of sucrose monomers), polyethylene glycol (PEG), and dextran can be used to simulate the effect that these macromolecules may have on other peptides and proteins in the cellular environment. Thus, experiments were conducted to determine whether molecular crowding has an effect on the properties of anti-microbial peptides.

As indicated in Table 10 below, the presence of 20% FICOLL™ 70 dramatically enhanced the anti-microbial performance of L-ATRA-1A and D-ATRA-1A against both Gram-negative *E. coli* (ATCC 25922) and Gram-positive *B. cereus* (ATCC 11778). In particular, L-ATRA-1A showed a 10.66-fold increase in potency against *E. coli* and a 14-fold increase against *B. cereus*, while D-ATRA-1A showed a 13.66-fold increase in potency against *E. coli* and 54.34-fold increase in potency against *B. cereus*. While, the mechanism is still under investigation, molecular crowding has been shown to affect aggregation of other proteins in solution.

TABLE 10

Anti-microbial performance with and without FICOLL ™ 70

| | EC50 (µg/ml) without FICOLL ™ 70 | | EC50 (µg/ml) with 20% FICOLL ™ 70 | |
| --- | --- | --- | --- | --- |
| | L-ATRA-1A | D-ATRA-1A | L-ATRA-1A | D-ATRA-1A |
| *E. coli* (ATCC 25922) | 4.232 | 1.302 | 0.420 | 0.0850 |
| *B. cereus* (ATCC 11778) | 72.41 | 2.330 | 5.207 | 0.04060 |

Figure 21A:
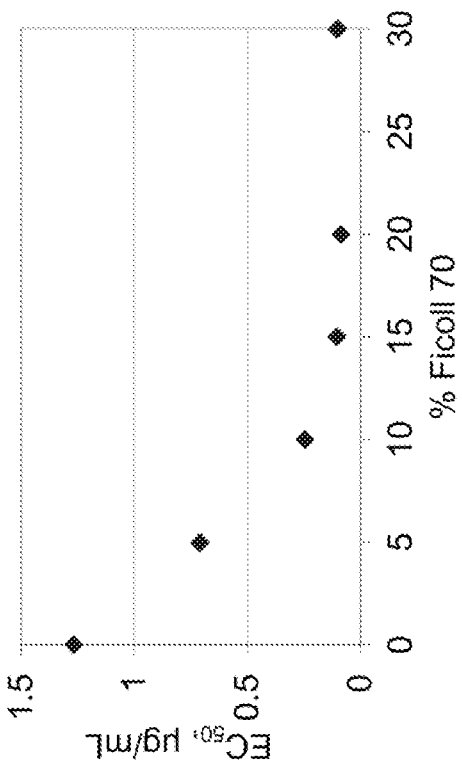
FIG. 21a is a graph plotting percent survival of E. coli treated with varying concentrations of D-ATRA-1A in the absence (filled circles) and presence (open circles) of 20% FICOLL™ 70.
Figure 21B:
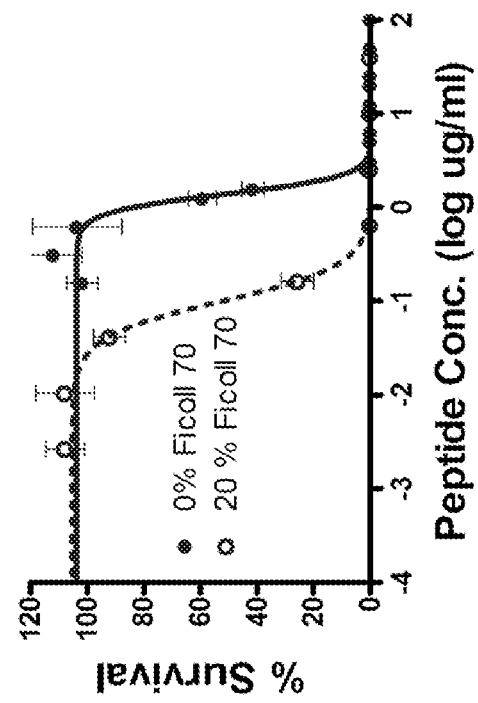
FIG. 21b is a graph plotting the EC50 for D-ATRA-1A against E. coli in the presence of increasing amounts of FICOLL™ 70.
Figure 22B:
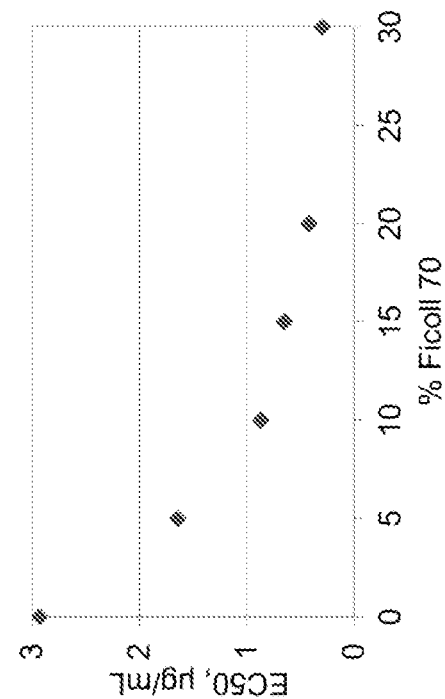
FIG. 22b is a graph plotting the EC50 for L-ATRA-1A against E. coli in the presence of increasing amounts of FICOLL™ 70.
Figure 22A:
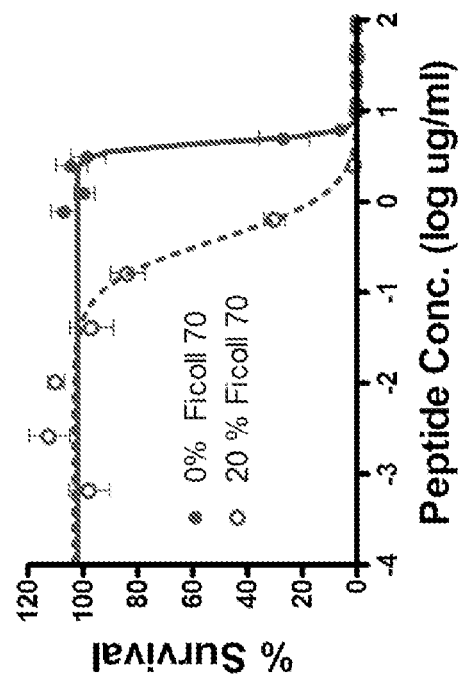
FIG. 22a is a graph plotting percent survival of E. coli treated with varying concentrations of L-ATRA-1A in the absence (filled circles) and presence (open circles) of 20% FICOLL™ 70.

The anti-microbial performance of the D- and L-isomers of ATRA-1A was tested against *E. coli* (ATCC: 25922) in the presence of increasing amounts of FICOLL™ 70. In these assays, bacteria ($1 \times 10^5$ CFU/ml) were incubated for 3 hours at 37° C. with varied concentrations of peptide in 10 mM phosphate buffer (pH 7.4) containing 0 to 30% FICOLL™ 70. The potencies of the peptide isomers were determined by plotting bacterial survival (%) as a function of log peptide concentration and fitting the data to a standard dose response equation. Each experiment was conducted at least three times, with the exception of experiments with 15% and 30% FICOLL™, which were only performed once. As indicated in Table 11 and FIGS. 21 and 22, as the concentration of FICOLL™ 70 was increased, the EC50 for both D-ATRA-1A (FIG. 21) and L-ATRA-1A (FIG. 22) decreased.

TABLE 11

Anti-microbial performance with increasing amounts of FICOLL ™ 70

| | Average EC50 | |
| --- | --- | --- |
| % FICOLL ™ | L-ATRA-1A | D-ATRA-1A |
| 0 | 2.9 | 1.3 |
| 5 | 1.6 | 0.71 |
| 10 | 0.86 | 0.24 |
| 15 | 0.64 | 0.10 |
| 20 | 0.42 | 0.085 |
| 30 | 0.29 | 0.010 |

Figure 23:
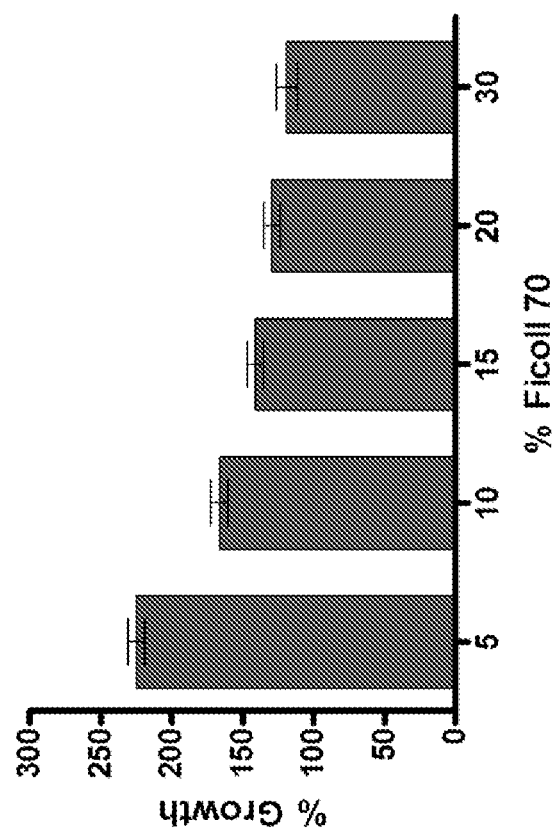
FIG. 23 is a graph plotting the growth of E. coli in the presence of increasing concentrations of FICOLL™ 70, as a percentage of growth observed in the absence of 70.

Bacterial growth in the presence of FICOLL™ 70 but without CAMPs also was evaluated. As shown in FIG. 23, increased growth of *E. coli* was observed in the presence of FICOLL™ 70. At 5% FICOLL™ 70, *E. coli* growth was more than twice the growth of *E. coli* without FICOLL™ 70. At 30% FICOLL™ 70, there was only a slight increase of bacterial growth as compared to 5% FICOLL™ 70.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A purified peptide having a length of 11 amino acids, said peptide comprising:
   (a) the amino acid sequence set forth in SEQ ID NO:3;
   (b) the amino acid sequence set forth in SEQ ID NO:3 with one substitution;
   (c) the amino acid sequence set forth in SEQ ID NO:4;
   (d) the amino acid sequence set forth in SEQ ID NO:4 with one substitution;
   (e) the amino acids sequence set forth in SEQ ID NO:8; or
   (f) the amino acid sequence set forth in SEQ ID NO:8 with one substitution, wherein at least 20 percent of the amino acids in said peptide are D-amino acids.

2. The purified peptide of claim 1, wherein said peptide comprises the amino acid sequence set forth in SEQ ID NO:3.

3. The purified peptide, of claim 1, wherein said peptide comprises the amino acid sequence set forth in SEQ ID NO:3 with one substitution.

4. The purified peptide of claim 1, wherein said peptide comprises the amino acid sequence set forth in SEQ ID NO:4.

5. The purified peptide of claim 1, wherein said peptide comprises the amino add sequence set forth in SEQ ID NO:4 with one substitution.

6. The purified peptide of claim 1, wherein said peptide comprises the amino acids sequence set forth in SEQ ID NO:8.

7. The purified peptide of claim 1, wherein said peptide comprises the amino add sequence set forth in SEQ ID NO:8 with one substitution.

8. The purified peptide of claim 1, wherein at least 50 percent of the amino acids in said peptide are D-amino acids.

9. The purified peptide of claim 1, wherein said peptide consists of D-amino acids.

10. A composition comprising the peptide of claim 1 and an excipient, wherein the excipient comprises one or more of saline, a polyalkylene glycol, a vegetable oil, a hydrogenated naphthalene, polyvinylpyrrolidone, hydroxypropyl methylcellulose, lactose, gelatin, calcium sulfate, starch, polyethylene glycol, sodium acetate, sodium starch glycolate, sodium lauryl sulfate, a lactide polymer, lactide/glycolide copolymer or polyoxethylene-polyoxypropylene copolymer.

11. The composition of claim 10, wherein said composition comprises a molecular crowding agent, wherein the molecular crowding agent is a neutral, highly branched, high-mass, hydrophilic polysaccharide that dissolves readily in aqueous solution, or dextran.

12. A composition comprising are excipient, a first peptide of claim 1 and a second peptide of claim 1, wherein said first and second peptides have different amino acid sequences or different ratios of L- and D-amino acids, wherein the excipient comprises one or more of saline, a polyalkylene glycol, a vegetable oil, a hydrogenated naphthalene, polyvinylpyrrolidone, hydroxypropyl methylcellulose, lactose, gelatin, calcium sulfate, starch, polyethylene glycol, sodium acetate, sodium starch glycolate, sodium lauryl sulfate, a lactide polymer, lactide/glycolide copolymer or polyoxethylene-polyoxypropylene copolymer.

13. The composition of claim 12, wherein said composition comprises a molecular crowding agent, wherein the molecular crowding agent is a neutral, highly branched, high-mass, hydrophilic polysaccharide that dissolves readily in aqueous solution, or dextran.

14. An article of manufacture comprising the purified peptide of claim 1.

15. The purified peptide of claim 1, wherein the peptide consists essentially of:
 (a) the amino acid sequence set forth in SEQ ID NO:3;
 (b) the amino acid sequence set forth in SEQ ID NO:3 with one substitution;
 (c) the amino acid sequence set forth in SEQ ID NO:4;
 (d) the amino acid sequence set forth in SEQ ID NO:4 with one substitution;
 (e) the amino acid sequence set forth in SEQ ID NO:8; or
 (f) the amino acid sequence set forth in KO ID NO:8 with one substitution, wherein at least 20 percent of the amino acids in said peptide are D-amino acids.

16. The purified peptide of claim 1, wherein the peptide is amidated at the C-terminus.

17. The composition of claim 10, wherein the peptide consists essentially of:
 (a) the amino acid sequence set forth in SEQ ID NO:3;
 (b) the amino acid sequence set forth in SEQ ID NO:3 with one substitution;
 (c) the amino add sequence set forth in SEQ ID NO:4;
 (d) the amino add sequence set forth in SEQ ID NO:4 with one substitution;
 (e) the amino adds sequence set forth in SEQ ID NO:8; or
 (f) the amino add sequence set forth in SEQ ID NO:8 with one substitution, wherein at least 20 percent of the amino acids in said peptide are D-amino adds.

18. The composition of claim 10, wherein the peptide is amidated at the C-terminus.

19. The composition of claim 12, wherein the first and second peptides consist essentially of:
 (a) the amino add sequence set forth in SEQ ID NO:3;
 (b) the amino add sequence set forth in SEQ ID NO:3 with one substitution or;
 (c) the amino add sequence set forth in SEQ ID NO:4;
 (d) the amino add sequence set forth in SEQ ID NO:4 with one substitution or;
 (e) the amino adds sequence set forth in SEQ ID NO:8; or
 (f) the amino add sequence set forth n SEQ ID NO:8 with one substitution or, wherein at least 20 percent of the amino acids in said peptide are D-amino acids.

20. The composition of claim 12, wherein the first and second peptides are amidated at the C-terminus.

21. The article of manufacture of claim 14, wherein the peptide consists essentially of:
 (a) the amino acid sequence set forth in SEQ ID NO:3;
 (b) the amino acid sequence set forth in SEQ ID NO:3 with one substitution;
 (c) the amino acid sequence set forth in SEQ ID NO:4;
 (d) the amino acid sequence set forth in SEQ ID NO:4 with one substitution;
 (e) the amino acid sequence set forth in SEQ ID NO:8; or
 (f) the amino acid sequence set forth in KO ID NO:8 with one substitution, wherein at least 20 percent of the amino acids in said peptide are D-amino acids.

22. The article of manufacture of claim 14, wherein the peptide is amidated at the C-terminus.

23. The purified peptide of claim 1, wherein the peptide comprises the amino acid sequence set forth in SEQ ID NO:3 with one substitution, wherein the substitution is an alanine substituted for the phenylalanine at position 3 of SEQ ID NO:3 or a proline substituted for the lysine at position 10 of SEQ ID NO:3.

24. The purified peptide of claim 2, wherein said peptide consists of the amino acid sequence set forth in SEQ ID NO:3.

* * * * *

SEQUENCE LISTING

<160> NUMBER OF SEQ ID NOS: 14

<210> SEQ ID NO 1
<211> LENGTH: 34
<212> TYPE: PRT
<213> ORGANISM: Naja atra

<400> SEQUENCE: 1

Lys Arg Phe Lys Lys Phe Phe Lys Lys Leu Lys Asn Ser Val Lys Lys
 1               5                  10                  15

Arg Ala Lys Lys Phe Phe Lys Lys Pro Lys Val Ile Gly Val Thr Phe
                20                  25                  30

Pro Phe

<210> SEQ ID NO 2
<211> LENGTH: 34
<212> TYPE: PRT
<213> ORGANISM: Artificial Sequence
<220> FEATURE:
<223> OTHER INFORMATION: synthetic peptide

<400> SEQUENCE: 2

Lys Arg Phe Lys Lys Phe Phe Lys Lys Leu Lys Asn Ser Val Lys Lys
 1               5                  10                  15

Arg Phe Lys Lys Phe Phe Lys Lys Leu Lys Val Ile Gly Val Thr Phe
                20                  25                  30

Pro Phe

<210> SEQ ID NO 3
<211> LENGTH: 11
<212> TYPE: PRT
<213> ORGANISM: Artificial Sequence
<220> FEATURE:
<223> OTHER INFORMATION: synthetic peptide

<400> SEQUENCE: 3

Lys Arg Phe Lys Lys Phe Phe Lys Lys Leu Lys
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: synthetic peptide

<400> SEQUENCE: 4

Lys Arg Ala Lys Lys Phe Phe Lys Lys Pro Lys
 1               5                  10

<210> SEQ ID NO 5
<211> LENGTH: 37
<212> TYPE: PRT
<213> ORGANISM: Artificial Sequence
<220> FEATURE:
<223> OTHER INFORMATION: synthetic peptide

<400> SEQUENCE: 5

Leu Leu Gly Asp Phe Phe Arg Lys Ser Lys Glu Lys Ile Gly Lys Glu
 1               5                  10                  15

Phe Lys Arg Ile Val Gln Arg Ile Lys Asp Phe Leu Arg Asn Leu Val
                20                  25                  30

Pro Arg Thr Glu Ser

35

<210> SEQ ID NO 6
<211> LENGTH: 34
<212> TYPE: PRT
<213> ORGANISM: Artificial Sequence
<220> FEATURE:
<223> OTHER INFORMATION: synthetic peptide

<400> SEQUENCE: 6

Gly Leu Leu Arg Lys Gly Gly Glu Lys Ile Gly Glu Lys Leu Lys Lys
 1               5                  10                  15

Ile Gly Gln Lys Ile Lys Asn Phe Phe Gln Lys Leu Val Pro Gln Pro
            20                  25                  30

Glu Gln

<210> SEQ ID NO 7
<211> LENGTH: 37
<212> TYPE: PRT
<213> ORGANISM: Artificial Sequence
<220> FEATURE:
<223> OTHER INFORMATION: synthetic peptide

<400> SEQUENCE: 7

Gly Leu Lys Leu Arg Phe Glu Phe Ser Lys Ile Lys Gly Glu Phe Leu
 1               5                  10                  15

Lys Thr Pro Glu Val Arg Phe Arg Asp Ile Lys Leu Lys Asp Asn Arg
            20                  25                  30

Ile Ser Val Gln Arg
        35

<210> SEQ ID NO 8
<211> LENGTH: 11
<212> TYPE: PRT
<213> ORGANISM: Artificial Sequence
<220> FEATURE:
<223> OTHER INFORMATION: synthetic peptide

<400> SEQUENCE: 8

Lys Arg Ala Lys Lys Phe Phe Lys Lys Leu Lys
 1               5                  10

<210> SEQ ID NO 9
<211> LENGTH: 37
<212> TYPE: PRT
<213> ORGANISM: Artificial Sequence
<220> FEATURE:
<223> OTHER INFORMATION: synthetic peptide

<400> SEQUENCE: 9

Gly Leu Arg Lys Arg Leu Arg Lys Phe Arg Asn Lys Ile Lys Glu Lys
 1               5                  10                  15

Leu Lys Lys Ile Gly Gln Lys Ile Gln Gly Leu Leu Pro Lys Leu Ala
            20                  25                  30

Pro Arg Thr Asp Tyr
        35

<210> SEQ ID NO 10
<211> LENGTH: 21
<212> TYPE: PRT
<213> ORGANISM: Artificial Sequence
<220> FEATURE:
<223> OTHER INFORMATION: synthetic peptide

```
<400> SEQUENCE: 10

Gly Leu Arg Lys Arg Leu Arg Lys Phe Arg Asn Lys Ile Lys Glu Lys
1               5                   10                  15

Leu Lys Lys Ile Gly
            20

<210> SEQ ID NO 11
<211> LENGTH: 25
<212> TYPE: PRT
<213> ORGANISM: Artificial Sequence
<220> FEATURE:
<223> OTHER INFORMATION: synthetic peptide

<400> SEQUENCE: 11

Gly Trp Gly Ser Phe Phe Lys Lys Ala Ala His Val Gly Lys His Val
1               5                   10                  15

Gly Lys Ala Ala Leu Thr His Tyr Leu
            20                  25

<210> SEQ ID NO 12
<211> LENGTH: 26
<212> TYPE: PRT
<213> ORGANISM: Artificial Sequence
<220> FEATURE:
<223> OTHER INFORMATION: synthetic peptide

<400> SEQUENCE: 12

Lys Trp Lys Leu Phe Lys Lys Ile Glu Lys Val Gly Gln Gly Ile Gly
1               5                   10                  15

Ala Val Leu Lys Val Leu Thr Thr Gly Leu
            20                  25

<210> SEQ ID NO 13
<211> LENGTH: 26
<212> TYPE: PRT
<213> ORGANISM: Artificial Sequence
<220> FEATURE:
<223> OTHER INFORMATION: synthetic peptide

<400> SEQUENCE: 13

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 14
<211> LENGTH: 11
<212> TYPE: PRT
<213> ORGANISM: Artificial Sequence
<220> FEATURE:
<223> OTHER INFORMATION: synthetic peptide

<400> SEQUENCE: 14

Lys Arg Phe Lys Lys Phe Phe Lys Lys Pro Lys
1               5                   10
```